United States Patent
Sledziewski et al.

(10) Patent No.: US 9,605,306 B2
(45) Date of Patent: Mar. 28, 2017

(54) METHODS AND NUCLEIC ACIDS FOR THE ANALYSIS OF GENE EXPRESSION ASSOCIATED WITH THE DEVELOPMENT OF PROSTATE CELL PROLIFERATIVE DISORDERS

(71) Applicant: EPIGENOMICS AG, Berlin (DE)

(72) Inventors: Andrew Z. Sledziewski, Shoreline, WA (US); Catherine E. Lofton-Day, Seattle, WA (US); Reimo Tetzner, Berlin (DE); Juergen Distler, Berlin (DE); Fabian Model, Berlin (DE); Shannon Payne, Seattle, WA (US); Dimo Dietrich, Berlin (DE)

(73) Assignee: EPIGENOMICS AG, Berlin (DE)

( * ) Notice: Subject to any disclaimer, the term of this patent is extended or adjusted under 35 U.S.C. 154(b) by 0 days.

(21) Appl. No.: 14/263,906

(22) Filed: Apr. 28, 2014

(65) Prior Publication Data

US 2014/0227700 A1 Aug. 14, 2014

Related U.S. Application Data

(63) Continuation of application No. 12/515,520, filed as application No. PCT/EP2007/010257 on Nov. 26, 2007, now abandoned.

(30) Foreign Application Priority Data

Nov. 24, 2006 (EP) .................................. 06124746

(51) Int. Cl.
 *C12Q 1/68* (2006.01)
(52) U.S. Cl.
 CPC .......... *C12Q 1/686* (2013.01); *C12Q 1/6886* (2013.01); *C12Q 2523/125* (2013.01); *C12Q 2600/154* (2013.01); *C12Q 2600/156* (2013.01); *C12Q 2600/158* (2013.01)
(58) Field of Classification Search
 None
 See application file for complete search history.

(56) References Cited

U.S. PATENT DOCUMENTS

| | | | |
|---|---|---|---|
| 2010/0092953 A1 | 4/2010 | Dietrich et al. | |
| 2010/0092981 A1 | 4/2010 | Shuber | |

FOREIGN PATENT DOCUMENTS

| | | | |
|---|---|---|---|
| WO | 2004/067777 A1 | 8/2004 | |
| WO | 2005/054517 A2 | 6/2005 | |
| WO | WO 2006/128140 A2 | 11/2006 | |
| WO | 2008/009478 A1 | 1/2008 | |

OTHER PUBLICATIONS

Strausberg et al., In Microarrays and Cancer Research, 2002, Warrington et al (eds.) Eaton Publishing, Westborough, MA pp. xi-xvi.
Notterman et al., In Microarrays and Cancer Research, Warrington et al (eds.) Eaton Publishing, Westborough, MA pp. 81-111.
Phillips, Theresa: "*Regulation of Transcription and Gene Expression in Eukaryotes*"; Nature Education, 2008; 1(1)199.
Chung et al. (2005) "Identification of differentially methylated sequences in prostate cancer," In; Proc. Amer. Assoc. Cancer. Res. vol. 46. Abstract No. 909.
Chung et al. (2006) "Identification of novel hypermethylated genes in primary prostate cancer and colon cancer," In; Proc. Amer. Assoc. Cancer. Res. vol. 47. Abstract No. 58.
Hesson et al. (2005) "CpG island promoter hypermethylation of a novel Ras-effector gene RASSF2A is an early event in colon carcinogenesis and correlates inversely with K-ras mutations," Oncogene. 24:3987-3994.
Endoh et al. (2005) "RASSF2, a potential tumour suppressor, is silenced by CpG island hypermethylation in gastric cancer," Br. J. Cancer. 93(12):1395-1399.
International Search Report with Written Opinion corresponding to International Patent Application No. PCT/EP2007/010257, mailed Mar. 17, 2008.

*Primary Examiner* — James Martinell
(74) *Attorney, Agent, or Firm* — Lathrop & Gage LLP; James H. Velema, Esq.; Sean M. Coughlin, Esq.

(57) ABSTRACT

The invention provides methods, nucleic acids and kits for detecting prostate cell proliferative disorders. The invention discloses genomic sequences the methylation patterns of which have utility for the improved detection of said disorder, thereby enabling the improved diagnosis and treatment of patients.

3 Claims, 5 Drawing Sheets

METHODS AND NUCLEIC ACIDS FOR THE ANALYSIS OF GENE EXPRESSION ASSOCIATED WITH THE DEVELOPMENT OF PROSTATE CELL PROLIFERATIVE DISORDERS

CROSS REFERENCE TO RELATED APPLICATIONS

This application is a continuation application of U.S. application Ser. No. 12/515,520, filed Apr. 19, 2010, now pending; which is a 35 USC §371 National Stage application of International Application No. PCT/EP2007/010257, filed Nov. 26, 2007; which claims the benefit of priority to EP06124746.6, filed Nov. 24, 2006, now expired. The disclosure of each of the prior applications is considered part of, and is incorporated by reference in, the disclosure of this application.

FIELD OF THE INVENTION

The present invention relates to genomic DNA sequences that exhibit altered expression patterns in disease states relative to normal. Particular embodiments provide methods, nucleic acids, nucleic acid arrays and kits useful for detecting, or for diagnosing prostate carcinoma.

PRIOR ART

Prostate cancer is the most common cancer and the third leading cause of death in American men (Jemal et al., 2006). Incidence and mortality rates for this disease increase greatly with age, with more than 65% of all prostate cancer cases diagnosed in men older than 65 (Jemal et al., 2006). Stage of disease at diagnosis also affects overall survival rates. Due to widespread use of the prostate-specific antigen (PSA) screening test, nearly 90% of new patients are diagnosed with local or regional disease (Jemal et al., 2005). Patients with local or regional disease when diagnosed have a five-year relative survival rate approaching 100% (Jemal et al., 2006).

The current guidelines for prostate cancer screening, according to the American Cancer Society, advises testing for elevated PSA and digital rectal examination annually beginning at age 50. For men at high risk of developing prostate cancer (African American men and men with one or more first degree relatives diagnosed at an early age), screening should begin at age 45. Positive findings on either of these exams are confirmed by prostate biopsy. The advent of PSA screening has changed the landscape of prostate cancer diagnosis. Incidence rates in prostate cancer have increased dramatically in the last 20 years, while diagnosis in males older than 65 has levelled off. PSA testing suffers from two disadvantages. The first is its low specificity as PSA is elevated in a number of benign conditions in addition to prostate cancer. This results in a large number of prostate biopsies being conducted in men who do not have prostate cancer. The second disadvantage is that despite the relatively high sensitivity of PSA, there are men who harbor prostate cancer in the absence of elevated PSA (>4 ng/ml) (Thompson et al., 2004). It has also been estimated that up to 10% of prostate biopsies under current guidelines are falsely negative, resulting in decreased sensitivity even with biopsy (Djavan et al., 2000; Mian et al., 2002; Gupta et al., 2005; Hanley et al., 2006). Improved tests with increased specificity and sensitivity are clearly needed.

Multifactorial approach. Cancer diagnostics has traditionally relied upon the detection of single molecular markers (e.g., gene mutations, elevated PSA levels). Unfortunately, cancer is a disease state in which single markers have typically failed to detect or differentiate many forms of the disease. Thus, assays that recognize only a single marker have been shown to be of limited predictive value. A fundamental aspect of this invention is that methylation-based cancer diagnostics and the screening, diagnosis, and therapeutic monitoring of such diseases will provide significant improvements over the state-of-the-art that uses single marker analyses by the use of a selection of multiple markers. The multiplexed analytical approach is particularly well suited for cancer diagnostics since cancer is not a simple disease, this multi-factorial "panel" approach is consistent with the heterogeneous nature of cancer, both cytologically and clinically.

Key to the successful implementation of a panel approach to methylation based diagnostic tests is the design and development of optimized panels of markers that can characterize and distinguish disease states. The present invention describes a plurality of particularly efficient and unique panels of genes, the methylation analysis of one or a combination of the members of the panel enabling the detection of colon cell proliferative disorders with a particularly high sensitivity, specificity and/or predictive value.

Development of medical tests. Two key evaluative measures of any medical screening or diagnostic test are its sensitivity and specificity, which measure how well the test performs to accurately detect all affected individuals without exception, and without falsely including individuals who do not have the target disease (predictive value). Historically, many diagnostic tests have been criticized due to poor sensitivity and specificity.

A true positive (TP) result is where the test is positive and the condition is present. A false positive (FP) result is where the test is positive but the condition is not present. A true negative (TN) result is where the test is negative and the condition is not present. A false negative (FN) result is where the test is negative but the condition is not present. In this context: Sensitivity=TP/(TP+FN); Specificity=TN/(FP+TN); and Predictive value=TP/(TP+FP).

Sensitivity is a measure of a test's ability to correctly detect the target disease in an individual being tested. A test having poor sensitivity produces a high rate of false negatives, i.e., individuals who have the disease but are falsely identified as being free of that particular disease. The potential danger of a false negative is that the diseased individual will remain undiagnosed and untreated for some period of time, during which the disease may progress to a later stage wherein treatments, if any, may be less effective. An example of a test that has low sensitivity is a protein-based blood test for HIV. This type of test exhibits poor sensitivity because it fails to detect the presence of the virus until the disease is well established and the virus has invaded the bloodstream in substantial numbers. In contrast, an example of a test that has high sensitivity is viral-load detection using the polymerase chain reaction (PCR). High sensitivity is achieved because this type of test can detect very small quantities of the virus. High sensitivity is particularly important when the consequences of missing a diagnosis are high.

Specificity, on the other hand, is a measure of a test's ability to identify accurately patients who are free of the disease state. A test having poor specificity produces a high rate of false positives, i.e., individuals who are falsely identified as having the disease. A drawback of false positives is that they force patients to undergo unnecessary medical procedures treatments with their attendant risks, emotional and financial stresses, and which could have adverse effects on the patient's health. A feature of diseases which makes it difficult to develop diagnostic tests with high specificity is that disease mechanisms, particularly in cancer, often involve a plurality of genes and proteins. Additionally, certain proteins may be elevated for reasons unrelated to a disease state; an example of a test that has high specificity is a gene-based test that can detect a p53 mutation. Specificity is important when the cost or risk associated with further diagnostic procedures or further medical interventions are very high.

SUMMARY OF THE INVENTION

Figure 1:
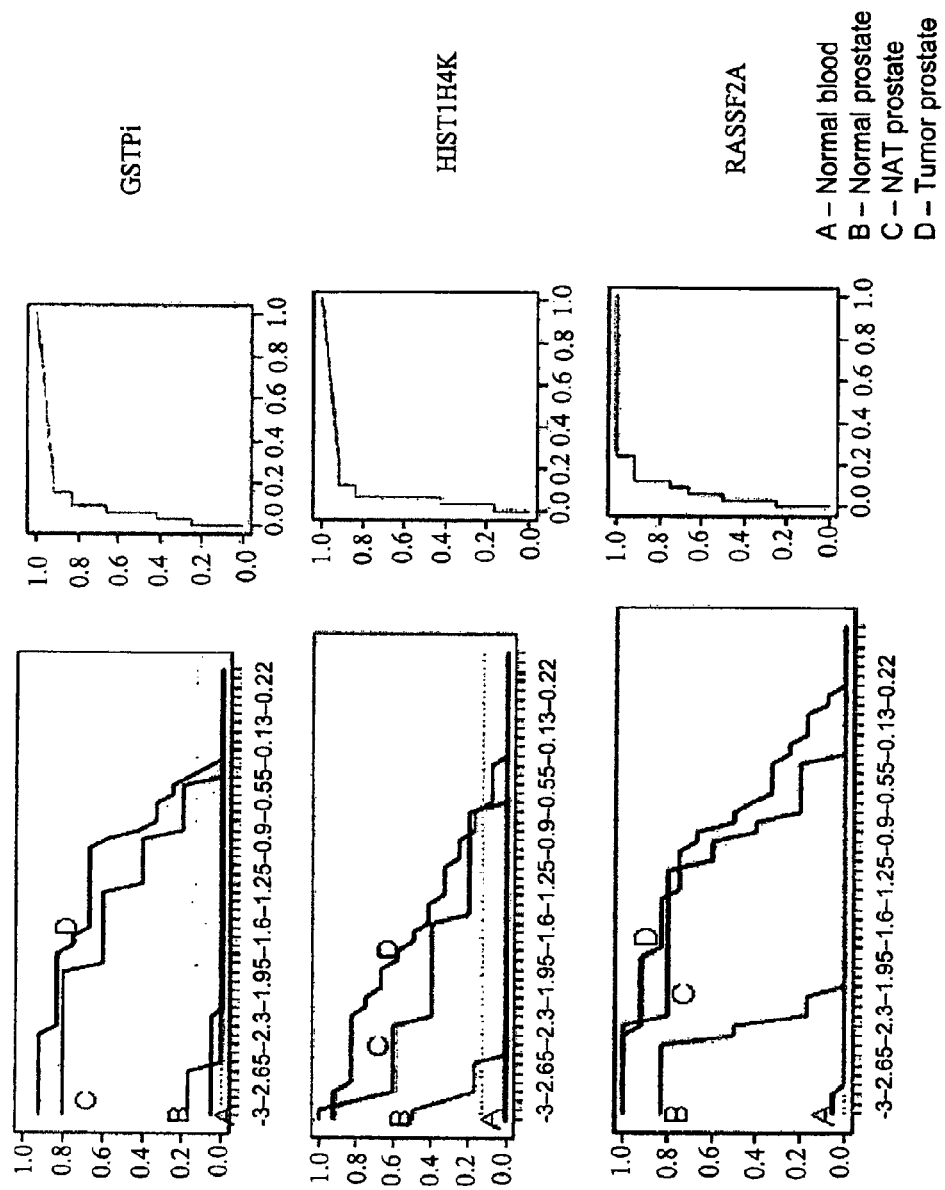
FIG. 1 provides an overview of the log mean methylation measured by means of the HM assay according to Example 1. For each analysed gene (as labeled to the left of the figures), two plots are provided, the left hand side plots provide the multiclass analysis, sensitivity is shown on the Y-axis, DNA methylation measured in (log 10 ng/mL) is shown on the X-axis. The right hand plot provides an ROC wherein sensitivity is shown on the Y-axis and 1-specificity is shown on the X-axis.

The present invention provides a method for detecting prostate cell proliferative disorders, most preferably, prostate carcinoma in a subject comprising determining the expression levels of at least one gene selected from the group consisting of RASSF2A; TFAP2E; HIST1H4K & GSTPi in a biological sample isolated from said subject wherein underexpression and/or CpG methylation is indicative of the presence of said disorder.

Preferably a plurality of genes (herein also referred to as a "gene panel") is analysed. Preferably 2, 3 or 4 genes are analysed. In one embodiment of the method said panel comprises at least one gene selected from the group consisting of RASSF2A; TFAP2E; HIST1H4K & GSTPi and/or their promotor or regulatory regions. Preferably said group comprises the gene HIST1H4K.

Particularly preferred are the following combinations of genes:
HIST1H4K+RASSF
HIST1H4K+GSTPi Various aspects of the present invention provide an efficient and unique genetic marker, whereby expression analysis of said marker enables the detection of prostate cell proliferative disorders, most preferably, prostate carcinoma with a particularly high sensitivity, specificity and/or predictive value.

In one embodiment the invention provides a method for detecting prostate cell proliferative disorders, most preferably, prostate carcinoma in a subject comprising determining the expression levels of at least one gene selected from the group consisting of RASSF2A; TFAP2E; HIST1H4K & GSTPi in a biological sample isolated from said subject wherein under-expression and/or CpG methylation is indicative of the presence of said disorder. In one embodiment said expression level is determined by detecting the presence, absence or level of mRNA transcribed from said gene. In a further embodiment said expression level is determined by detecting the presence, absence or level of a polypeptide encoded by said gene or sequence thereof.

In a further preferred embodiment said expression is determined by detecting the presence or absence of CpG methylation within said gene, wherein the presence of methylation indicates the presence of prostate cell proliferative disorders, more specifically, prostate carcinoma. Said method comprises the following steps: i) contacting genomic DNA isolated from a biological sample (preferably selected from the group consisting of ejaculate, blood plasma, blood serum, whole blood, isolated blood cells, cells isolated from the blood) obtained from the subject with at least one reagent, or series of reagents that distinguishes between methylated and non-methylated CpG dinucleotides within at least one and more preferably a plurality of target regions of the genomic DNA, wherein the nucleotide sequence of said target region comprises at least one CpG dinucleotide sequence of at least one gene selected from the group consisting of RASSF2A; TFAP2E; HIST1H4K & GSTPi; and ii) detecting carcinoma, at least in part.

Preferably a plurality of genes (herein also referred to as a "gene panel") is analysed. Preferably 2, 3 or 4 genes are analysed. In one embodiment of the method said panel comprises at least one gene selected from the group consisting of RASSF2A; TFAP2E; HIST1H4K & GSTPi and/or their promotor or regulatory regions. Preferably said group comprises the gene HIST1H4K.

Particularly preferred are the following combinations of genes:
HIST1H4K+RASSF
HIST1H4K+GSTPi Preferably the target region comprises, or hybridizes under stringent conditions to a sequence of at least 16, 50, 100 or 500 contiguous nucleotides of at least one sequence selected from the group consisting of SEQ ID NO: 1 to SEQ ID NO: 4.

Said use of the gene may be enabled by means of any analysis of the expression of the gene, by means of mRNA expression analysis or protein expression analysis. However, in the most preferred embodiment of the invention the detection of detecting prostate cell proliferative disorders, most preferably, prostate carcinomas is enabled by means of analysis of the methylation status of at least one gene selected from the group consisting of RASSF2A; TFAP2E; HIST1H4K & GSTPi, and/or its promoter or regulatory elements.

Preferably a plurality of genes (herein also referred to as a "gene panel") is analysed. Preferably 2, 3 or 4 genes are analysed. In one embodiment of the method said panel comprises at least one gene selected from the group consisting of RASSF2A; TFAP2E; HIST1H4K & GSTPi and/or their promotor or regulatory regions. Preferably said group comprises the gene HIST1H4K.

Particularly preferred are the following combinations of genes:

HIST1H4K+RASSF
HIST1H4K+GSTPi

The invention provides a method for the analysis of biological samples for features associated with the development of cancer, the method characterized in that the nucleic acid, or a fragment thereof of at least one sequence selected from the group consisting of SEQ ID NO: 1 to SEQ ID NO: 4 is contacted with a reagent or series of reagents capable of distinguishing between methylated and non-methylated CpG dinucleotides within the genomic sequence. The present invention provides a method for ascertaining epigenetic parameters of genomic DNA associated with the development of prostate cancer. The method has utility for the improved detection and diagnosis of said disease.

Preferably, the source of the test sample is selected from the group consisting of cells or cell lines, histological slides, biopsies, paraffin-embedded tissue, body fluids, ejaculate, ejaculate, urine, blood, and combinations thereof. More preferably, the source is selected from the group consisting of ejaculate, urine, blood plasma, blood serum, whole blood, isolated blood cells, cells isolated from the blood obtained from the subject.

Specifically, the present invention provides a method for detecting prostate cancer suitable for use in a diagnostic tool, comprising: obtaining a biological sample comprising genomic nucleic acid(s); contacting the nucleic acid(s), or a fragment thereof, with a reagent or a plurality of reagents sufficient for distinguishing between methylated and non-methylated CpG dinucleotide sequences within at least one and more preferably a plurality of target sequence(s) of the subject nucleic acid, wherein each of said target sequences comprises, or hybridises under stringent conditions to, a sequence comprising at least 16, 50, 100 or 500 contiguous nucleotides of a sequence selected from the group consisting of SEQ ID NO: 1 to SEQ ID NO: 4, said contiguous nucleotides comprising at least one CpG dinucleotide sequence; and determining, based at least in part on said distinguishing, the methylation state of at least one and more preferably a plurality of target CpG dinucleotide sequence, or an average, or a value reflecting an average methylation state of a plurality of target CpG dinucleotide sequences.

Preferably, distinguishing between methylated and non-methylated CpG dinucleotide sequences within the target sequence comprises methylation state-dependent conversion or non-conversion of at least one such CpG dinucleotide sequence to the corresponding converted or non-converted dinucleotide sequence within a sequence selected from the group consisting of SEQ ID NO: 5 to SEQ ID NO: 20, and contiguous regions thereof corresponding to the target sequence.

Additional embodiments provide a method for the detection of detecting prostate cell proliferative disorders, most preferably, prostate cancer comprising: obtaining a biological sample having subject genomic DNA; extracting the genomic DNA; treating the genomic DNA, or a fragment thereof, with one or more reagents to convert 5-position unmethylated cytosine bases to uracil or to another base that is detectably dissimilar to cytosine in terms of hybridization properties; contacting the treated genomic DNA, or the treated fragment thereof, with an amplification enzyme and at least two primers comprising, in each case a contiguous sequence at least 9 nucleotides in length that is complementary to, or hybridizes under moderately stringent or stringent conditions to a sequence selected from the group consisting SEQ ID NO: 5 to SEQ ID NO: 20, and complements thereof, wherein the treated DNA or the fragment thereof is either amplified to produce an amplificate, or is not amplified; and determining, based on a presence or absence of, or on a property of said amplificate, the methylation state or an average, or a value reflecting an average of the methylation level of at least one, but more preferably a plurality of CpG dinucleotides of a sequence selected from the group consisting of SEQ ID NO: 1 to SEQ ID NO: 4.

Preferably, determining comprises use of at least one method selected from the group consisting of: i) hybridizing at least one nucleic acid molecule comprising a contiguous sequence at least 9 nucleotides in length that is complementary to, or hybridizes under moderately stringent or stringent conditions to a sequence selected from the group consisting of SEQ ID NO: 5 to SEQ ID NO: 20, and complements thereof; ii) hybridizing at least one nucleic acid molecule, bound to a solid phase, comprising a contiguous sequence at least 9 nucleotides in length that is complementary to, or hybridizes under moderately stringent or stringent conditions to a sequence selected from the group consisting of SEQ ID NO: 5 to SEQ ID NO: 20, and complements thereof; iii) hybridizing at least one nucleic acid molecule comprising a contiguous sequence at least 9 nucleotides in length that is complementary to, or hybridizes under moderately stringent or stringent conditions to a sequence selected from the group consisting of SEQ ID NO: 5 to SEQ ID NO: 20, and complements thereof, and extending at least one such hybridized nucleic acid molecule by at least one nucleotide base; and iv) sequencing of the amplificate.

Further embodiments provide a method for the analysis (i.e. detection of classification) of carcinoma, comprising: obtaining a biological sample having subject genomic DNA; extracting the genomic DNA; contacting the genomic DNA, or a fragment thereof, comprising one or more sequences selected from the group consisting of SEQ ID NO: 1 to SEQ ID NO: 4 or a sequence that hybridizes under stringent conditions thereto, with one or more methylation-sensitive restriction enzymes, wherein the genomic DNA is either digested thereby to produce digestion fragments, or is not digested thereby; and determining, based on a presence or absence of, or on property of at least one such fragment, the methylation state of at least one CpG dinucleotide sequence at least one sequence selected from the group consisting of SEQ ID NO: 1 to SEQ ID NO: 4, or an average, or a value reflecting an average methylation state of a plurality of CpG dinucleotide sequences thereof. Preferably, the digested or undigested genomic DNA is amplified prior to said determining. Additional embodiments provide novel genomic and chemically modified nucleic acid sequences, as well as oligonucleotides and/or PNA-oligomers for analysis of cytosine methylation patterns within sequences from the group consisting of SEQ ID NO: 1 to SEQ ID NO: 4.

DETAILED DESCRIPTION OF THE INVENTION

Definitions

The term "Observed/Expected Ratio" ("O/E Ratio") refers to the frequency of CpG dinucleotides within a particular DNA sequence, and corresponds to the [number of CpG sites/(number of C bases×number of G bases)]/band length for each fragment.

The term "CpG island" refers to a contiguous region of genomic DNA that satisfies the criteria of (1) having a frequency of CpG dinucleotides corresponding to an "Observed/Expected Ratio">0.6, and (2) having a "GC Content">0.5. CpG islands are typically, but not always, between about 0.2 to about 1 KB, or to about 2 kb in length. The term "methylation state" or "methylation status" refers to the presence or absence of 5-methylcytosine ("5-mCyt") at one or a plurality of CpG dinucleotides within a DNA sequence. Methylation states at one or more particular CpG methylation sites (each having two CpG dinucleotide sequences) within a DNA sequence include "unmethylated," "fully-methylated" and "hemi-methylated."

The term "hemi-methylation" or "hemimethylation" refers to the methylation state of a double stranded DNA wherein only one strand thereof is methylated.

The term 'AUC' as used herein is an abbreviation for the area under a curve. In particular it refers to the area under a Receiver Operating Characteristic (ROC) curve. The ROC curve is a plot of the true positive rate against the false positive rate for the different possible cut points of a diagnostic test. It shows the trade-off between sensitivity and specificity depending on the selected cut point (any increase in sensitivity will be accompanied by a decrease in specificity). The area under an ROC curve (AUC) is a measure for the accuracy of a diagnostic test (the larger the area the better, optimum is 1, a random test would have a ROC curve lying on the diagonal with an area of 0.5; for reference: J. P. Egan. Signal Detection Theory and ROC Analysis, Academic Press, New York, 1975).

The term "hypermethylation" refers to the average methylation state corresponding to an increased presence of 5-mCyt at one or a plurality of CpG dinucleotides within a DNA sequence of a test DNA sample, relative to the amount of 5-mCyt found at corresponding CpG dinucleotides within a normal control DNA sample.

The term "hypomethylation" refers to the average methylation state corresponding to a decreased presence of 5-mCyt at one or a plurality of CpG dinucleotides within a DNA sequence of a test DNA sample, relative to the amount of 5-mCyt found at corresponding CpG dinucleotides within a normal control DNA sample.

The term "microarray" refers broadly to both "DNA microarrays," and 'DNA chip(s),' as recognized in the art, encompasses all art-recognized solid supports, and encompasses all methods for affixing nucleic acid molecules thereto or synthesis of nucleic acids thereon. "Genetic parameters" are mutations and polymorphisms of genes and sequences further required for their regulation. To be designated as mutations are, in particular, insertions, deletions, point mutations, inversions and polymorphisms and, particularly preferred, SNPs (single nucleotide polymorphisms).

"Epigenetic parameters" are, in particular, cytosine methylation. Further epigenetic parameters include, for example, the acetylation of histones which, however, cannot be directly analysed using the described method but which, in turn, correlates with the DNA methylation.

The term "bisulfite reagent" refers to a reagent comprising bisulfite, disulfite, hydrogen sulfite or combinations thereof, useful as disclosed herein to distinguish between methylated and unmethylated CpG dinucleotide sequences.

The term "Methylation assay" refers to any assay for determining the methylation state of one or more CpG dinucleotide sequences within a sequence of DNA.

The term "MS.AP-PCR" (Methylation-Sensitive Arbitrarily-Primed Polymerase Chain Reaction) refers to the art-recognized technology that allows for a global scan of the genome using CG-rich primers to focus on the regions most likely to contain CpG dinucleotides, and described by Gonzalgo et al., Cancer Research 57:594-599, 1997.

The term "MethyLight™" refers to the art-recognized fluorescence-based real-time PCR technique described by Eads et al., Cancer Res. 59:2302-2306, 1999.

The term "HeavyMethyl™" assay, in the embodiment thereof implemented herein, refers to an assay, wherein methylation specific blocking probes (also referred to herein as blockers) covering CpG positions between, or covered by the amplification primers enable methylation-specific selective amplification of a nucleic acid sample.

The term "HeavyMethyl™ MethyLight™" assay, in the embodiment thereof implemented herein, refers to a HeavyMethyl™ MethyLight™ assay, which is a variation of the MethyLight™ assay, wherein the MethyLight™ assay is combined with methylation specific blocking probes covering CpG positions between the amplification primers.

The term "Ms-SNuPE" (Methylation-sensitive Single Nucleotide Primer Extension) refers to the art-recognized assay described by Gonzalgo & Jones, Nucleic Acids Res. 25:2529-2531, 1997.

The term "MSP" (Methylation-specific PCR) refers to the art-recognized methylation assay described by Herman et al. Proc. Natl. Acad. Sci. USA 93:9821-9826, 1996, and by U.S. Pat. No. 5,786,146.

The term "COBRA" (Combined Bisulfite Restriction Analysis) refers to the art-recognized methylation assay described by Xiong & Laird, Nucleic Acids Res. 25:2532-2534, 1997. The term "MCA" (Methylated CpG Island Amplification) refers to the methylation assay described by Toyota et al., Cancer Res. 59:2307-12, 1999, and in WO 00/26401A1. The term "hybridisation" is to be understood as a bond of an oligonucleotide to a complementary sequence along the lines of the Watson-Crick base pairings in the sample DNA, forming a duplex structure.

"Stringent hybridisation conditions," as defined herein, involve hybridising at 68° C. in 5×SSC/5×Denhardt's solution/11.0% SDS, and washing in 0.2×SSC/0.1% SDS at room temperature, or involve the art-recognized equivalent thereof (e.g., conditions in which a hybridisation is carried out at 60° C. in 2.5×SSC buffer, followed by several washing steps at 37° C. in a low buffer concentration, and remains stable). Moderately stringent conditions, as defined herein, involve including washing in 3×SSC at 42° C., or the art-recognized equivalent thereof. The parameters of salt concentration and temperature can be varied to achieve the optimal level of identity between the probe and the target nucleic acid. Guidance regarding such conditions is available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.) at Unit 2.10.

The terms "Methylation-specific restriction enzymes" or "methylation-sensitive restriction enzymes" shall be taken to mean an enzyme that selectively digests a nucleic acid dependent on the methylation state of its recognition site. In the case of such restriction enzymes which specifically cut if the recognition site is not methylated or hemimethylated, the cut will not take place, or with a significantly reduced efficiency, if the recognition site is methylated. In the case of such restriction enzymes which specifically cut if the recognition site is methylated, the cut will not take place, or with a significantly reduced efficiency if the recognition site is not methylated. Preferred are methylation-specific restriction enzymes, the recognition sequence of which contains a CG dinucleotide (for instance cgcg or cccggg). Further preferred for some embodiments are restriction enzymes that do not cut if the cytosine in this dinucleotide is methylated at the carbon atom C5.

"Non-methylation-specific restriction enzymes" or "non-methylation-sensitive restriction enzymes" are restriction enzymes that cut a nucleic acid sequence irrespective of the methylation state with nearly identical efficiency. They are also called "methylation-unspecific restriction enzymes."

In reference to composite array sequences, the phrase "contiguous nucleotides" refers to a contiguous sequence region of any individual contiguous sequence of the composite array, but does not include a region of the composite array sequence that includes a "node," as defined herein above.

The terms "RASSF2A; TFAP2E; HIST1H4K & GSTPi" shall be taken to include all transcript variants thereof and all promoter and regulatory elements thereof. Furthermore as a plurality of SNPs are known within said gene the term shall be taken to include all sequence variants thereof.

Overview:

The present invention provides a method for detecting carcinoma in a subject comprising determining the expression levels of at least one gene selected from the group consisting of RASSF2A; TFAP2E; HIST1H4K & GSTPi in a biological sample isolated from said subject wherein underexpression and/or CpG methylation is indicative of the presence or class of said disorder. Said markers may be used for the diagnosis of prostate cancer including early detection during the pre-cancerous stages of the disease. The markers of the present invention are particularly efficient in detecting malignant prostate cell proliferative disorders such as prostate carcinoma, thereby providing improved means for the early detection, classification and treatment of said disorders.

In addition to the embodiments above wherein the methylation analysis of at least one gene selected from the group consisting of RASSF2A; TFAP2E; HIST1H4K & GSTPi is analysed, the invention presents further panels of genes comprising at least one gene selected from the group consisting of RASSF2A; TFAP2E; HIST1H4K & GSTPi with novel utility for the detection of cell proliferative disorders, in particular prostate cancer. Preferably a plurality of genes (herein also referred to as a "gene panel") is analysed. Preferably 2, 3 or 4 genes are analysed. In one embodiment of the method said panel comprises at least one gene selected from the group consisting of RASSF2A; TFAP2E; HIST1H4K & GSTPi and/or their promotor or regulatory regions. Preferably said group comprises the gene HIST1H4K. Particularly preferred are the following combinations of genes:

HIST1H4K+RASSF
HIST1H4K+GSTPi

Bisulfite modification of DNA is an art-recognized tool used to assess CpG methylation status. 5-methylcytosine is the most frequent covalent base modification in the DNA of eukaryotic cells. It plays a role, for example, in the regulation of the transcription, in genetic imprinting, and in tumorigenesis. Therefore, the identification of 5-methylcytosine as a component of genetic information is of considerable interest. However, 5-methylcytosine positions cannot be identified by sequencing, because 5-methylcytosine has the same base pairing behavior as cytosine. Moreover, the epigenetic information carried by 5-methylcytosine is completely lost during, e.g., PCR amplification.

The most frequently used method for analyzing DNA for the presence of 5-methylcytosine is based upon the specific reaction of bisulfite with cytosine whereby, upon subsequent alkaline hydrolysis, cytosine is converted to uracil which corresponds to thymine in its base pairing behavior. Significantly, however, 5-methylcytosine remains unmodified under these conditions. Consequently, the original DNA is converted in such a manner that methylcytosine, which originally could not be distinguished from cytosine by its hybridization behavior, can now be detected as the only remaining cytosine using standard, art-recognized molecular biological techniques, for example, by amplification and hybridization, or by sequencing. All of these techniques are based on differential base pairing properties, which can now be fully exploited.

The prior art, in terms of sensitivity, is defined by a method comprising enclosing the DNA to be analysed in an agarose matrix, thereby preventing the diffusion and renaturation of the DNA (bisulfite only reacts with single-stranded DNA), and replacing all precipitation and purification steps with fast dialysis (Olek A, et al., A modified and improved method for bisulfite based cytosine methylation analysis, Nucleic Acids Res. 24:5064-6, 1996). It is thus possible to analyse individual cells for methylation status, illustrating the utility and sensitivity of the method. An overview of art-recognized methods for detecting 5-methylcytosine is provided by Rein, T., et al., Nucleic Acids Res., 26:2255, 1998.

The bisulfite technique, barring few exceptions (e.g., Zeschnigk M, et al., Eur J Hum Genet. 5:94-98, 1997), is currently only used in research. In all instances, short, specific fragments of a known gene are amplified subsequent to a bisulfite treatment, and either completely sequenced (Olek & Walter, Nat. Genet. 1997 17:275-6, 1997), subjected to one or more primer extension reactions (Gonzalgo & Jones, Nucleic Acids Res., 25:2529-31, 1997; WO 95/00669; U.S. Pat. No. 6,251,594) to analyse individual cytosine positions, or treated by enzymatic digestion (Xiong & Laird, Nucleic Acids Res., 25:2532-4, 1997). Detection by hybridisation has also been described in the art (Olek et al., WO 99/28498). Additionally, use of the bisulfite technique for methylation detection with respect to individual genes has been described (Grigg & Clark, Bioessays, 16:431-6, 1994; Zeschnigk M, et al., Hum Mol Genet., 6:387-95, 1997; Feil R, et al., Nucleic Acids Res., 22:695-, 1994; Martin V, et al., Gene, 157:261-4, 1995; WO 9746705 and WO 9515373).

The present invention provides for the use of the bisulfite technique, in combination with one or more methylation assays, for determination of the methylation status of CpG dinucleotide sequences within SEQ ID NO: 1 to SEQ ID NO: 4. Genomic CpG dinucleotides can be methylated or unmethylated (alternatively known as up- and down-methylated respectively). However the methods of the present invention are suitable for the analysis of biological samples of a heterogeneous nature e.g. a low concentration of tumor cells within a background of blood or ejaculate. Accordingly, when analyzing the methylation status of a CpG position within such a sample the person skilled in the art may use a quantitative assay for determining the level (e.g. percent, fraction, ratio, proportion or degree) of methylation at a particular CpG position as opposed to a methylation state. Accordingly the term methylation status or methylation state should also be taken to mean a value reflecting the degree of methylation at a CpG position. Unless specifically stated the terms "hypermethylated" or "upmethylated" shall be taken to mean a methylation level above that of a specified cut-off point, wherein said cut-off may be a value representing the average or median methylation level for a given population, or is preferably an optimized cut-off level. The "cut-off" is also referred herein as a "threshold". In the context of the present invention the terms "methylated", "hypermethylated" or "upmethylated" shall be taken to include a methylation level above the cut-off be zero (0) % (or equivalents thereof) methylation for all CpG positions within and associated with (e.g. in promoter or regulatory regions) the genes RASSF2A; TFAP2E; HIST1H4K & GSTPi.

Preferably a plurality of genes (herein also referred to as a "gene panel") is analysed. Preferably 2, 3 or 4 genes are analysed. In one embodiment of the method said panel comprises at least one gene selected from the group consisting of RASSF2A; TFAP2E; HIST1H4K & GSTPi and/or their promotor or regulatory regions. Preferably said group comprises the gene HIST1H4K.

Particularly preferred are the following combinations of genes:
HIST1H4K+RASSF
HIST1H4K+GSTPi According to the present invention, determination of the methylation status of CpG dinucleotide sequences within SEQ ID NO: 1 to SEQ ID NO: 4 has utility in the diagnosis of prostate cancer.

Methylation Assay Procedures. Various methylation assay procedures are known in the art, and can be used in conjunction with the present invention. These assays allow for determination of the methylation state of one or a plurality of CpG dinucleotides (e.g., CpG islands) within a DNA sequence. Such assays involve, among other techniques, DNA sequencing of bisulfite-treated DNA, PCR (for sequence-specific amplification), Southern blot analysis, and use of methylation-sensitive restriction enzymes.

For example, genomic sequencing has been simplified for analysis of DNA methylation patterns and 5-methylcytosine distribution by using bisulfite treatment (Frommer et al., Proc. Natl. Acad. Sci. USA 89:1827-1831, 1992). Additionally, restriction enzyme digestion of PCR products amplified from bisulfite-converted DNA is used, e.g., the method described by Sadri & Hornsby (Nucl. Acids Res. 24:5058-5059, 1996), or COBRA (Combined Bisulfite Restriction Analysis) (Xiong & Laird, Nucleic Acids Res. 25:2532-2534, 1997).

COBRA. COBRA™ analysis is a quantitative methylation assay useful for determining DNA methylation levels at specific gene loci in small amounts of genomic DNA (Xiong & Laird, Nucleic Acids Res. 25:2532-2534, 1997). Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (Proc. Natl. Acad. Sci. USA 89:1827-1831, 1992). PCR amplification of the bisulfite converted DNA is then performed using primers specific for the CpG islands of interest, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from microdissected paraffin-embedded tissue samples.

Typical reagents (e.g., as might be found in a typical COBRA™-based kit) for COBRA™ analysis may include, but are not limited to: PCR primers for specific gene (or bisulfite treated DNA sequence or CpG island); restriction enzyme and appropriate buffer; gene-hybridization oligonucleotide; control hybridization oligonucleotide; kinase labeling kit for oligonucleotide probe; and labeled nucleotides. Additionally, bisulfite conversion reagents may include: DNA denaturation buffer; sulfonation buffer; DNA recovery reagents or kits (e.g., precipitation, ultrafiltration, affinity column); desulfonation buffer; and DNA recovery components.

Preferably, assays such as "MethyLight™" (a fluorescence-based real-time PCR technique) (Eads et al., Cancer Res. 59:2302-2306, 1999), Ms-SNuPE™ (Methylation-sensitive Single Nucleotide Primer Extension) reactions (Gonzalgo & Jones, Nucleic Acids Res. 25:2529-2531, 1997), methylation-specific PCR ("MSP"; Herman et al., Proc. Natl. Acad. Sci. USA 93:9821-9826, 1996; U.S. Pat. No. 5,786,146), and methylated CpG island amplification ("MCA"; Toyota et al., Cancer Res. 59:2307-12, 1999) are used alone or in combination with other of these methods.

The "HeavyMethyl™" assay, technique is a quantitative method for assessing methylation differences based on methylation specific amplification of bisulfite treated DNA. Methylation specific blocking probes (also referred to herein as blockers) covering CpG positions between, or covered by the amplification primers enable methylation-specific selective amplification of a nucleic acid sample.

The term "HeavyMethyl™ MethyLight™" assay, in the embodiment thereof implemented herein, refers to a HeavyMethyl™ MethyLight™ assay, which is a variation of the MethyLight™ assay, wherein the MethyLight™ assay is combined with methylation specific blocking probes covering CpG positions between the amplification primers. The HeavyMethyl™ assay may also be used in combination with methylation specific amplification primers.

Typical reagents (e.g., as might be found in a typical MethyLight☐-based kit) for HeavyMethyl™ analysis may include, but are not limited to: PCR primers for specific genes (or bisulfite treated DNA sequence or CpG island); blocking oligonucleotides; optimized PCR buffers and deoxynucleotides; and Taq polymerase.

MSP. MSP (methylation-specific PCR) allows for assessing the methylation status of virtually any group of CpG sites within a CpG island, independent of the use of methylation-sensitive restriction enzymes (Herman et al. Proc. Natl. Acad. Sci. USA 93:9821-9826, 1996; U.S. Pat. No. 5,786,146). Briefly, DNA is modified by sodium bisulfite converting all unmethylated, but not methylated cytosines to uracil, and subsequently amplified with primers specific for methylated versus unmethylated DNA. MSP requires only small quantities of DNA, is sensitive to 0.1% methylated alleles of a given CpG island locus, and can be performed on DNA extracted from paraffin-embedded samples. Typical reagents (e.g., as might be found in a typical MSP-based kit) for MSP analysis may include, but are not limited to: methylated and unmethylated PCR primers for specific gene (or bisulfite treated DNA sequence or CpG island), optimized PCR buffers and deoxynucleotides, and specific probes.

MethyLight™. The MethyLight™ assay is a high-throughput quantitative methylation assay that utilizes fluorescence-based real-time PCR (TaqMan☐) technology that requires no further manipulations after the PCR step (Eads et al., Cancer Res. 59:2302-2306, 1999). Briefly, the MethyLight™ process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed in a "biased" (with PCR primers that overlap known CpG dinucleotides) reaction. Sequence discrimination can occur both at the level of the amplification process and at the level of the fluorescence detection process.

The MethyLight™ assay may be used as a quantitative test for methylation patterns in the genomic DNA sample, wherein sequence discrimination occurs at the level of probe hybridization. In this quantitative version, the PCR reaction provides for a methylation specific amplification in the presence of a fluorescent probe that overlaps a particular putative methylation site. An unbiased control for the amount of input DNA is provided by a reaction in which neither the primers, nor the probe overlie any CpG dinucleotides. Alternatively, a qualitative test for genomic methylation is achieved by probing of the biased PCR pool with either control oligonucleotides that do not "cover" known methylation sites (a fluorescence-based version of the HeavyMethyl™ and MSP techniques), or with oligonucleotides covering potential methylation sites.

The MethyLight™ process can be used with any suitable probes e.g. "TaqMan®", Lightcycler® etc. . . . For example, double-stranded genomic DNA is treated with sodium bisulfite and subjected to one of two sets of PCR reactions using TaqMan® probes; e.g., with MSP primers and/or HeavyMethyl blocker oligonucleotides and TaqMan® probe. The TaqMan® probe is dual-labeled with fluorescent "reporter" and "quencher" molecules, and is designed to be specific for a relatively high GC content region so that it melts out at about 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system.

Typical reagents (e.g., as might be found in a typical MethyLight☒-based kit) for MethyLight™ analysis may include, but are not limited to: PCR primers for specific gene (or bisulfite treated DNA sequence or CpG island); TaqMan® or Lightcycler® probes; optimized PCR buffers and deoxynucleotides; and Taq polymerase.

The QM™ (quantitative methylation) assay is an alternative quantitative test for methylation patterns in genomic DNA samples, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe overlie any CpG dinucleotides. Alternatively, a qualitative test for genomic methylation is achieved by probing of the biased PCR pool with either control oligonucleotides that do not "cover" known methylation sites (a fluorescence-based version of the HeavyMethyl™ and MSP techniques), or with oligonucleotides covering potential methylation sites.

The QM™ process can be used with any suitable probes e.g. "TaqMan®", Lightcycler® etc. . . . in the amplification process. For example, double-stranded genomic DNA is treated with sodium bisulfite and subjected to unbiased primers and the TaqMan® probe. The TaqMan® probe is dual-labeled with fluorescent "reporter" and "quencher" molecules, and is designed to be specific for a relatively high GC content region so that it melts out at about 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system.

Typical reagents (e.g., as might be found in a typical QM™-based kit) for QM™ analysis may include, but are not limited to: PCR primers for specific gene (or bisulfite treated DNA sequence or CpG island); TaqMan® or Lightcycler® probes; optimized PCR buffers and deoxynucleotides; and Taq polymerase.

Ms-SNuPE. The Ms-SNuPE™ technique is a quantitative method for assessing methylation differences at specific CpG sites based on bisulfite treatment of DNA, followed by single-nucleotide primer extension (Gonzalgo & Jones, Nucleic Acids Res. 25:2529-2531, 1997). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest. Small amounts of DNA can be analysed (e.g., microdissected pathology sections), and it avoids utilization of restriction enzymes for determining the methylation status at CpG sites.

Typical reagents (e.g., as might be found in a typical Ms-SNuPE™-based kit) for Ms-SNuPE™ analysis may include, but are not limited to: PCR primers for specific gene (or bisulfite treated DNA sequence or CpG island); optimized PCR buffers and deoxynucleotides; gel extraction kit; positive control primers; Ms-SNuPE™ primers for specific gene; reaction buffer (for the Ms-SNuPE reaction); and labelled nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

The Genomic Sequences According to SEQ ID NO: 1 TO SEQ ID NO: 4, and Non-naturally Occurring Treated Variants Thereof According to SEQ ID NO: 5 TO SEP ID NO: 20, were Determined to have Novel Utility for the Early Detection, Classification and/or Treatment of Cell Proliferative Disorders, in Particular Prostate carcinoma.

In one embodiment the invention of the method comprises the following steps: i) contacting genomic DNA (preferably isolated from body fluids) obtained from the subject with at least one reagent, or series of reagents that distinguishes between methylated and non-methylated CpG dinucleotides within at least one gene selected from the group consisting of RASSF2A; TFAP2E; HIST1H4K & GSTPi (including promoter and regulatory regions); and ii) detecting prostate cell proliferative disorders, most preferably, prostate carcinoma.

Preferably a plurality of genes (herein also referred to as a "gene panel") is analysed. Preferably 2, 3 or 4 genes are analysed. In one embodiment of the method said panel comprises at least one gene selected from the group consisting of RASSF2A; TFAP2E; HIST1H4K & GSTPi and/or their promotor or regulatory regions. Preferably said group comprises the gene HIST1H4K.

Particularly preferred are the following combinations of genes:

HIST1H4K+RASSF
HIST1H4K+GSTPi

Genomic DNA may be isolated by any means standard in the art, including the use of commercially available kits. Briefly, wherein the DNA of interest is encapsulated in by a cellular membrane the biological sample must be disrupted and lysed by enzymatic, chemical or mechanical means. The DNA solution may then be cleared of proteins and other contaminants, e.g., by digestion with proteinase K. The genomic DNA is then recovered from the solution. This may be carried out by means of a variety of methods including salting out, organic extraction or binding of the DNA to a solid phase support. The choice of method will be affected by several factors including time, expense and required quantity of DNA. All clinical sample types comprising neoplastic matter or pre-neoplastic matter are suitable for use in the present method, preferred are cell lines, histological slides, biopsies, paraffin-embedded tissue, body fluids, ejaculate, urine, blood plasma, blood serum, whole blood, isolated blood cells, cells isolated from the blood and combinations thereof. Body fluids are the preferred source of the DNA; particularly preferred are ejaculate, blood plasma, blood serum, whole blood, isolated blood cells and cells isolated from the blood.

The genomic DNA sample is then treated with at least one reagent, or series of reagents that distinguishes between methylated and non-methylated CpG dinucleotides within at least one and more preferably a plurality of target region(s) of the genomic DNA, wherein each target region comprises, or hybridizes under stringent conditions to a sequence of at least 16, 50, 100 or 500 contiguous nucleotides of at least one sequence selected from the group consisting of SEQ ID NO: 1 to SEQ ID NO: 4 respectively, wherein said contiguous nucleotides comprise at least one CpG dinucleotide sequence.

It is particularly preferred that said reagent converts cytosine bases which are unmethylated at the 5'-position to uracil, thymine, or another base which is dissimilar to cytosine in terms of hybridisation behaviour. However in an alternative embodiment said reagent may be a methylation sensitive restriction enzyme.

Wherein the genomic DNA sample is treated in such a manner that cytosine bases which are unmethylated at the 5'-position are converted to uracil, thymine, or another base which is dissimilar to cytosine in terms of hybridization behavior. It is preferred that this treatment is carried out with bisulfite (hydrogen sulfite, disulfite) and subsequent alkaline hydrolysis. Such a treatment results in the conversion of SEQ ID NO: 1 to SEQ ID NO: 4 to SEQ ID NO: 5 to SEQ ID NO: 12 (see Table 1) wherein said CpG dinucleotides are methylated or SEQ ID NO: 13 to SEQ ID NO: 20 wherein said CpG dinucleotides are unmethylated.

The treated DNA is then analysed in order to determine the methylation state of at least one gene selected from the group consisting of RASSF2A; TFAP2E; HIST1H4K & GSTPi prior to the treatment.

Preferably a plurality of genes (herein also referred to as a "gene panel") is analysed. Preferably 2, 3 or 4 genes are analysed. In one embodiment of the method said panel comprises at least one gene selected from the group consisting of RASSF2A; TFAP2E; HIST1H4K & GSTPi and/or their promotor or regulatory regions. Preferably said group comprises the gene HIST1H4K.

Particularly preferred are the following combinations of genes:

HIST1H4K+RASSF
HIST1H4K+GSTPi

It is particularly preferred that each target region comprises, or hybridizes under stringent conditions to at least 16, 50, 100 or 500 contiguous nucleotides of a gene selected from the group consisting of RASSF2A; TFAP2E; HIST1H4K & GSTPi. It is preferred that the sequence of said genes according to SEQ ID NO: 1 to SEQ ID NO: 4 is analysed as provided in Table 1 and the accompanying sequence listing. The method of analysis may be selected from those known in the art, including those listed herein. Particularly preferred are MethyLight™, MSP and the use of blocking oligonucleotides (HeavyMethyl™) as described herein. It is further preferred that any oligonucleotides used in such analysis (including primers, blocking oligonucleotides and detection probes) should be reverse complementary, identical, or hybridise under stringent or highly stringent conditions to an at least 16-base-pair long segment of the base sequences of one or more of SEQ ID NO: 5 to SEQ ID NO: 20 and sequences complementary thereto.

Aberrant methylation, more specifically hypermethylation of RASSF2A; TFAP2E; HIST1H4K & GSTPi (as well as promoter and/or regulatory regions thereof) is associated with the presence of prostate cell proliferative disorders, in particular, prostate cancer. Accordingly wherein a biological sample presents within any degree of methylation, said sample should be determined as being of a cell proliferative disorder, in particular cancer.

Said method may be enabled by means of any analysis of the expression of an RNA transcribed therefrom or polypeptide or protein translated from said RNA, preferably by means of mRNA expression analysis or polypeptide expression analysis. Accordingly the present invention also provides diagnostic assays and methods, both quantitative and qualitative for detecting the expression of at least one gene selected from the group consisting of RASSF2A; TFAP2E; HIST1H4K & GSTPi in a subject and determining therefrom upon the presence or absence of prostate cell proliferative disorders, most preferably, cancer in said subject.

Aberrant expression of mRNA transcribed from at least one gene selected from the group consisting of RASSF2A; TFAP2E; HIST1H4K & GSTPi is associated with the presence of prostate cell proliferative disorders, in particular, prostate cancer in a subject. According to the present invention, under expression (and/or presence methylation) is associated with the presence of cancer, and vice versa over-expression (and/or absence of methylation) is associated with the absence of cancer.

Preferably the mRNA expression of plurality of genes (herein also referred to as a "gene panel") is analysed. Preferably 2, 3 or 4 genes are analysed. In one embodiment of the method said panel comprises at least one gene selected from the group consisting of RASSF2A; TFAP2E; HIST1H4K & GSTPi and/or their promotor or regulatory regions. Preferably said group comprises the gene HIST1H4K.

Particularly preferred are the following combinations of genes:

HIST1H4K+RASSF
HIST1H4K+GSTPi

To detect the presence of mRNA encoding a gene or genomic sequence, a sample is obtained from a patient. The sample may be any suitable sample comprising cellular matter of the tumor. Suitable sample types include cell lines, histological slides, biopsies, paraffin-embedded tissue, body fluids, ejaculate, urine, blood plasma, blood serum, whole blood, isolated blood cells, cells isolated from the blood and all possible combinations thereof. It is preferred that said sample types are ejaculate or body fluids selected from the group consisting ejaculate, urine, blood plasma, blood serum, whole blood, isolated blood cells, cells isolated from the blood.

The sample may be treated to extract the RNA contained therein. The resulting nucleic acid from the sample is then analysed. Many techniques are known in the state of the art for determining absolute and relative levels of gene expression, commonly used techniques suitable for use in the present invention include in situ hybridisation (e.g. FISH), Northern analysis, RNase protection assays (RPA), microarrays and PCR-based techniques, such as quantitative PCR and differential display PCR or any other nucleic acid detection method.

Particularly preferred is the use of the reverse transcription/polymerisation chain reaction technique (RT-PCR). The method of RT-PCR is well known in the art (for example, see Watson and Fleming, supra).

The RT-PCR method can be performed as follows. Total cellular RNA is isolated by, for example, the standard guanidium isothiocyanate method and the total RNA is reverse transcribed. The reverse transcription method involves synthesis of DNA on a template of RNA using a reverse transcriptase enzyme and a 3' end oligonucleotide dT primer and/or random hexamer primers. The cDNA thus produced is then amplified by means of PCR. (Belyavsky et al, Nucl Acid Res 17:2919-2932, 1989; Krug and Berger, Methods in Enzymology, Academic Press, N.Y., Vol. 152, pp. 316-325, 1987 which are incorporated by reference). Further preferred is the "Real-time" variant of RT-PCR, wherein the PCR product is detected by means of hybridisation probes (e.g. TaqMan, Lightcycler, Molecular Beacons & Scorpion) or SYBR green. The detected signal from the probes or SYBR green is then quantitated either by reference to a standard curve or by comparing the Ct values to that of a calibration standard. Analysis of housekeeping genes is often used to normalize the results.

In Northern blot analysis total or poly(A)+ mRNA is run on a denaturing agarose gel and detected by hybridisation to a labelled probe in the dried gel itself or on a membrane. The resulting signal is proportional to the amount of target RNA in the RNA population. Comparing the signals from two or more cell populations or tissues reveals relative differences in gene expression levels. Absolute quantitation can be performed by comparing the signal to a standard curve generated using known amounts of an in vitro transcript corresponding to the target RNA. Analysis of housekeeping genes, genes whose expression levels are expected to remain relatively constant regardless of conditions, is often used to normalize the results, eliminating any apparent differences caused by unequal transfer of RNA to the membrane or unequal loading of RNA on the gel.

The first step in Northern analysis is isolating pure, intact RNA from the cells or tissue of interest. Because Northern blots distinguish RNAs by size, sample integrity influences the degree to which a signal is localized in a single band. Partially degraded RNA samples will result in the signal being smeared or distributed over several bands with an overall loss in sensitivity and possibly an erroneous interpretation of the data. In Northern blot analysis, DNA, RNA and oligonucleotide probes can be used and these probes are preferably labelled (e.g. radioactive labels, mass labels or fluorescent labels). The size of the target RNA, not the probe, will determine the size of the detected band, so a method such as random-primed labelling, which generates probes of variable lengths, are suitable for probe synthesis. The specific activity of the probe will determine the level of sensitivity, so it is preferred that probes with high specific activities, are used.

In an RNase protection assay, the RNA target and an RNA probe of a defined length are hybridised in solution. Following hybridisation, the RNA is digested with RNases specific for single-stranded nucleic acids to remove any unhybridized, single-stranded target RNA and probe. The RNases are inactivated, and the RNA is separated e.g. by denaturing polyacrylamide gel electrophoresis. The amount of intact RNA probe is proportional to the amount of target RNA in the RNA population. RPA can be used for relative and absolute quantitation of gene expression and also for mapping RNA structure, such as intron/exon boundaries and transcription start sites. The RNase protection assay is preferable to Northern blot analysis as it generally has a lower limit of detection.

The antisense RNA probes used in RPA are generated by in vitro transcription of a DNA template with a defined endpoint and are typically in the range of 50-600 nucleotides. The use of RNA probes that include additional sequences not homologous to the target RNA allows the protected fragment to be distinguished from the full-length probe. RNA probes are typically used instead of DNA probes due to the ease of generating single-stranded RNA probes and the reproducibility and reliability of RNA:RNA duplex digestion with RNases (Ausubel et al. 2003), particularly preferred are probes with high specific activities.

Particularly preferred is the use of microarrays. The microarray analysis process can be divided into two main parts. First is the immobilization of known gene sequences onto glass slides or other solid support followed by hybridisation of the fluorescently labelled cDNA (comprising the sequences to be interrogated) to the known genes immobilized on the glass slide (or other solid phase). After hybridisation, arrays are scanned using a fluorescent microarray scanner. Analysing the relative fluorescent intensity of different genes provides a measure of the differences in gene expression.

DNA arrays can be generated by immobilizing presynthesized oligonucleotides onto prepared glass slides or other solid surfaces. In this case, representative gene sequences are manufactured and prepared using standard oligonucleotide synthesis and purification methods. These synthesized gene sequences are complementary to the RNA transcript(s) of the genes RASSF2A; TFAP2E; HIST1H4K & GSTPi and tend to be shorter sequences in the range of 25-70 nucleotides. Alternatively, immobilized oligos can be chemically synthesized in situ on the surface of the slide. In situ oligonucleotide synthesis involves the consecutive addition of the appropriate nucleotides to the spots on the microarray; spots not receiving a nucleotide are protected during each stage of the process using physical or virtual masks. Preferably said synthesized nucleic acids are locked nucleic acids.

In expression profiling microarray experiments, the RNA templates used are representative of the transcription profile of the cells or tissues under study. RNA is first isolated from the cell populations or tissues to be compared. Each RNA sample is then used as a template to generate fluorescently labelled cDNA via a reverse transcription reaction. Fluorescent labelling of the cDNA can be accomplished by either direct labelling or indirect labelling methods. During direct labelling, fluorescently modified nucleotides (e.g., Cy®3- or Cy®5-dCTP) are incorporated directly into the cDNA during the reverse transcription. Alternatively, indirect labelling can be achieved by incorporating aminoallyl-modified nucleotides during cDNA synthesis and then conjugating an N-hydroxysuccinimide (NHS)-ester dye to the aminoallyl-modified cDNA after the reverse transcription reaction is complete. Alternatively, the probe may be unlabelled, but may be detectable by specific binding with a ligand which is labelled, either directly or indirectly. Suitable labels and methods for labelling ligands (and probes) are known in the art, and include, for example, radioactive labels which may be incorporated by known methods (e.g., nick translation or kinasing). Other suitable labels include but are not limited to biotin, fluorescent groups, chemiluminescent groups (e.g., dioxetanes, particularly triggered dioxetanes), enzymes, antibodies, and the like.

To perform differential gene expression analysis, cDNA generated from different RNA samples are labelled with Cy®3. The resulting labelled cDNA is purified to remove unincorporated nucleotides, free dye and residual RNA. Following purification, the labelled cDNA samples are hybridised to the microarray. The stringency of hybridisation is determined by a number of factors during hybridisation and during the washing procedure, including temperature, ionic strength, length of time and concentration of formamide. These factors are outlined in, for example, Sambrook et al. (Molecular Cloning: A Laboratory Manual, 2nd ed., 1989). The microarray is scanned post-hybridisation using a fluorescent microarray scanner. The fluorescent intensity of each spot indicates the level of expression of the analysed gene; bright spots correspond to strongly expressed genes, while dim spots indicate weak expression.

Once the images are obtained, the raw data must be analysed. First, the background fluorescence must be subtracted from the fluorescence of each spot. The data is then normalized to a control sequence, such as exogenously added nucleic acids (preferably RNA or DNA), or a housekeeping gene panel to account for any non-specific hybridisation, array imperfections or variability in the array set-up, cDNA labelling, hybridisation or washing. Data normalization allows the results of multiple arrays to be compared.

Another aspect of the invention relates to a kit for use in diagnosis of prostate cell proliferative disorders, most preferably, prostate cancer in a subject according to the methods of the present invention, said kit comprising: a means for measuring the level of transcription of at least one gene selected from the group consisting of RASSF2A; TFAP2E; HIST1H4K & GSTPi. In a preferred embodiment the means for measuring the level of transcription comprise oligonucleotides or polynucleotides able to hybridise under stringent or moderately stringent conditions to the transcription products of a gene selected from the group consisting of RASSF2A; TFAP2E; HIST1H4K & GSTPi. In a most preferred embodiment the level of transcription is determined by techniques selected from the group of Northern Blot analysis, reverse transcriptase PCR, real-time PCR, RNAse protection, and microarray. In another embodiment of the invention the kit further comprises means for obtaining a biological sample of the patient. Preferred is a kit, which further comprises a container which is most preferably suitable for containing the means for measuring the level of transcription and the biological sample of the patient, and most preferably further comprises instructions for use and interpretation of the kit results.

In a preferred embodiment the kit comprises (a) a plurality of oligonucleotides or polynucleotides able to hybridise under stringent or moderately stringent conditions to the transcription products of at least one gene selected from the group consisting of RASSF2A; TFAP2E; HIST1H4K & GSTPi; (b) a container, preferably suitable for containing the oligonucleotides or polynucleotides and a biological sample of the patient comprising the transcription products wherein the oligonucleotides or polynucleotides can hybridise under stringent or moderately stringent conditions to the transcription products, (c) means to detect the hybridisation of (b); and optionally, (d) instructions for use and interpretation of the kit results The kit may also contain other components such as hybridisation buffer (where the oligonucleotides are to be used as a probe) packaged in a separate container. Alternatively, where the oligonucleotides are to be used to amplify a target region, the kit may contain, packaged in separate containers, a polymerase and a reaction buffer optimised for primer extension mediated by the polymerase, such as PCR. Preferably said polymerase is a reverse transcriptase. It is further preferred that said kit further contains an Rnase reagent.

The present invention further provides for methods for the detection of the presence of the polypeptide encoded by said gene sequences in a sample obtained from a patient.

Aberrant levels of polypeptide expression of the polypeptides encoded by at least one gene selected from the group consisting of RASSF2A; TFAP2E; HIST1H4K & GSTPi are associated with the presence of cancer.

According to the present invention, under expression of said polypeptides is associated with the presence of prostate cell proliferative disorders, in particular, prostate cancer.

Any method known in the art for detecting polypeptides can be used. Such methods include, but are not limited to mass-spectrometry, immunodiffusion, immunoelectrophoresis, immunochemical methods, binder-ligand assays, immunohistochemical techniques, agglutination and complement assays (e.g., see Basic and Clinical Immunology, Sites and Terr, eds., Appleton & Lange, Norwalk, Conn., pp 217-262, 1991 which is incorporated by reference). Preferred are binder-ligand immunoassay methods including reacting antibodies with an epitope or epitopes and competitively displacing a labelled polypeptide or derivative thereof.

Certain embodiments of the present invention comprise the use of antibodies specific to the polypeptide(s) encoded by the RASSF2A; TFAP2E; HIST1H4K & GSTPi genes.

Such antibodies are useful for cancer diagnosis. In certain embodiments production of monoclonal or polyclonal antibodies can be induced by the use of an epitope encoded by a polypeptide of a gene selected from the group consisting of RASSF2A; TFAP2E; HIST1H4K & GSTPi as an antigene. Such antibodies may in turn be used to detect expressed polypeptides as markers for cancer diagnosis. The levels of such polypeptides present may be quantified by conventional methods. Antibody-polypeptide binding may be detected and quantified by a variety of means known in the art, such as labelling with fluorescent or radioactive ligands. The invention further comprises kits for performing the above-mentioned procedures, wherein such kits contain antibodies specific for the investigated polypeptides.

Numerous competitive and non-competitive polypeptide binding immunoassays are well known in the art. Antibodies employed in such assays may be unlabelled, for example as used in agglutination tests, or labelled for use a wide variety of assay methods. Labels that can be used include radionuclides, enzymes, fluorescers, chemiluminescers, enzyme substrates or co-factors, enzyme inhibitors, particles, dyes and the like. Preferred assays include but are not limited to radioimmunoassay (RIA), enzyme immunoassays, e.g., enzyme-linked immunosorbent assay (ELISA), fluorescent immunoassays and the like. Polyclonal or monoclonal antibodies or epitopes thereof can be made for use in immunoassays by any of a number of methods known in the art.

In an alternative embodiment of the method the proteins may be detected by means of western blot analysis. Said analysis is standard in the art, briefly proteins are separated by means of electrophoresis e.g. SDS-PAGE. The separated proteins are then transferred to a suitable membrane (or paper) e.g. nitrocellulose, retaining the spacial separation achieved by electrophoresis. The membrane is then incubated with a blocking agent to bind remaining sticky places on the membrane, commonly used agents include generic protein (e.g. milk protein). An antibody specific to the protein of interest is then added, said antibody being detectably labelled for example by dyes or enzymatic means (e.g. alkaline phosphatase or horseradish peroxidase). The location of the antibody on the membrane is then detected.

In an alternative embodiment of the method the proteins may be detected by means of immunohistochemistry (the use of antibodies to probe specific antigens in a sample). Said analysis is standard in the art, wherein detection of antigens in tissues is known as immunohistochemistry, while detection in cultured cells is generally termed immunocytochemistry. Briefly the primary antibody to be detected by binding to its specific antigen. The antibody-antigen complex is then bound by a secondary enzyme conjugated antibody. In the presence of the necessary substrate and chromogen the bound enzyme is detected according to coloured deposits at the antibody-antigen binding sites. There is a wide range of suitable sample types, antigen-antibody affinity, antibody types, and detection enhancement methods. Thus optimal conditions for immunohistochemical or immunocytochemical detection must be determined by the person skilled in the art for each individual case.

One approach for preparing antibodies to a polypeptide is the selection and preparation of an amino acid sequence of all or part of the polypeptide, chemically synthesising the amino acid sequence and injecting it into an appropriate animal, usually a rabbit or a mouse (Milstein and Kohler Nature 256:495-497, 1975; Gulfre and Milstein, Methods in Enzymology: Immunochemical Techniques 73:1-46, Langone and Banatis eds., Academic Press, 1981 which are incorporated by reference in its entirety). Methods for preparation of the polypeptides or epitopes thereof include, but are not limited to chemical synthesis, recombinant DNA techniques or isolation from biological samples.

In the final step of the method the diagnosis of the patient is determined, whereby under-expression (of RASSF2A; TFAP2E; HIST1H4K & GSTPi mRNA or polypeptides) is indicative of the presence of cancer. The term under-expression shall be taken to mean expression at a detected level less than a pre-determined cut off which may be selected from the group consisting of the mean, median or an optimised threshold value.

Another aspect of the invention provides a kit for use in diagnosis of cancer in a subject according to the methods of the present invention, comprising: a means for detecting polypeptides of at least one gene selected from the group consisting of RASSF2A; TFAP2E; HIST1H4K & GSTPi. The means for detecting the polypeptides comprise preferably antibodies, antibody derivatives, or antibody fragments. The polypeptides are most preferably detected by means of Western Blotting utilizing a labelled antibody. In another embodiment of the invention the kit further comprising means for obtaining a biological sample of the patient. Preferred is a kit, which further comprises a container suitable for containing the means for detecting the polypeptides in the biological sample of the patient, and most preferably further comprises instructions for use and interpretation of the kit results. In a preferred embodiment the kit comprises: (a) a means for detecting polypeptides of at least one gene selected from the group consisting of RASSF2A; TFAP2E; HIST1H4K & GSTPi; (b) a container suitable for containing the said means and the biological sample of the patient comprising the polypeptides wherein the means can form complexes with the polypeptides; (c) a means to detect the complexes of (b); and optionally (d) instructions for use and interpretation of the kit results.

The kit may also contain other components such as buffers or solutions suitable for blocking, washing or coating, packaged in a separate container.

Particular embodiments of the present invention provide a novel application of the analysis of methylation levels and/or patterns within said sequences that enables a precise detection, characterisation and/or treatment of prostate carcinoma. Early detection of cancer is directly linked with disease prognosis, and the disclosed method thereby enables the physician and patient to make better and more informed treatment decisions.

Further Improvements

The present invention provides novel uses for the genomic sequences SEQ ID NO: 1 TO SEQ ID NO: 4. Additional embodiments provide modified variants of SEQ ID NO: 1 TO SEQ ID NO: 4, as well as oligonucleotides and/or PNA-oligomers for analysis of cytosine methylation patterns within SEQ ID NO: 1 TO SEQ ID NO: 4.

An objective of the invention comprises analysis of the methylation state of one or more CpG dinucleotides within SEQ ID NO: 1 TO SEQ ID NO: 4 and sequences complementary thereto.

The disclosed invention provides treated nucleic acids, derived from genomic SEQ ID NO: 1 to SEQ ID NO: 4, wherein the treatment is suitable to convert at least one unmethylated cytosine base of the genomic DNA sequence to uracil or another base that is detectably dissimilar to cytosine in terms of hybridization. The genomic sequences in question may comprise one, or more consecutive methylated CpG positions. Said treatment preferably comprises use of a reagent selected from the group consisting of bisulfite, hydrogen sulfite, disulfite, and combinations thereof. In a preferred embodiment of the invention, the invention provides a non-naturally occurring modified nucleic acid comprising a sequence of at least 16 contiguous nucleotide bases in length of a sequence selected from the group consisting of SEQ ID NO: 5 TO SEQ ID NO: 20. In further preferred embodiments of the invention said nucleic acid is at least 50, 100, 150, 200, 250 or 500 base pairs in length of a segment of the nucleic acid sequence disclosed in SEQ ID NO: 5 to SEQ ID NO: 20. Particularly preferred is a nucleic acid molecule that is not identical or complementary to all or a portion of the sequences SEQ ID NO: 5 to SEQ ID NO: 20 but not SEQ ID NO: 1 to SEQ ID NO: 4 or other naturally occurring DNA.

It is preferred that said sequence comprises at least one CpG, TpA or CpA dinucleotide and sequences complementary thereto. The sequences of SEQ ID NO: 5 TO SEQ ID NO: 20 provide non-naturally occurring modified versions of the nucleic acid according to SEQ ID NO: 1 TO SEQ ID NO: 4, wherein the modification of each genomic sequence results in the synthesis of a nucleic acid having a sequence that is unique and distinct from said genomic sequence as follows. For each sense strand genomic DNA, e.g., SEQ ID NO: 1, four converted versions are disclosed. A first version wherein "C" is converted to "T," but "CpG" remains "CpG" (i.e., corresponds to case where, for the genomic sequence, all "C" residues of CpG dinucleotide sequences are methylated and are thus not converted); a second version discloses the complement of the disclosed genomic DNA sequence (i.e. antisense strand), wherein "C" is converted to "T," but "CpG" remains "CpG" (i.e., corresponds to case where, for all "C" residues of CpG dinucleotide sequences are methylated and are thus not converted). The 'upmethylated' converted sequences of SEQ ID NO: 1 to SEQ ID NO: 4 correspond to SEQ ID NO: 5 to SEQ ID NO: 12. A third chemically converted version of each genomic sequences is provided, wherein "C" is converted to "T" for all "C" residues, including those of "CpG" dinucleotide sequences (i.e., corresponds to case where, for the genomic sequences, all "C" residues of CpG dinucleotide sequences are unmethylated); a final chemically converted version of each sequence, discloses the complement of the disclosed genomic DNA sequence (i.e. antisense strand), wherein "C" is converted to "T" for all "C" residues, including those of "CpG" dinucleotide sequences (i.e., corresponds to case Q where, for the complement (antisense strand) of each genomic sequence, all "C" residues of CpG dinucleotide sequences are unmethylated). The 'downmethylated' converted sequences of SEQ ID NO: 1 to SEQ ID NO: 4 corresponds to SEQ ID NO: 13 to SEQ ID NO: 20. See Table 1 for further details.

Significantly, heretofore, the nucleic acid sequences and molecules according SEQ ID NO: 5 to SEQ ID NO: 20 were not implicated in or connected with the detection, classification or treatment of cancer.

In an alternative preferred embodiment, the invention further provides oligonucleotides or oligomers suitable for use in the methods of the invention for detecting the cytosine methylation state within genomic or treated (chemically modified) DNA, according to SEQ ID NO: 1 to SEQ ID NO: 4 TO SEQ ID NO: 20. Said oligonucleotide or oligomer nucleic acids provide novel diagnostic means. Said oligonucleotide or oligomer comprising a nucleic acid sequence having a length of at least nine (9) nucleotides which is identical to, hybridizes, under moderately stringent or stringent conditions (as defined herein above), to a treated nucleic acid sequence according to SEQ ID NO: 5 to SEQ ID NO: 20 and/or sequences complementary thereto, or to a genomic sequence according to SEQ ID NO: 1 to SEQ ID NO: 4 and/or sequences complementary thereto.

Thus, the present invention includes nucleic acid molecules (e.g., oligonucleotides and peptide nucleic acid (PNA) molecules (PNA-oligomers)) that hybridize under moderately stringent and/or stringent hybridization conditions to all or a portion of the sequences SEQ ID NO: 1 to SEQ ID NO: 4 TO SEQ ID NO: 20 or to the complements thereof. Particularly preferred is a nucleic acid molecule that hybridizes under moderately stringent and/or stringent hybridization conditions to all or a portion of the sequences SEQ ID NO: 5 to SEQ ID NO: 20 but not SEQ ID NO: 1 to SEQ ID NO: 4 or other human genomic DNA.

The identical or hybridizing portion of the hybridizing nucleic acids is typically at least 9, 16, 20, 25, 30 or 35 nucleotides in length. However, longer molecules have inventive utility, and are thus within the scope of the present invention.

Preferably, the hybridizing portion of the inventive hybridizing nucleic acids is at least 95%, or at least 98%, or 100% identical to the sequence, or to a portion thereof of SEQ ID NO: 1 to SEQ ID NO: 4 TO SEQ ID NO: 20, or to the complements thereof.

Hybridizing nucleic acids of the type described herein can be used, for example, as a primer (e.g., a PCR primer), or a diagnostic and/or prognostic probe or primer. Preferably, hybridization of the oligonucleotide probe to a nucleic acid sample is performed under stringent conditions and the probe is 100% identical to the target sequence. Nucleic acid duplex or hybrid stability is expressed as the melting temperature or Tm, which is the temperature at which a probe dissociates from a target DNA. This melting temperature is used to define the required stringency conditions.

For target sequences that are related and substantially identical to the corresponding sequence of SEQ ID NO: 1 to SEQ ID NO: 4 (such as allelic variants and SNPs), rather than identical, it is useful to first establish the lowest temperature at which only homologous hybridization occurs with a particular concentration of salt (e.g., SSC or SSPE). Then, assuming that 1% mismatching results in a 1° C. decrease in the Tm, the temperature of the final wash in the hybridization reaction is reduced accordingly (for example, if sequences having >95% identity with the probe are sought, the final wash temperature is decreased by 5° C.). In practice, the change in Tm can be between 0.5° C. and 1.5° C. per 1% mismatch.

Examples of inventive oligonucleotides of length X (in nucleotides), as indicated by polynucleotide positions with reference to, e.g., SEQ ID NO: 2, include those corresponding to sets (sense and antisense sets) of consecutively overlapping oligonucleotides of length X, where the oligonucleotides within each consecutively overlapping set (corresponding to a given X value) are defined as the finite set of Z oligonucleotides from nucleotide positions:

$n$ to $(n+(X-1))$;

where n=1, 2, 3, . . . (Y−(X−1));

where Y equals the length (nucleotides or base pairs) of SEQ ID NO: 2 (6096);

where X equals the common length (in nucleotides) of each oligonucleotide in the set (e.g., X=20 for a set of consecutively overlapping 20-mers); and where the number (Z) of consecutively overlapping oligomers of length X for a given SEQ ID NO 1 of length Y is equal to Y−(X−1). For example Z=6096 −19=6077 for either sense or antisense sets of SEQ H) NO: 2, where X=20.

Preferably, the set is limited to those oligomers that comprise at least one CpG, TpG or CpA dinucleotide.

Examples of inventive 20-mer oligonucleotides include the following set of 2,261 oligomers (and the antisense set complementary thereto), indicated by polynucleotide positions with reference to SEQ ID NO: 1 to SEQ ID NO: 4:

1-20, 2-21, 3-22, 4-23, 5-24, . . . and 6077-6096.

Preferably, the set is limited to those oligomers that comprise at least one CpG, TpG or CpA dinucleotide.

Likewise, examples of inventive 25-mer oligonucleotides include the following set of 2,256 oligomers (and the antisense set complementary thereto), indicated by polynucleotide positions with reference to SEQ ID NO: 2:

1-25, 2-26, 3-27, 4-28, 5-29, . . . and 6072-6096.

Preferably, the set is limited to those oligomers that comprise at least one CpG, TpG or CpA dinucleotide.

The present invention encompasses, for each of SEQ ID NO: 1 to SEQ ID NO: 4 TO SEQ ID NO: 20 (sense and antisense), multiple consecutively overlapping sets of oligonucleotides or modified oligonucleotides of length X, where, e.g., X=9, 10, 17, 20, 22, 23, 25, 27, 30 or 35 nucleotides.

The oligonucleotides or oligomers according to the present invention constitute effective tools useful to ascertain genetic and epigenetic parameters of the genomic sequences corresponding to SEQ ID NO: 1 to SEQ ID NO: 4. Preferred sets of such oligonucleotides or modified oligonucleotides of length X are those consecutively overlapping sets of oligomers corresponding to SEQ ID NO: 1 to SEQ ID NO: 4 to SEQ ID NO: 20 (and to the complements thereof). Preferably, said oligomers comprise at least one CpG, TpG or CpA dinucleotide.

Particularly preferred oligonucleotides or oligomers according to the present invention are those in which the cytosine of the CpG dinucleotide (or of the corresponding converted TpG or CpA dinuculeotide) sequences is within the middle third of the oligonucleotide; that is, where the oligonucleotide is, for example, 13 bases in length, the CpG, TpG or CpA dinucleotide is positioned within the fifth to ninth nucleotide from the 5'-end.

The oligonucleotides of the invention can also be modified by chemically linking the oligonucleotide to one or more moieties or conjugates to enhance the activity, stability or detection of the oligonucleotide. Such moieties or conjugates include chromophores, fluorophors, lipids such as cholesterol, cholic acid, thioether, aliphatic chains, phospholipids, polyamines, polyethylene glycol (PEG), palmityl moieties, and others as disclosed in, for example, U.S. Pat. Nos. 5,514,758, 5,565,552, 5,567,810, 5,574,142, 5,585, 481, 5,587,371, 5,597,696 and 5,958,773. The probes may also exist in the form of a PNA (peptide nucleic acid) which has particularly preferred pairing properties. Thus, the oligonucleotide may include other appended groups such as peptides, and may include hybridization-triggered cleavage agents (Krol et al., BioTechniques 6:958-976, 1988) or intercalating agents (Zon, Pharm. Res. 5:539-549, 1988). To this end, the oligonucleotide may be conjugated to another molecule, e.g., a chromophore, fluorophor, peptide, hybridization-triggered cross-linking agent, transport agent, hybridization-triggered cleavage agent, etc.

The oligonucleotide may also comprise at least one art-recognized modified sugar and/or base moiety, or may comprise a modified backbone or non-natural internucleoside linkage.

The oligonucleotides or oligomers according to particular embodiments of the present invention are typically used in 'sets,' which contain at least one oligomer for analysis of each of the CpG dinucleotides of a genomic sequence selected from the group consisting SEQ ID NO: 1 to SEQ ID NO: 4 and sequences complementary thereto, or to the corresponding CpG TpG or CpA dinucleotide within a sequence of the treated nucleic acids according to SEQ ID NO: 5 to SEQ ID NO: 20 and sequences complementary thereto. However, it is anticipated that for economic or other factors it may be preferable to analyse a limited selection of the CpG dinucleotides within said sequences, and the content of the set of oligonucleotides is altered accordingly.

Therefore, in particular embodiments, the present invention provides a set of at least two (2) (oligonucleotides and/or PNA-oligomers) useful for detecting the cytosine methylation state in treated genomic DNA (SEQ ID NO: 5 to SEQ ID NO: 20), or in genomic DNA (SEQ ID NO: 1 to SEQ ID NO: 4 and sequences complementary thereto). These probes enable diagnosis and detection of prostate cell proliferative disorders, most preferably, prostate carcinoma. The set of oligomers may also be used for detecting single nucleotide polymorphisms (SNPs) in treated genomic DNA (SEQ ID NO: 5 to SEQ ID NO: 20), or in genomic DNA (SEQ ID NO: 1 to SEQ ID NO: 4 and sequences complementary thereto).

In preferred embodiments, at least one, and more preferably all members of a set of oligonucleotides is bound to a solid phase.

In further embodiments, the present invention provides a set of at least two (2) oligonucleotides that are used as 'primer' oligonucleotides for amplifying DNA sequences of one of SEQ ID NO: 1 to SEQ ID NO: 4 TO SEQ ID NO: 20 and sequences complementary thereto, or segments thereof.

It is anticipated that the oligonucleotides may constitute all or part of an "array" or "DNA chip" (i.e., an arrangement of different oligonucleotides and/or PNA-oligomers bound to a solid phase). Such an array of different oligonucleotide-and/or PNA-oligomer sequences can be characterized, for example, in that it is arranged on the solid phase in the form of a rectangular or hexagonal lattice. The solid-phase surface may be composed of silicon, glass, polystyrene, aluminum, steel, iron, copper, nickel, silver, or gold. Nitrocellulose as well as plastics such as nylon, which can exist in the form of pellets or also as resin matrices, may also be used. An overview of the Prior Art in oligomer array manufacturing can be gathered from a special edition of Nature Genetics (Nature Genetics Supplement, Volume 21, January 1999, and from the literature cited therein). Fluorescently labelled probes are often used for the scanning of immobilized DNA arrays. The simple attachment of Cy3 and Cy5 dyes to the 5'-OH of the specific probe is particularly suitable for fluorescence labels. The detection of the fluorescence of the hybridised probes may be carried out, for example, via a confocal microscope. Cy3 and Cy5 dyes, besides many others, are commercially available.

It is also anticipated that the oligonucleotides, or particular sequences thereof, may constitute all or part of an "virtual array" wherein the oligonucleotides, or particular sequences thereof, are used, for example, as 'specifiers' as part of, or in combination with a diverse population of unique labeled probes to analyze a complex mixture of analytes. Such a method, for example is described in US 2003/0013091 (U.S. Ser. No. 09/898,743, published 16 Jan. 2003). In such methods, enough labels are generated so that each nucleic acid in the complex mixture (i.e., each analyte) can be uniquely bound by a unique label and thus detected (each label is directly counted, resulting in a digital read-out of each molecular species in the mixture).

It is particularly preferred that the oligomers according to the invention are utilised for detecting, or for diagnosing prostate cell proliferative disorders, most preferably, prostate carcinoma.

In the most preferred embodiment of the method, the presence or absence of prostate cell proliferative disorders, most preferably, prostate cancer is determined. This is achieved by analysis of the methylation status of at least one and more preferably a plurality of, target sequence(s) comprising at least one CpG position said sequence comprising, or hybridizing under stringent conditions to at least 16, 50, 100 or 500 contiguous nucleotides of a sequence selected from the group consisting SEQ ID NO: 1 to SEQ ID NO: 4 and complements thereof. Preferably a plurality of target regions (herein also referred to as a "gene panel") are analysed. Preferably target regions of 2, 3 or 4 genes are analysed. In one embodiment of the method said panel comprises the target regions of at least one gene selected from the group consisting of RASSF2A; TFAP2E; HIST1H4K & GSTPi and/or their promotor or regulatory regions. Preferably said panel comprises a target region of the gene HIST1H4K.

Particularly preferred are the following combinations of target regions of genes:
HIST1H4K+RASSF
HIST1H4K+GSTPi The present invention further provides a method for ascertaining genetic and/or epigenetic parameters of the genomic sequences according to SEQ ID NO: 1 to SEQ ID NO: 4 within a subject by analysing cytosine methylation and single nucleotide polymorphisms. Said method comprising contacting a nucleic acid comprising at least one genomic sequence selected from the group consisting SEQ ID NO: 1 to SEQ ID NO: 4 in a biological sample obtained from said subject with at least one reagent or a series of reagents, wherein said reagent or series of reagents, distinguishes between methylated and non-methylated CpG dinucleotides within the target nucleic acid(s).

In a preferred embodiment, said method comprises the following steps: In the first step, a sample of the tissue to be analysed is obtained. The source may be any suitable source, such as cell lines, histological slides, biopsies, paraffin-embedded tissue, body fluids, ejaculate, urine, blood plasma, blood serum, whole blood, isolated blood cells, cells isolated from the blood and all possible combinations thereof. It is preferred that said sources of DNA are ejaculate or body fluids selected from the group consisting ejaculate, urine, blood plasma, blood serum, whole blood, isolated blood cells, cells isolated from the blood.

The genomic DNA is then isolated from the sample. Genomic DNA may be isolated by any means standard in the art, including the use of commercially available kits. Briefly, wherein the DNA of interest is encapsulated in by a cellular membrane the biological sample must be disrupted and lysed by enzymatic, chemical or mechanical means. The DNA solution may then be cleared of proteins and other contaminants e.g. by digestion with proteinase K. The genomic DNA is then recovered from the solution. This may be carried out by means of a variety of methods including salting out, organic extraction or binding of the DNA to a solid phase support. The choice of method will be affected by several factors including time, expense and required quantity of DNA.

Wherein the sample DNA is not enclosed in a membrane (e.g. circulating DNA from a blood sample) methods standard in the art for the isolation and/or purification of DNA may be employed. Such methods include the use of a protein degenerating reagent e.g. chaotropic salt e.g. guanidine hydrochloride or urea; or a detergent e.g. sodium dodecyl sulphate (SDS), cyanogen bromide. Alternative methods include but are not limited to ethanol precipitation or propanol precipitation, vacuum concentration amongst others by means of a centrifuge. The person skilled in the art may also make use of devices such as filter devices e.g. ultrafiltration, silica surfaces or membranes, magnetic particles, polystyrol particles, polystyrol surfaces, positively charged surfaces, and positively charged membranes, charged membranes, charged surfaces, charged switch membranes, charged switched surfaces.

Once the nucleic acids have been extracted, the genomic double stranded DNA is used in the analysis.

In the second step of the method, the genomic DNA sample is treated in such a manner that cytosine bases which are unmethylated at the 5'-position are converted to uracil, thymine, or another base which is dissimilar to cytosine in terms of hybridisation behaviour. This will be understood as 'pre-treatment' or 'treatment' herein.

This is preferably achieved by means of treatment with a bisulfite reagent. The term "bisulfite reagent" refers to a reagent comprising bisulfite, disulfite, hydrogen sulfite or combinations thereof, useful as disclosed herein to distinguish between methylated and unmethylated CpG dinucleotide sequences. Methods of said treatment are known in the art (e.g. PCT/EP2004/011715, which is incorporated by reference in its entirety). It is preferred that the bisulfite treatment is conducted in the presence of denaturing solvents such as but not limited to n-alkylenglycol, particularly diethylene glycol dimethyl ether (DME), or in the presence of dioxane or dioxane derivatives. In a preferred embodiment the denaturing solvents are used in concentrations between 1% and 35% (v/v). It is also preferred that the bisulfite reaction is carried out in the presence of scavengers such as but not limited to chromane derivatives, e.g., 6-hydroxy-2,5,7,8, -tetramethylchromane 2-carboxylic acid or trihydroxybenzoe acid and derivates thereof, e.g. Gallic acid (see: PCT/EP2004/011715 which is incorporated by reference in its entirety). The bisulfite conversion is preferably carried out at a reaction temperature between 30° C. and 70° C., whereby the temperature is increased to over 85° C. for short periods of times during the reaction (see: PCT/EP2004/011715 which is incorporated by reference in its entirety). The bisulfite treated DNA is preferably purified prior to the quantification. This may be conducted by any means known in the art, such as but not limited to ultrafiltration, preferably carried out by means of Microcon^™ columns (manufactured by Millipore^™). The purification is carried out according to a modified manufacturer's protocol (see: PCT/EP2004/011715 which is incorporated by reference in its entirety).

In the third step of the method, fragments of the treated DNA are amplified, using sets of primer oligonucleotides according to the present invention, and an amplification enzyme. The amplification of several DNA segments can be carried out simultaneously in one and the same reaction vessel. Typically, the amplification is carried out using a polymerase chain reaction (PCR). Preferably said amplificates are 100 to 2,000 base pairs in length. The set of primer oligonucleotides includes at least two oligonucleotides whose sequences are each reverse complementary, identical, or hybridise under stringent or highly stringent conditions to an at least 16-base-pair long segment of the base sequences of one of SEQ ID NO: 5 to SEQ ID NO: 20 and sequences complementary thereto.

In an alternate embodiment of the method, the methylation status of pre-selected CpG positions within at least one genomic sequence selected from the group consisting SEQ ID NO: 1 to SEQ ID NO: 4, may be detected by use of methylation-specific primer oligonucleotides. This technique (MSP) has been described in U.S. Pat. No. 6,265,171 to Herman. The use of methylation status specific primers for the amplification of bisulfite treated DNA allows the differentiation between methylated and unmethylated nucleic acids. MSP primers pairs contain at least one primer which hybridises to a bisulfite treated CpG dinucleotide. Therefore, the sequence of said primers comprises at least one CpG dinucleotide. MSP primers specific for non-methylated DNA contain a "T" at the position of the C position in the CpG. Preferably, therefore, the base sequence of said primers is required to comprise a sequence having a length of at least 9 nucleotides which hybridises to a treated nucleic acid sequence according to one of SEQ ID NO: 5 to SEQ ID NO: 20 and sequences complementary thereto, wherein the base sequence of said oligomers comprises at least one CpG dinucleotide. A further preferred embodiment of the method comprises the use of blocker oligonucleotides (the HeavyMethyl™ assay). The use of such blocker oligonucleotides has been described by Yu et al., BioTechniques 23:714-720, 1997. Blocking probe oligonucleotides are hybridised to the bisulfite treated nucleic acid concurrently with the PCR primers. PCR amplification of the nucleic acid is terminated at the 5' position of the blocking probe, such that amplification of a nucleic acid is suppressed where the complementary sequence to the blocking probe is present. The probes may be designed to hybridize to the bisulfite treated nucleic acid in a methylation status specific manner. For example, for detection of methylated nucleic acids within a population of unmethylated nucleic acids, suppression of the amplification of nucleic acids which are unmethylated at the position in question would be carried out by the use of blocking probes comprising a 'CpA' or 'TpA' at the position in question, as opposed to a 'CpG' if the suppression of amplification of methylated nucleic acids is desired.

For PCR methods using blocker oligonucleotides, efficient disruption of polymerase-mediated amplification requires that blocker oligonucleotides not be elongated by the polymerase. Preferably, this is achieved through the use of blockers that are 3'-deoxyoligonucleotides, or oligonucleotides derivitized at the 3' position with other than a "free" hydroxyl group. For example, 3'-O-acetyl oligonucleotides are representative of a preferred class of blocker molecule.

Additionally, polymerase-mediated decomposition of the blocker oligonucleotides should be precluded. Preferably, such preclusion comprises either use of a polymerase lacking 5'-3' exonuclease activity, or use of modified blocker oligonucleotides having, for example, thioate bridges at the 5'-terminii thereof that render the blocker molecule nuclease-resistant. Particular applications may not require such 5' modifications of the blocker. For example, if the blocker- and primer-binding sites overlap, thereby precluding binding of the primer (e.g., with excess blocker), degradation of the blocker oligonucleotide will be substantially precluded. This is because the polymerase will not extend the primer toward, and through (in the 5'-3' direction) the blocker—a process that normally results in degradation of the hybridized blocker oligonucleotide.

A particularly preferred blocker/PCR embodiment, for purposes of the present invention and as implemented herein, comprises the use of peptide nucleic acid (PNA) oligomers as blocking oligonucleotides. Such PNA blocker oligomers are ideally suited, because they are neither decomposed nor extended by the polymerase.

Preferably, therefore, the base sequence of said blocking oligonucleotides is required to comprise a sequence having a length of at least 9 nucleotides which hybridises to a treated nucleic acid sequence according to one of SEQ ID NO: 5 to SEQ ID NO: 20 and sequences complementary thereto, wherein the base sequence of said oligonucleotides comprises at least one CpG, TpG or CpA dinucleotide.

The fragments obtained by means of the amplification can carry a directly or indirectly detectable label. Preferred are labels in the form of fluorescence labels, radionuclides, or detachable molecule fragments having a typical mass which can be detected in a mass spectrometer. Where said labels are mass labels, it is preferred that the labelled amplificates have a single positive or negative net charge, allowing for better delectability in the mass spectrometer. The detection may be carried out and visualized by means of, e.g., matrix assisted laser desorption/ionization mass spectrometry (MALDI) or using electron spray mass spectrometry (ESI).

Matrix Assisted Laser Desorption/ionization Mass Spectrometry (MALDI-TOF) is a very efficient development for the analysis of biomolecules (Karas & Hillenkamp, Anal Chem., 60:2299-301, 1988). An analyte is embedded in a light-absorbing matrix. The matrix is evaporated by a short laser pulse thus transporting the analyte molecule into the vapor phase in an unfragmented manner. The analyte is ionized by collisions with matrix molecules. An applied voltage accelerates the ions into a field-free flight tube. Due to their different masses, the ions are accelerated at different rates. Smaller ions reach the detector sooner than bigger ones. MALDI-TOF spectrometry is well suited to the analysis of peptides and proteins. The analysis of nucleic acids is somewhat more difficult (Gut & Beck, Current Innovations and Future Trends, 1:147-57, 1995). The sensitivity with respect to nucleic acid analysis is approximately 100-times less than for peptides, and decreases disproportionally with increasing fragment size. Moreover, for nucleic acids having a multiply negatively charged backbone, the ionization process via the matrix is considerably less efficient. In MALDI-TOF spectrometry, the selection of the matrix plays an eminently important role. For desorption of peptides, several very efficient matrixes have been found which produce a very fine crystallisation. There are now several responsive matrixes for DNA, however, the difference in sensitivity between peptides and nucleic acids has not been reduced. This difference in sensitivity can be reduced, however, by chemically modifying the DNA in such a manner that it becomes more similar to a peptide. For example, phosphorothioate nucleic acids, in which the usual phosphates of the backbone are substituted with thiophosphates, can be converted into a charge-neutral DNA using simple alkylation chemistry (Gut & Beck, Nucleic Acids Res. 23: 1367-73, 1995). The coupling of a charge tag to this modified DNA results in an increase in MALDI-TOF sensitivity to the same level as that found for peptides. A further advantage of charge tagging is the increased stability of the analysis against impurities, which makes the detection of unmodified substrates considerably more difficult.

In the fourth step of the method, the amplificates obtained during the third step of the method are analysed in order to ascertain the methylation status of the CpG dinucleotides prior to the treatment.

In embodiments where the amplificates were obtained by means of MSP amplification, the presence or absence of an amplificate is in itself indicative of the methylation state of the CpG positions covered by the primer, according to the base sequences of said primer.

Amplificates obtained by means of both standard and methylation specific PCR may be further analysed by means of based-based methods such as, but not limited to, array technology and probe based technologies as well as by means of techniques such as sequencing and template directed extension.

In one embodiment of the method, the amplificates synthesised in step three are subsequently hybridized to an array or a set of oligonucleotides and/or PNA probes. In this context, the hybridization takes place in the following manner: the set of probes used during the hybridization is preferably composed of at least 2 oligonucleotides or PNA-oligomers; in the process, the amplificates serve as probes which hybridize to oligonucleotides previously bonded to a solid phase; the non-hybridized fragments are subsequently removed; said oligonucleotides contain at least one base sequence having a length of at least 9 nucleotides which is reverse complementary or identical to a segment of the base sequences specified in the present Sequence Listing; and the segment comprises at least one CpG, TpG or CpA dinucleotide. The hybridizing portion of the hybridizing nucleic acids is typically at least 9, 15, 20, 25, 30 or 35 nucleotides in length. However, longer molecules have inventive utility, and are thus within the scope of the present invention.

In a preferred embodiment, said dinucleotide is present in the central third of the oligomer. For example, wherein the oligomer comprises one CpG dinucleotide, said dinucleotide is preferably the fifth to ninth nucleotide from the 5'-end of a 13-mer. One oligonucleotide exists for the analysis of each CpG dinucleotide within a sequence selected from the group consisting SEQ ID NO: 1 to SEQ ID NO: 4, and the equivalent positions within SEQ ID NO: 5 to SEQ ID NO: 20. Said oligonucleotides may also be present in the form of peptide nucleic acids. The non-hybridised amplificates are then removed. The hybridised amplificates are then detected. In this context, it is preferred that labels attached to the amplificates are identifiable at each position of the solid phase at which an oligonucleotide sequence is located.

In yet a further embodiment of the method, the genomic methylation status of the CpG positions may be ascertained by means of oligonucleotide probes (as detailed above) that are hybridised to the bisulfite treated DNA concurrently with the PCR amplification primers (wherein said primers may either be methylation specific or standard).

A particularly preferred embodiment of this method is the use of fluorescence-based Real Time Quantitative PCR (Heid et al., Genome Res. 6:986-994, 1996; also see U.S. Pat. No. 6,331,393) employing a dual-labelled fluorescent oligonucleotide probe (TaqMan™ PCR, using an ABI Prism 7700 Sequence Detection System, Perkin Elmer Applied Biosystems, Foster City, Calif.). The TaqMan™ PCR reaction employs the use of a non-extendible interrogating oligonucleotide, called a TaqMan™ probe, which, in preferred embodiments, is designed to hybridise to a CpG-rich sequence located between the forward and reverse amplification primers. The TaqMan™ probe further comprises a fluorescent "reporter moiety" and a "quencher moiety" covalently bound to linker moieties (e.g., phosphoramidites) attached to the nucleotides of the TaqMan™ oligonucleotide. For analysis of methylation within nucleic acids subsequent to bisulfite treatment, it is required that the probe be methylation specific, as described in U.S. Pat. No. 6,331,393, (hereby incorporated by reference in its entirety) also known as the MethyLight™ assay. Variations on the TaqMan™ detection methodology that are also suitable for use with the described invention include the use of dual-probe technology (Lightcycler™) or fluorescent amplification primers (Sunrise™ technology). Both these techniques may be adapted in a manner suitable for use with bisulfite treated DNA, and moreover for methylation analysis within CpG dinucleotides.

In a further preferred embodiment of the method, the fourth step of the method comprises the use of template-directed oligonucleotide extension, such as MS-SNuPE as described by Gonzalgo & Jones, Nucleic Acids Res. 25:2529-2531, 1997.

In yet a further embodiment of the method, the fourth step of the method comprises sequencing and subsequent sequence analysis of the amplificate generated in the third step of the method (Sanger F., et al., Proc Natl Acad Sci USA 74:5463-5467, 1977).

Best Mode

In the most preferred embodiment of the method the genomic nucleic acids are isolated and treated according to the first three steps of the method outlined above, namely:
a) obtaining, from a subject, a biological sample having subject genomic DNA;
b) extracting or otherwise isolating the genomic DNA;
c) treating the genomic DNA of b), or a fragment thereof, with one or more reagents to convert cytosine bases that are unmethylated in the 5-position thereof to uracil or to another base that is detectably dissimilar to cytosine in terms of hybridization properties; and wherein
d) amplifying subsequent to treatment in c) is carried out in a methylation specific manner, namely by use of methylation specific primers or blocking oligonucleotides, and further wherein
e) detecting of the amplificates is carried out by means of a real-time detection probe, as described above.

Preferably, where the subsequent amplification of d) is carried out by means of methylation specific primers, as described above, said methylation specific primers comprise a sequence having a length of at least 9 nucleotides which hybridises to a treated nucleic acid sequence according to one of SEQ ID NO: 5 to SEQ ID NO: 20 and sequences complementary thereto, wherein the base sequence of said oligomers comprise at least one CpG dinucleotide.

Step e) of the method, namely the detection of the specific amplificates indicative of the methylation status of one or more CpG positions of at least one genomic sequence selected from the group consisting SEQ ID NO: 1 to SEQ ID NO: 4 is carried out by means of real-time detection methods as described above.

Additional embodiments of the invention provide a method for the analysis of the methylation status of genomic DNA according to the invention (SEQ ID NO: 1 to SEQ ID NO: 4, and complements thereof) without the need for bisulfite conversion. Methods are known in the art wherein a methylation sensitive restriction enzyme reagent, or a series of restriction enzyme reagents comprising methylation sensitive restriction enzyme reagents that distinguishes between methylated and non-methylated CpG dinucleotides within a target region are utilized in determining methylation, for example but not limited to DMH.

In the first step of such additional embodiments, the genomic DNA sample is isolated from tissue or cellular sources. Genomic DNA may be isolated by any means standard in the art, including the use of commercially available kits. Briefly, wherein the DNA of interest is encapsulated in by a cellular membrane the biological sample must be disrupted and lysed by enzymatic, chemical or mechanical means. The DNA solution may then be cleared of proteins and other contaminants, e.g., by digestion with proteinase K. The genomic DNA is then recovered from the solution. This may be carried out by means of a variety of methods including salting out, organic extraction or binding of the DNA to a solid phase support. The choice of method will be affected by several factors including time, expense and required quantity of DNA. All clinical sample types comprising neoplastic or potentially neoplastic matter are suitable for use in the present method, preferred are cell lines, histological slides, biopsies, paraffin-embedded tissue, body fluids, ejaculate, urine, blood plasma, blood serum, whole blood, isolated blood cells, cells isolated from the blood and combinations thereof. Body fluids are the preferred source of the DNA; particularly preferred are blood plasma, blood serum, whole blood, isolated blood cells and cells isolated from the blood.

Once the nucleic acids have been extracted, the genomic double-stranded DNA is used in the analysis.

In a preferred embodiment, the DNA may be cleaved prior to treatment with methylation sensitive restriction enzymes. Such methods are known in the art and may include both physical and enzymatic means. Particularly preferred is the use of one or a plurality of restriction enzymes which are not methylation sensitive, and whose recognition sites are AT rich and do not comprise CG dinucleotides. The use of such enzymes enables the conservation of CpG islands and CpG rich regions in the fragmented DNA. The non-methylation-specific restriction enzymes are preferably selected from the group consisting of MseI, BfaI, Csp6I, TruII, TvuII, Tru9I, Tvu9I, MaeI and XspI. Particularly preferred is the use of two or three such enzymes. Particularly preferred is the use of a combination of MseI, BfaI and Csp6I.

The fragmented DNA may then be ligated to adaptor oligonucleotides in order to facilitate subsequent enzymatic amplification. The ligation of oligonucleotides to blunt and sticky ended DNA fragments is known in the art, and is carried out by means of dephosphorylation of the ends (e.g. using calf or shrimp alkaline phosphatase) and subsequent ligation using ligase enzymes (e.g. T4 DNA ligase) in the presence of dATPs. The adaptor oligonucleotides are typically at least 18 base pairs in length.

In the third step, the DNA (or fragments thereof) is then digested with one or more methylation sensitive restriction enzymes. The digestion is carried out such that hydrolysis of the DNA at the restriction site is informative of the methylation status of a specific CpG dinucleotide of at least one gene selected from the group consisting of RASSF2A; TFAP2E; HIST1H4K & GSTPi.

Preferably a plurality of genes (herein also referred to as a "gene panel") are analysed. Preferably 2, 3 or 4 genes are analysed. In one embodiment of the method said panel comprises at least one gene selected from the group consisting of RASSF2A; TFAP2E; HIST1H4K & GSTPi and/or their promotor or regulatory regions. Preferably said group comprises the gene HIST1H4K.

Particularly preferred are the following combinations of genes:
HIST1H4K+RASSF
HIST1H4K+GSTPi Preferably, the methylation-specific restriction enzyme is selected from the group consisting of Bsi EI, Hga I HinP1, Hpy99I, Ava I, Bce AI, Bsa HI, BisI, BstUI, Bsh1236I, AccII, BstFNI, McrBC, GlaI, MvnI, HpaII (HapII), HhaI, AciI, SmaI, HinP1I, HpyCH4IV, EagI and mixtures of two or more of the above enzymes. Preferred is a mixture containing the restriction enzymes BstUI, HpaII, HpyCH4IV and HinP1I.

In the fourth step, which is optional but a preferred embodiment, the restriction fragments are amplified. This is preferably carried out using a polymerase chain reaction, and said amplificates may carry suitable detectable labels as discussed above, namely fluorophore labels, radionuclides and mass labels. Particularly preferred is amplification by means of an amplification enzyme and at least two primers comprising, in each case a contiguous sequence at least 16 nucleotides in length that is complementary to, or hybridizes under moderately stringent or stringent conditions to a sequence selected from the group consisting SEQ ID NO: 1 to SEQ ID NO: 4, and complements thereof. Preferably said contiguous sequence is at least 16, 20 or 25 nucleotides in length. In an alternative embodiment said primers may be complementary to any adaptors linked to the fragments.

In the fifth step the amplificates are detected. The detection may be by any means standard in the art, for example, but not limited to, gel electrophoresis analysis, hybridisation analysis, incorporation of detectable tags within the PCR products, DNA array analysis, MALDI or ESI analysis. Preferably said detection is carried out by hybridisation to at least one nucleic acid or peptide nucleic acid comprising in each case a contiguous sequence at least 16 nucleotides in length that is complementary to, or hybridizes under moderately stringent or stringent conditions to a sequence selected from the group consisting SEQ ID NO: 1 to SEQ ID NO: 4, and complements thereof. Preferably said contiguous sequence is at least 16, 20 or 25 nucleotides in length.

Subsequent to the determination of the methylation state or level of the genomic nucleic acids the presence, absence of prostate cell proliferative disorders, most preferably, prostate carcinoma is deduced based upon the methylation state or level of at least one CpG dinucleotide sequence of SEQ ID NO: 1 to SEQ ID NO: 4, or an average, or a value reflecting an average methylation state of a plurality of CpG dinucleotide sequences of SEQ ID NO: 1 to SEQ ID NO: 4 wherein methylation is associated with the presence of prostate cell proliferative disorders, most preferably, prostate cancer. Wherein said methylation is determined by quantitative means the cut-off point for determining said the presence of methylation is preferably zero (i.e. wherein a sample displays any degree of methylation it is determined as having a methylated status at the analysed CpG position). Nonetheless, it is foreseen that the person skilled in the art may wish to adjust said cut-off value in order to provide an assay of a particularly preferred sensitivity or specificity. Accordingly said cut-off value may be increased (thus increasing the specificity), said cut off value may be within a range selected form the group consisting of 0%-5%, 5%-10%, 10%-15%, 15%-20%, 20%-30% and 30%-50%. Particularly preferred are the cut-offs 10%, 15%, 25%, and 30%.

Kits

Moreover, an additional aspect of the present invention is a kit comprising: a means for determining methylation of at least one gene selected from the group consisting of RASSF2A; TFAP2E; HIST1H4K & GSTPi. The means for determining said methylation comprise preferably a bisulfite-containing reagent; one or a plurality of oligonucleotides consisting whose sequences in each case are identical, are complementary, or hybridise under stringent or highly stringent conditions to a 9 or more preferably 18 base long segment of a sequence selected from SEQ ID NO: 5 to SEQ ID NO: 20; and optionally instructions for carrying out and evaluating the described method of methylation analysis. In one embodiment the base sequence of said oligonucleotides comprises at least one CpG, CpA or TpG dinucleotide.

In a further embodiment, said kit may further comprise standard reagents for performing a CpG position-specific methylation analysis, wherein said analysis comprises one or more of the following techniques: MS-SNuPE, MSP, MethyLight™, HeavyMethyl, COBRA, and nucleic acid sequencing. However, a kit along the lines of the present invention can also contain only part of the aforementioned components.

In a preferred embodiment the kit may comprise additional bisulfite conversion reagents selected from the group consisting: DNA denaturation buffer; sulfonation buffer;

DNA recovery reagents or kits (e.g., precipitation, ultrafiltration, affinity column); desulfonation buffer; and DNA recovery components.

In a further alternative embodiment, the kit may contain, packaged in separate containers, a polymerase and a reaction buffer optimised for primer extension mediated by the polymerase, such as PCR. In another embodiment of the invention the kit further comprising means for obtaining a biological sample of the patient. Preferred is a kit, which further comprises a container suitable for containing the means for determining methylation of at least one gene selected from the group consisting of RASSF2A; TFAP2E; HIST1H4K & GSTPi in the biological sample of the patient, and most preferably further comprises instructions for use and interpretation of the kit results. In a preferred embodiment the kit comprises: (a) a bisulfite reagent; (b) a container suitable for containing the said bisulfite reagent and the biological sample of the patient; (c) at least one set of primer oligonucleotides containing two oligonucleotides whose sequences in each case are identical, are complementary, or hybridise under stringent or highly stringent conditions to a 9 or more preferably 18 base long segment of a sequence selected from SEQ ID NO: 5 to SEQ ID NO: 20; and optionally (d) instructions for use and interpretation of the kit results. In an alternative preferred embodiment the kit comprises: (a) a bisulfite reagent; (b) a container suitable for containing the said bisulfite reagent and the biological sample of the patient; (c) at least one oligonucleotides and/or PNA-oligomer having a length of at least 9 or 16 nucleotides which is identical to or hybridises to a pre-treated nucleic acid sequence according to one of SEQ ID NO: 5 to SEQ ID NO: 20 and sequences complementary thereto; and optionally (d) instructions for use and interpretation of the kit results.

In an alternative embodiment the kit comprises: (a) a bisulfite reagent; (b) a container suitable for containing the said bisulfite reagent and the biological sample of the patient; (c) at least one set of primer oligonucleotides containing two oligonucleotides whose sequences in each case are identical, are complementary, or hybridise under stringent or highly stringent conditions to a 9 or more preferably 18 base long segment of a sequence selected from SEQ ID NO: 5 to SEQ ID NO: 20; (d) at least one oligonucleotides and/or PNA-oligomer having a length of at least 9 or 16 nucleotides which is identical to or hybridises to a pre-treated nucleic acid sequence according to one of SEQ ID NO: 5 to SEQ ID NO: 20 and sequences complementary thereto; and optionally (e) instructions for use and interpretation of the kit results.

The kit may also contain other components such as buffers or solutions suitable for blocking, washing or coating, packaged in a separate container.

Another aspect of the invention relates to a kit for use in determining the presence of and/or diagnosing prostate cell proliferative disorders, most preferably prostate carcinoma, said kit comprising: a means for measuring the level of transcription of at least one gene selected from the group consisting of RASSF2A; TFAP2E; HIST1H4K & GSTPi and a means for determining methylation of at least one gene selected from the group consisting of RASSF2A; TFAP2E; HIST1H4K & GSTPi.

Typical reagents (e.g., as might be found in a typical COBRA™-based kit) for COBRA™ analysis may include, but are not limited to: PCR primers for at least one gene selected from the group consisting of RASSF2A; TFAP2E; HIST1H4K & GSTPi; restriction enzyme and appropriate buffer; gene-hybridization oligo; control hybridization oligo; kinase labeling kit for oligo probe; and labeled nucleotides. Typical reagents (e.g., as might be found in a typical MethyLight™-based kit) for MethyLight™ analysis may include, but are not limited to: PCR primers for the bisulfite converted sequence of the at least one gene selected from the group consisting of RASSF2A; TFAP2E; HIST1H4K & GSTPi; bisulfite specific probes (e.g. TaqMan™ or Lightcycler™); optimized PCR buffers and deoxynucleotides; and Taq polymerase.

Typical reagents (e.g., as might be found in a typical Ms-SNuPE™-based kit) for Ms-SNuPE™ analysis may include, but are not limited to: PCR primers for specific gene (or bisulfite treated DNA sequence or CpG island); optimized PCR buffers and deoxynucleotides; gel extraction kit; positive control primers; Ms-SNuPE™ primers for the bisulfite converted sequence of at least one gene selected from the group consisting of RASSF2A; TFAP2E; HIST1H4K & GSTPi; reaction buffer (for the Ms-SNuPE reaction); and labelled nucleotides. Typical reagents (e.g., as might be found in a typical MSP-based kit) for MSP analysis may include, but are not limited to: methylated and unmethylated PCR primers for the bisulfite converted sequence of at least one gene selected from the group consisting of RASSF2A; TFAP2E; HIST1H4K & GSTPi, optimized PCR buffers and deoxynucleotides, and specific probes.

Moreover, an additional aspect of the present invention is an alternative kit comprising a means for determining methylation of at least one gene selected from the group consisting of RASSF2A; TFAP2E; HIST1H4K & GSTPi, wherein said means comprise preferably at least one methylation specific restriction enzyme; one or a plurality of primer oligonucleotides (preferably one or a plurality of primer pairs) suitable for the amplification of a sequence comprising at least one CpG dinucleotide of a sequence selected from the group consisting of SEQ ID NO: 1 to SEQ ID NO: 4; and optionally instructions for carrying out and evaluating the described method of methylation analysis. In one embodiment the base sequence of said oligonucleotides are identical, are complementary, or hybridise under stringent or highly stringent conditions to an at least 18 base long segment of a sequence selected from the group consisting of SEQ ID NO: 1 to SEQ ID NO: 4.

In a further embodiment said kit may comprise one or a plurality of oligonucleotide probes for the analysis of the digest fragments, preferably said oligonucleotides are identical, are complementary, or hybridise under stringent or highly stringent conditions to an at least 16 base long segment of a sequence selected from the group consisting of SEQ ID NO: 1 to SEQ ID NO: 4.

In a preferred embodiment the kit may comprise additional reagents selected from the group consisting: buffer (e.g. restriction enzyme, PCR, storage or washing buffers); DNA recovery reagents or kits (e.g., precipitation, ultrafiltration, affinity column) and DNA recovery components.

In a further alternative embodiment, the kit may contain, packaged in separate containers, a polymerase and a reaction buffer optimised for primer extension mediated by the polymerase, such as PCR. In another embodiment of the invention the kit further comprising means for obtaining a biological sample of the patient. In a preferred embodiment the kit comprises: (a) a methylation sensitive restriction enzyme reagent; (b) a container suitable for containing the said reagent and the biological sample of the patient; (c) at least one set of oligonucleotides one or a plurality of nucleic acids or peptide nucleic acids which are identical, are complementary, or hybridise under stringent or highly stringent conditions to an at least 9 base long segment of at least one sequence selected from the group consisting of SEQ ID NO: 1 to SEQ ID NO: 4; and optionally (d) instructions for use and interpretation of the kit results.

In an alternative preferred embodiment the kit comprises: (a) a methylation sensitive restriction enzyme reagent; (b) a container suitable for containing the said reagent and the biological sample of the patient; (c) at least one set of primer oligonucleotides suitable for the amplification of a sequence comprising at least one CpG dinucleotide of a sequence selected from the group consisting of SEQ ID NO: 1 to SEQ ID NO: 4; and optionally (d) instructions for use and interpretation of the kit results.

In an alternative embodiment the kit comprises: (a) a methylation sensitive restriction enzyme reagent; (b) a container suitable for containing the said reagent and the biological sample of the patient; (c) at least one set of primer oligonucleotides suitable for the amplification of a sequence comprising at least one CpG dinucleotide of a sequence selected from the group consisting of SEQ ID NO: 1 to SEQ ID NO: 4; (d) at least one set of oligonucleotides one or a plurality of nucleic acids or peptide nucleic acids which are identical, are complementary, or hybridise under stringent or highly stringent conditions to an at least 9 base long segment of a sequence selected from the group consisting of SEQ ID NO: 1 to SEQ ID NO: 4 and optionally (e) instructions for use and interpretation of the kit results.

The kit may also contain other components such as buffers or solutions suitable for blocking, washing or coating, packaged in a separate container.

The invention further relates to a kit for use in providing a diagnosis of the presence of prostate cell proliferative disorders, most preferably, prostate carcinoma in a subject by means of methylation-sensitive restriction enzyme analysis. Said kit comprises a container and a DNA microarray component. Said DNA microarray component being a surface upon which a plurality of oligonucleotides are immobilized at designated positions and wherein the oligonucleotide comprises at least one CpG methylation site. At least one of said oligonucleotides is specific for at least one gene selected from the group consisting of RASSF2A; TFAP2E; HIST1H4K & GSTPi and comprises a sequence of at least 15 base pairs in length but no more than 200 bp of a sequence selected from the group consisting of SEQ ID NO: 1 to SEQ ID NO: 4. Preferably said sequence is at least 15 base pairs in length but no more than 80 bp of a sequence selected from the group consisting of SEQ ID NO: 1 to SEQ ID NO: 4. It is further preferred that said sequence is at least 20 base pairs in length but no more than 30 bp of a sequence selected from the group consisting of SEQ ID NO: 1 to SEQ ID NO: 4.

Said test kit preferably further comprises a restriction enzyme component comprising one or a plurality of methylation-sensitive restriction enzymes.

In a further embodiment said test kit is further characterized in that it comprises at least one methylation-specific restriction enzyme, and wherein the oligonucleotides comprise a restriction site of said at least one methylation specific restriction enzymes.

The kit may further comprise one or several of the following components, which are known in the art for DNA enrichment: a protein component, said protein binding selectively to methylated DNA; a triplex-forming nucleic acid component, one or a plurality of linkers, optionally in a suitable solution; substances or solutions for performing a ligation e.g. ligases, buffers; substances or solutions for performing a column chromatography; substances or solutions for performing an immunology based enrichment (e.g. immunoprecipitation); substances or solutions for performing a nucleic acid amplification e.g. PCR; a dye or several dyes, if applicable with a coupling reagent, if applicable in a solution; substances or solutions for performing a hybridization; and/or substances or solutions for performing a washing step.

The described invention further provides a composition of matter useful for detecting, or for diagnosing prostate carcinoma. Said composition comprising at least one nucleic acid 18 base pairs in length of a segment of the nucleic acid sequence disclosed in SEQ ID NO: 5 to SEQ ID NO: 20, and one or more substances taken from the group comprising: 1-5 mM Magnesium Chloride, 100-500 µM dNTP, 0.5-5 units of taq polymerase, bovine serum albumen, an oligomer in particular an oligonucleotide or peptide nucleic acid (PNA)-oligomer, said oligomer comprising in each case at least one base sequence having a length of at least 9 nucleotides which is complementary to, or hybridizes under moderately stringent or stringent conditions to a pretreated genomic DNA according to one of the SEQ ID NO: 5 to SEQ ID NO: 20 and sequences complementary thereto. It is preferred that said composition of matter comprises a buffer solution appropriate for the stabilization of said nucleic acid in an aqueous solution and enabling polymerase based reactions within said solution. Suitable buffers are known in the art and commercially available.

In further preferred embodiments of the invention said at least one nucleic acid is at least 50, 100, 150, 200, 250 or 500 base pairs in length of a segment of the nucleic acid sequence disclosed in SEQ ID NO: 5 to SEQ ID NO: 20.

While the present invention has been described with specificity in accordance with certain of its preferred embodiments, the following examples serve only to illustrate the invention and are not intended to limit the invention within the principles and scope of the broadest interpretations and equivalent configurations thereof.

Example 1

The aim of the present study was to determine the feasibility of measuring DNA methylation markers for prostate cancer (hereinafter also referred to as PCa) in remote body fluids. In this process a high quality workflow flow for urine was utilized, candidate markers were analysed by HeavyMethyl™ (HM) technology (Cottrell et al., Nucleic Acids Res. 2004 Jan. 13; 32(1):e10.) and it was demonstrated that PCa sheds DNA that can be detected by means of methylation analysis in both plasma and urine with high sensitivity. It was thus established that the analysed markers were suitable for the development of a screening test for PCa based on DNA methylation analysis.

Study Objectives

The purpose of the present study was to conduct an investigation into whether DNA methylation markers of PCa can be measured in a remote body fluid. The study was designed to identify the optimal analyte for such a test and to generate specificity and analytical performance data for marker candidates.

Candidate Markers and Location of Assays

The markers RASSF2 and TFAP2E were identified on the basis of their methylation in prostate cancer tissues, as determined in a preliminary study (not described herein). The markers GSTPi and HIST1H4K had been previously identified in a study by the applicant as published in patent application WO 2005/054517.

Methylation analysis was performed by means of the HeavyMethyl™. Isolated genomic is bisulfite treated to convert non-methylated cytosines to uracil, wherein methylated cyclosines are conserved. Fragments of the bisulfite treated DNA comprising potentially methylated CpG dinucleotides are then amplified by means of PCR. The primers do not cover any potentially methylated cytosine positions (i.e. do not hybridise to genomic CpG dinucleotides). Amplification of fragments comprising unmethylated CpG dinucleotides is suppressed by means of a blocking oligonucleotide that hybridises to TG dinucleotides. Accordingly only DNA that was methylated in the genomic sample is amplified. Amplificate fragments are detected by means of detectably labelled probes suitable for use in PCR reactions such as RealTime detection probes.

Assay primer and probes are provided in the accompanying sequence listing as according to Table 2.

GSTPi

Chromosomal Location: 11q13

Nearby Gene(s): GSTPi HM forward primer is just upstream of exon 1 and the reverse primer is just downstream of exon 1 of GSTP1

RASSF2A

Chromosomal Location: 20pter-p12.1

Nearby Gene(s): w/i the CpG island of intron 1 of the v. 1 transcript of RASSF2

HIST1H4K

Chromosomal Location: 6p22-21.3

Nearby Gene(s): overlaps intronless HIST1H4K

TFAP2E

Chromosomal Location: 1p34.3

Nearby Gene(s): w/i intron 3 of TFAP2E (~11 kb downstream of txn start) and ~20 kb upstream of KIAA0319L txn start (PKD-1 like gene)

Tissue Study

Assay were initially tested in normal tissues, NAT and PCa. The marker candidates that were analysed in the HM tissue test were all very specific for normal blood and normal prostate tissue. In contrast to previous studies it was observed that DNA from prostate normal adjacent tumor (NAT) is nearly as methylated as prostate tumor DNA. NAT (which may contain BPH) is clearly distinct from BPH tissue that has been derived from non-prostate-tumor-bearing patients without elevated PSA (the origin of many BPH tissue samples in the MSP tissue test). In fact, there is evidence in the literature that GSTPI in NAT is methylated (Hanson et al., 2006).

Performance of the markers in normal+BPH as compared to PCa is provided in Table 3 and FIG. 1.

Remote Analyte Analysis

In order to maximize the analyte equivalent in real-time PCR assays (1.5 ml equivalents), the maximum number of assays in the study was capped at four, with each assay run in duplicate for each sample.

Sample Collection

For this study, we collected matched plasma and urine from a total of 191 men, including 91 males with biopsy-confirmed prostate cancer, 51 males with no cancer detected by biopsy (subsequently diagnosed with BPH), and 50 young healthy males. In all analyses, the positive class is comprised of the PCa samples.

In designing the present study, the definition of the negative class was an issue as there is no detection method that excludes presence of PCa with 100% certainty. Biopsy has a false negative diagnosis rate of at least 10% (Djavan et al., 2000; Mian et al., 2002; Gupta et al., 2005; Hanley et al., 2006) while PSA measurement is prone to both false negatives and false positives. Because the primary objective of the study was to demonstrate the feasibility of measuring methylated markers of PCa in a remote body fluid, we focused on a negative class that minimized the probability of false positives. Consequently, young healthy males were chosen as the "true" negative class. It was reasoned that young healthy males with no family history of prostate cancer should be truly negative for PCa.

Because one embodiment of the PCa test is as a diagnostic follow-on to PSA, we also included a second negative class of biopsy negative, BPH samples. A potentially confounding factor in this class is the likely presence of false negative biopsies.

In five PCa cases, only a plasma sample was collected and in ten additional cases only a urine sample was collected. The samples were collected at multiple sites. The urine was collected after a prostatic massage, both plasma and urine samples were obtained before any treatment for PCa. Inclusion and exclusion criteria were designed to ensure that the patients analysed reflect the potential patients who would use PCa screening tests.

The following inclusion and exclusion criteria applied to the patients undergoing biopsy:

Inclusion Criteria:

Indication for biopsy (elevated PSA and/or suspicious DRE)

Biopsy scheduled within 1 week after sample collection

Age 40-80

Exclusion Criteria:

Any prior treatment for prostate cancer

History of cancer or serious illness in the past 5 years

Symptoms of urinary tract infection

The following criteria applied to the healthy men of the control group:

Inclusion Criteria:

Male

Age 18-30

Exclusion Criteria:

Any prior treatment for or symptoms of prostate cancer or prostate disease

History of cancer or serious illness in the past 5 years

Symptoms of urinary tract infection

Patient data and tumor characteristics

The Gleason score (where appropriate) of the patient samples are listed Table 4. The mean PSA values for the prostate cancer, HGPIN and biopsy negative samples were 18.2±33.1, 7.0±3.0 and 8.8±5.2 respectively. The prostate cancer, HGPIN and biopsy negative classes were diagnosed after sample collection via prostate biopsy. The mean number of biopsy cores for all sample classes was 8, although there was some variation between providers.

DNA extraction and bisulfite treatment was carried out according to standardised protocols. For each assay, 1.5 ml analyte equivalent was run in duplicate.

Marker Performance, General Considerations

The initial objective of the study was to develop a panel of markers targeted as a diagnostic follow-on to PSA tests of 2.5 ng/ml or more for men over 50 years of age to discriminate prostate cancer from non-cancerous conditions. Such a test could be further expanded as a more specific prostate cancer screening test that would compete with PSA testing because of superior performance. In the present study we analysed the data in two different ways: (i) we used prostate cancer and biopsy-negative samples to assess markers performance in the follow-on to PSA test (diagnostic application) and (ii) we used prostate cancer and all the non-cancer (biopsy-negative and healthy) samples to measure markers performance in screening test (screening application). We report marker performance for plasma and urine separately, we also provide data analysis for individual markers and marker panels. All data are reported as logmean raw methylation values.

As a primary screening test, the marker panel would preferably identify PCa in men over age 50 years with improved specificity relative to PSA. All screening application analyses use the PCa samples as the positive class. For the purposes of the present study, we analysed data for the screening application with two alternative negative classes. The first negative class analysed the 50 young healthy males with minimal likelihood of undetected PCa. While this negative class represents a "true" test negative, it is not age-matched to the target PCa screening population and does not include any likely false positive classes, e.g. BPH. Therefore, we performed a second analysis in which all 50 healthy young controls and all 51 biopsy negative controls were analysed as a 101 sample size negative class.

On average, approximately 20,000,000 PSA tests are performed every year in the US with only approximately 1,000,000 cases moving forward to biopsy (of which approximately 750,000 biopsies are unnecessary). Therefore, less than 5% of individuals that are currently screened by PSA fall in the negative class that is represented by elevated-PSA-BPH-positive whereas as the vast majority of the target screening population fall into the PSA-low negative class. Whereas the negative class of only healthy young males may represent an overestimation of the discriminatory capacity of our markers, the combined negative class of healthy young males plus age-matched biopsy negative males may represent an underestimation of the discriminatory capacity of our markers.

Figure 2:
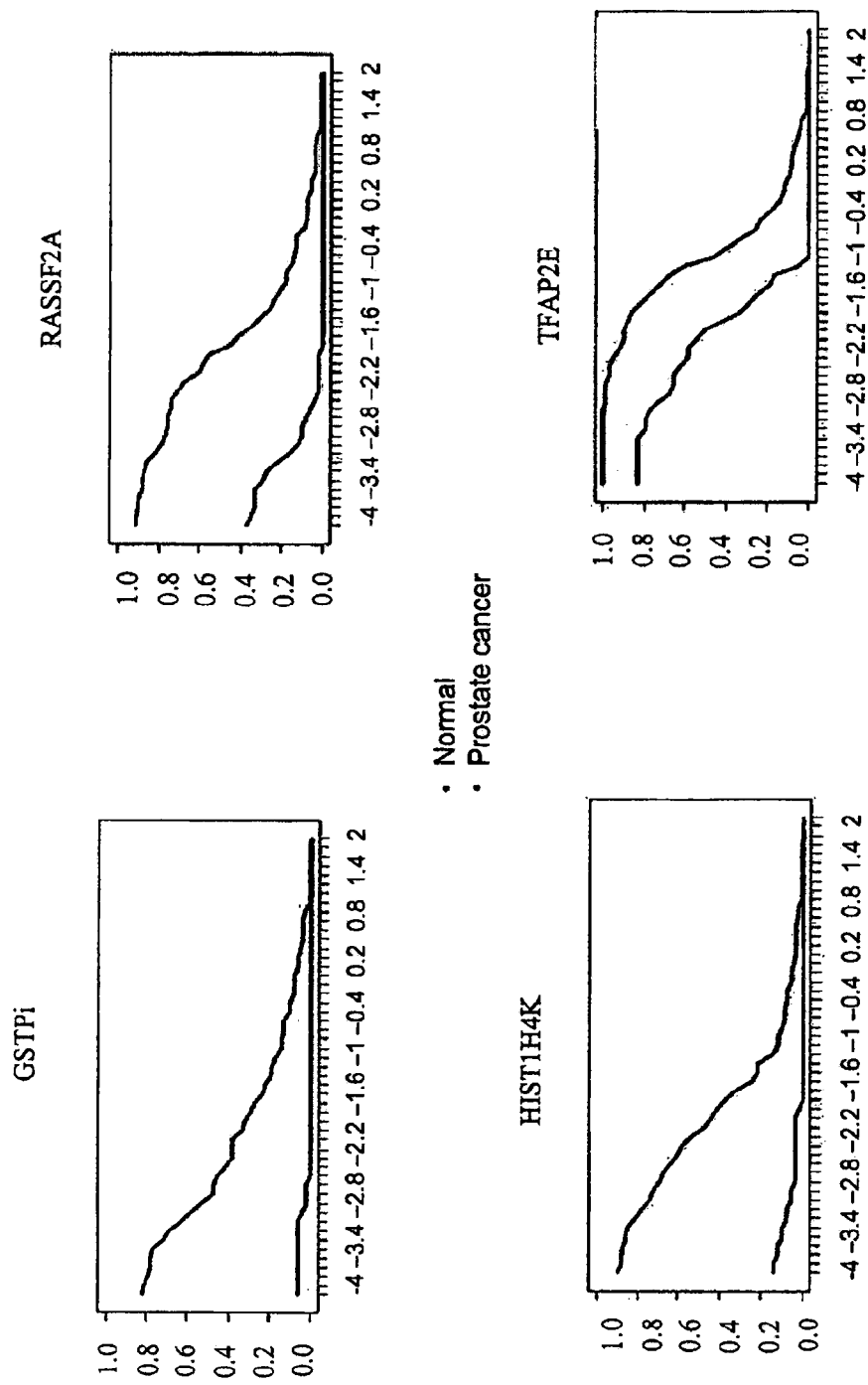
FIG. 2 provides an overview of the log mean methylation measured by means of HM real-time PCR assays of post-prostatic massage urine of PCa and negative class I (healthy individuals) according to Example 1. For each analysed gene (as labeled above each plot), sensitivity is shown on the Y-axis, DNA methylation measured in (log 10 ng/mL) is shown on the X-axis.
Figure 3:
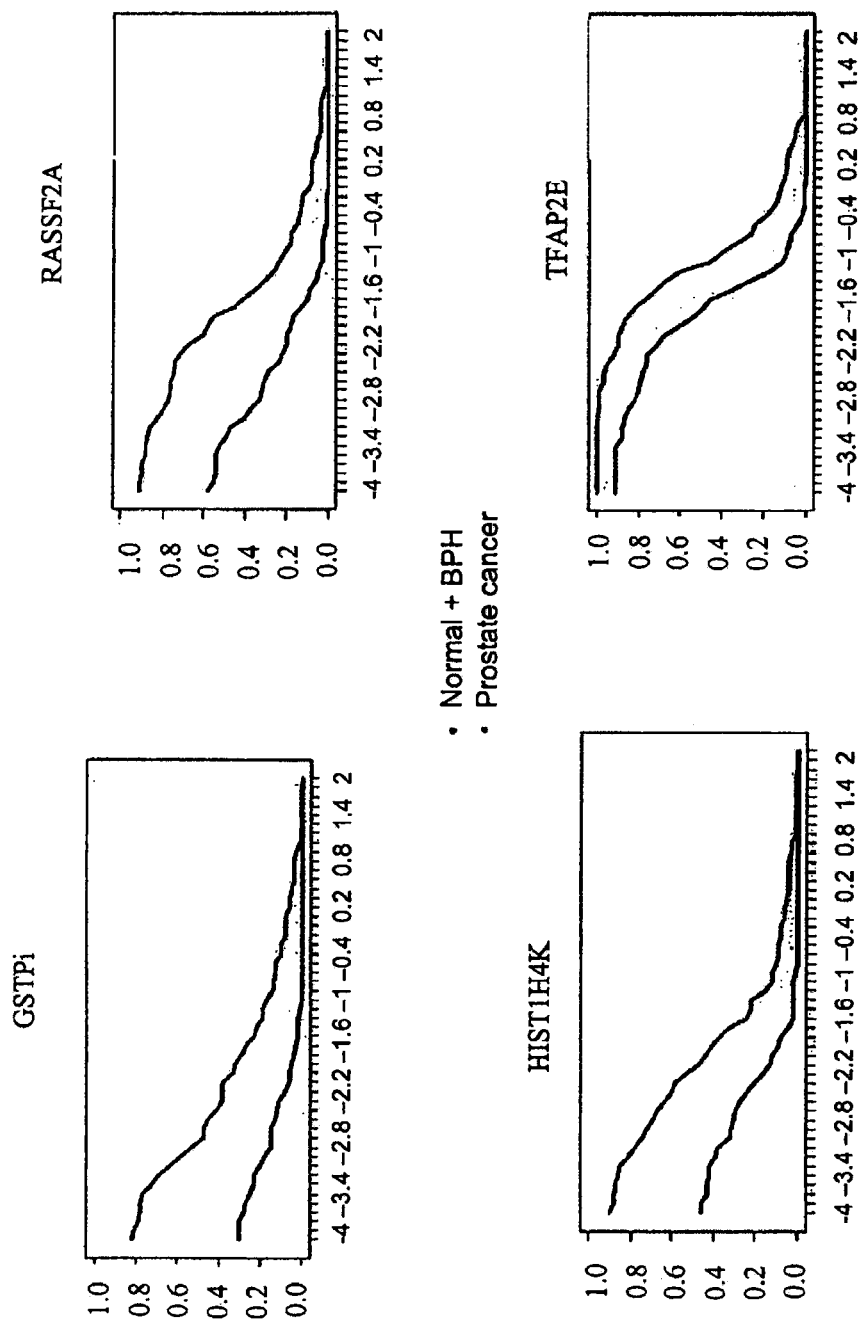
FIG. 3 provides an overview of the log mean methylation measured by means of HM real-time PCR assays of post-pro static massage urine of PCa and negative class II (healthy plus biopsy negative individuals) according to Example 1. For each analysed gene (as labeled above each plot), sensitivity is shown on the Y-axis, DNA methylation measured in (log 10 ng/mL) is shown on the X-axis.

Sensitivity and specificity of individual (single) markers tested by real-time PCR in post-prostatic massage urine from prostate cancer patients vs. biopsy negative patients and healthy control individuals is shown in Table 5. FIG. 2 shows the HM real-time PCR assays of post-prostatic massage urine of PCa and negative class I (healthy individuals). FIG. 3 shows the HM real-time PCR assays of post-prostatic massage urine of PCa and negative class II (healthy plus biopsy negative individuals).

Figure 4:
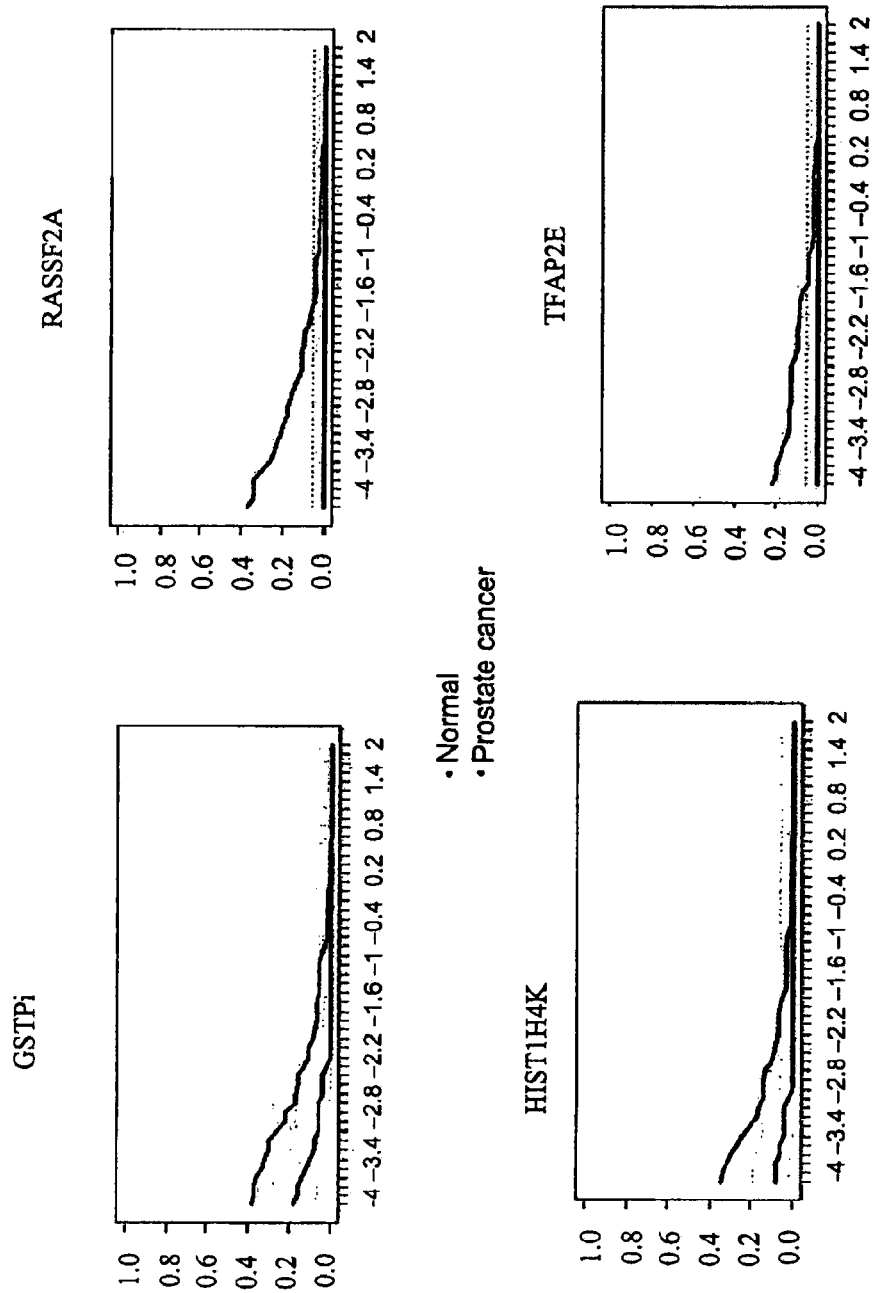
FIG. 4 shows the log mean methylation measured by means of HM real-time PCR assays of plasma of PCa and negative class I (healthy individuals). For each analysed gene (as labeled above each plot), sensitivity is shown on the Y-axis, DNA methylation measured in (log 10 ng/mL) is shown on the X-axis.
Figure 5:
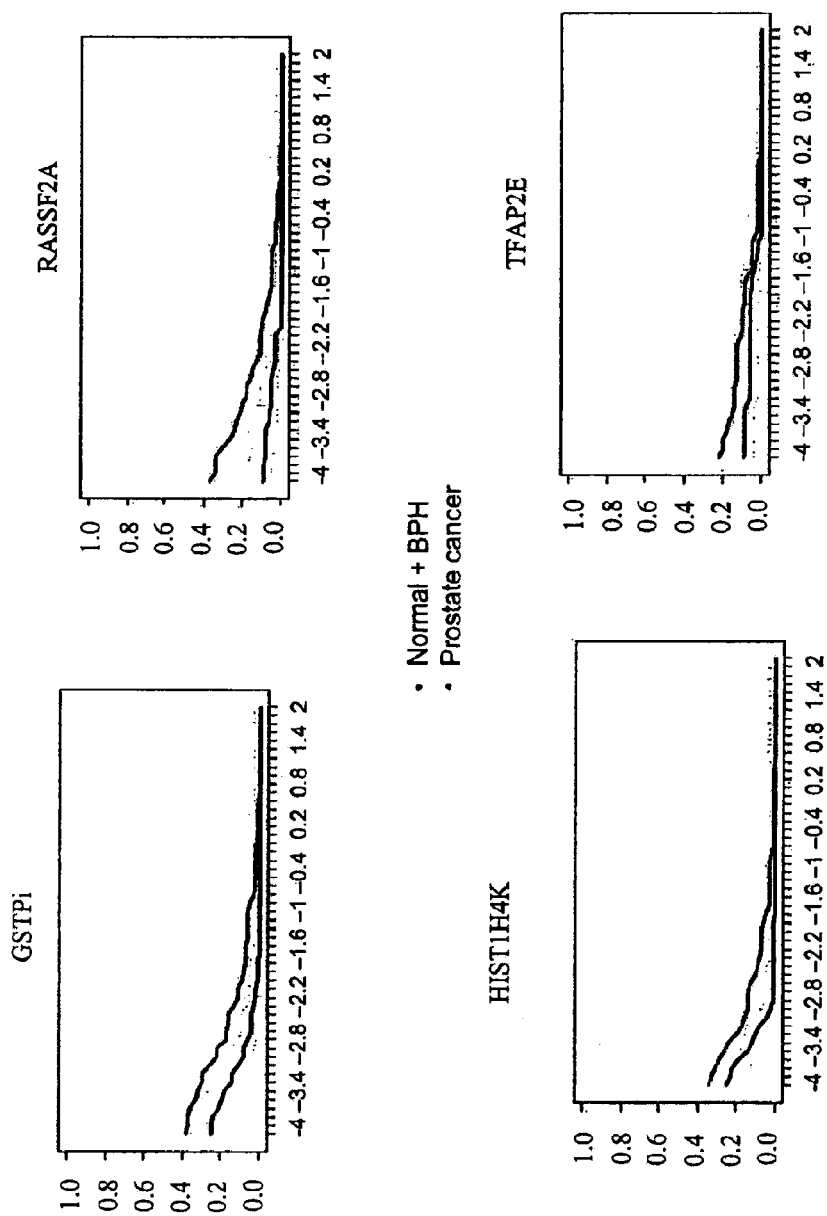
FIG. 5 shows the log mean methylation measured by means of HM real-time PCR assays of plasma of PCa and negative class II (healthy plus biopsy negative individuals). For each analysed gene (as labeled above each plot), sensitivity is shown on the Y-axis, DNA methylation measured in (log 10 ng/mL) is shown on the X-axis.

Sensitivity and specificity of individual (single) markers tested by real-time PCR in plasma from prostate cancer patients vs. biopsy negative patients and healthy control individualism shown in Table 6. FIG. 4 shows the HM real-time PCR assays of plasma of PCa and negative class I (healthy individuals). FIG. 5 shows the HM real-time PCR assays of plasma of PCa and negative class II (healthy plus biopsy negative individuals).

As illustrated in Table 7, in all negative class comparisons and for all markers, urine was the more sensitive analyte.

Correlation of Markers with Gleason Score

Increasing amounts of methylated marker DNA correlated with increasing Gleason score for all markers in plasma. This was true for samples with high amounts of methylated marker DNA in urine (see especially markers TFAP2E and RASSF2A), but in general the correlation was less strong in DNA from urine than in DNA from plasma. PSA as a marker of PCa in patients with elevated PSA (>4 ng/ml) also correlated with increasing Gleason score.

Performance of screening marker panels to distinguish PCa from negative class I (healthy males) in urine is provided in Table 8.

Performance of screening marker panels to distinguish PCa from negative class II (healthy males plus biopsy negative) in urine is provided in Table 9.

Performance of screening marker panels to distinguish PCa from negative class I (healthy males) in plasma is provided in Table 10.

Performance of screening marker panels to distinguish PCa from negative class II (healthy males plus biopsy negative) in plasma is provided in Table 11.

Marker Performance in Diagnostic Application: Follow-on to PSA

As a diagnostic follow-on to PSA testing, the markers would preferably identify PCa in men over age 50 years who have been classified as high-risk individuals due to elevated PSA (>2.5 ng/ml). This is a distinct application and analysis and requires increased discrimination as compared to the screening test. False positives in this application arise from the elevated PSA, biopsy negative BPH class. Again, the PCa samples represent the positive class. For the purposes of a diagnostic follow-on application, we analysed the data using a single negative class comprised of the 51 biopsy negative samples. AUC of markers tested by real-time PCR in post-prostatic massage urine and plasma from prostate cancer patients and biopsy negative patients is provided in Table 12.

From said table it can be seen that for all methylation markers analysed, urine was the more sensitive analyte. For total PSA (treated here as an additional marker to determine if there is any further information provided past the >4 ng/ml indication for biopsy), there was no difference in sensitivity between urine and plasma.

Performance of Marker Panels

In order to provide improved accuracy, combinations of markers were assessed both qualitatively and quantitatively.

Table 13 provides the performance of diagnostic marker panels to distinguish PCa from biopsy negative in urine.

Table 14 provides the performance of diagnostic marker panels to distinguish PCa from biopsy negative in plasma.

Discussion

The study was conducted on plasma and/or urine samples collected from 91 PCa patients, 51 biopsy-negative patients (diagnosed with BPH) and 50 young healthy males. HM™ real-time PCR assays were used to measure DNA methylation of the candidate markers. The amount of methylated marker DNA was correlated with PCa in both plasma and urine, with urine DNA showing greater sensitivity. As a screening test (discrimination of PCa cancer from healthy controls using urine analyte), anchor marker candidates GSTPi, RASSF2A, HIST1H4K and TFAP2E have 63%, 74%, 69% and 47% sensitivity at 96% specificity respectively. As a diagnostic follow-on to PSA test (discrimination of PCa from biopsy negative controls, all with elevated PSA), the markers have 23%, 18%, 28% & 23% sensitivity at 95% specificity, respectively. A quantitative screening panel of markers RASSF2A and HIST1H4K yielded 94% sensitivity at 88% specificity against healthy individuals. A quantitative diagnostic panel of markers GSTPi and PSA yielded 83% sensitivity at 45% specificity. The performance of these markers compare well with the performance of PSA (18% sensitivity at 98% specificity for men <60 years and 19% sensitivity at 94% specificity for men >60 years) in the screening population (Punglia et al., 2003). Methylation of all markers correlated well with Gleason score in plasma DNA, but the correlation was less strong in urine DNA.

CONCLUSIONS

At the completion of the present investigation, it was demonstrated that prostate cancer biomarkers based on methylated DNA can be measured in plasma and urine, with urine DNA showing greater sensitivity than plasma. Additionally, DNA methylation markers that discriminate PCa patients from healthy controls and those with benign prostatic hyperplasia (BPH) were identified. The major conclusions of the present study are as follows:

Methylated markers of prostate cancer can be measured in both plasma and urine from PCa patients.

Identification of markers that discriminate PCa patients from those without PCa.

TABLE 1

Genes and sequences according to the present invention

| Gene | Genomics SEQ ID NO: | Methylated bisulfite converted sense strand | Methylated bisulfite converted antisense strand | Unmethylated bisulfite converted sense strand | Unmethylated bisulfite converted antisense strand |
|---|---|---|---|---|---|
| RASSF2A | 1 | 5 | 6 | 13 | 14 |
| TFAP2E | 2 | 7 | 8 | 15 | 16 |
| HIST1H4K | 3 | 9 | 10 | 17 | 18 |
| GSTPi | 4 | 11 | 12 | 19 | 20 |

TABLE 2

Assay components according to Example 1

| Gene | Forward Primer | Reverse Primer | Blocker | Detection Oligo |
|---|---|---|---|---|
| GSTPi | 21 | 22 | 23 | 24 |
| HIST1H4K | 25 | 26 | 27 | 28 |
| RASSF2A | 29 | 30 | 31 | 32 |
| TFAP2E | 33 | 34 | 35 | 36 |

TABLE 3

Performance analysis of markers (normal plus BPH vs. PCa) in tissue test according to Example 1.

| Marker | AUC | Sensitivity | Specificity |
|---|---|---|---|
| GSTPi | 0.90 | 0.83 | 0.91 |
| HIST1H4K | 0.91 | 0.83 | 0.91 |
| RASSF2A | 0.93 | 0.75 | 0.91 |
| TFAP2E | NA | NA | NA |

TABLE 4

Remote samples according to Example 1.

| Sample type | No. of samples |
|---|---|
| Prostate Cancer | |
| Gleason Score | |
| 4 | 1 |
| 5 | 5 |
| 6 | 33 |
| 7 | 39 |
| 8 | 8 |
| 9 | 4 |
| No score available | 1 |
| Total Prostate Cancer: | 91 |
| Biopsy Negative | 51 |
| Healthy Control | 50 |

TABLE 5

Sensitivity and specificity of individual markers tested by real-time PCR in post-prostatic massage urine from prostate cancer patients, biopsy negative patients and healthy control individuals.

| | Negative Class I: Healthy | | | Negative Class II: Healthy + Biopsy (−) | | |
|---|---|---|---|---|---|---|
| Marker | AUC | Sens/Spec | Wilcoxon p value | AUC | Sens/Spec | Wilcoxon p value |
| GSTPi | 0.89 | 0.63/0.96 | 0 | 0.79 | 0.31/0.96 | 0 |
| RASSF2 A | 0.90 | 0.74/0.96 | 0 | 0.79 | 0.24/0.96 | 0 |
| HIST1H4K | 0.91 | 0.69/0.96 | 0 | 0.77 | 0.36/0.96 | 0 |
| TFAP2E | 0.86 | 0.47/0.96 | 0 | 0.77 | 0.27/0.96 | 0 |

TABLE 6

Sensitivity and specificity of individual markers tested by real-time PCR in plasma from prostate cancer patients, biopsy negative patients and healthy control individuals.

| | Negative Class I: Healthy | | | Negative Class II: Healthy + Biopsy (−) | | |
|---|---|---|---|---|---|---|
| Marker | AUC | Sens/Spec | Wilcoxon p value | AUC | Sens/Spec | Wilcoxon p value |
| GSTPi/GSTPI | 0.61 | 0.17/0.96 | 0.0063 | 0.58 | 0.17/0.95 | 0.0183 |
| RASSF2 A | 0.68 | 0.37/1.00 | 0 | 0.64 | 0.20/0.95 | 0 |
| HIST1H4K | 0.64 | 0.26/0.96 | $5e^{-04}$ | 0.56 | 0.16/0.95 | 0.0572 |
| TFAP2E | 0.61 | 0.22/1.00 | $4e^{-04}$ | 0.56 | 0.09/0.95 | 0.0128 |

TABLE 7

| | Negative Class I: Healthy | | Negative Class II: Healthy + Biopsy (−) | |
|---|---|---|---|---|
| Marker | Urine AUC | Plasma AUC | Urine AUC | Plasma AUC |
| GSTPi/GSTPI | 0.89 | 0.61 | 0.69 | 0.55 |
| RASSF2 A | 0.90 | 0.68 | 0.66 | 0.60 |
| HIST1H4 K | 0.91 | 0.64 | 0.64 | 0.50 |
| TFAP2E | 0.86 | 0.61 | 0.65 | 0.52 |

TABLE 8

Performance of screening marker panels to distinguish PCa from negative class I (healthy males) in urine

| Marker Panel | % Sens PCa | % Spec Healthy |
|---|---|---|
| Quantitative Single Markers: | | |
| RASSF2A | 74 | 96 |
| HIST1H4K | 69 | 96 |
| GSTPi | 63 | 96 |
| TFAP2E | 46 | 100 |
| Qualitative Panels: | | |
| GSTPi + HIST1H4K | 79 | 98 |
| RASSF2 A + HIST1H4K | 94 | 88 |
| Quantitative Panels: | | |
| RASSF2A + HIST1H4K | 94 | 88 |
| quadSVM (all markers, no PSA) | 79 | 98 |

TABLE 9

| Marker Panel | % Sens PCa | % Spec Healthy + Biopsy (−) |
|---|---|---|
| Quantitative Single Markers: | | |
| RASSF2A | 74 | 76 |
| HIST1H4K | 69 | 68 |
| GSTPi | 63 | 80 |
| TFAP2E | 46 | 88 |
| Qualitative Panels: | | |
| GSTPi + HIST1H4K | 79 | 72 |
| RASSF2 A + HIST1H4K | 94 | 54 |
| Quantitative Panels: | | |
| RASSF2 A + HIST1H4K | 94 | 58 |
| quadSVM (all markers, no PSA) | 79 | 76 |

TABLE 10

Performance of screening marker panels to distinguish PCa from negative class I (healthy males) in plasma

| Marker Panel | % Sens PCa | % Spec Healthy |
|---|---|---|
| Quantitative Single Markers: | | |
| RASSF2A | 37 | 100 |
| HIST1H4K | 26 | 96 |
| GSTPi | 17 | 94 |
| TFAP2E | 22 | 100 |
| Qualitative Panels: | | |
| RASSF2A + HIST1H4K | 41 | 98 |
| Quantitative Panels: | | |
| RASSF2A + TFAP2E (TFAP2E used to normalize) | 32 | 100 |
| quadSVM (all markers, no PSA) | 39 | 96 |

TABLE 11

| Marker Panel | % Sens PCa | % Spec Healthy + Biopsy (−) |
|---|---|---|
| Quantitative Single Markers: | | |
| RASSF2A | 37 | 91 |
| HIST1H4K | 26 | 88 |
| GSTPi | 17 | 95 |
| TFAP2E | 22 | 92 |
| Qualitative Panels: | | |
| RASSF2A + HIST1H4K | 41 | 88 |
| Quantitative Panels: | | |
| RASSF2A + TFAP2E (TFAP2E used to normalize) | 32 | 92 |
| quadSVM (all markers, no PSA) | 39 | 94 |

TABLE 12

| Marker | PCa vs. Biopsy (−) Urine AUC | PCa vs. Biopsy (−) Plasma AUC |
|---|---|---|
| GSTPi/GSTPI | 0.69 | 0.55 |
| RASSF2 A | 0.66 | 0.60 |
| HIST1H4 K | 0.64 | 0.50 |
| TFAP2E | 0.65 | 0.52 |
| ***PSA | 0.56 | 0.56 |

***Tests whether PSA contains further information beyond what was contributed by the >4 ng/ml cut-off indication for prostate biopsy.

TABLE 13

| Marker Panel | % Sens PCa | % Spec Biopsy (−) |
|---|---|---|
| Quantitative Single Markers: | | |
| RASSF2A | 74 | 55 |
| HIST1H4K | 69 | 41 |
| GSTPi | 63 | 64 |
| TFAP2E | 46 | 77 |
| Qualitative Panels: | | |
| GSTPi + HIST1H4K | 79 | 46 |
| RASSF2A + HIST1H4K | 94 | 21 |
| Quantitative Panels: | | |
| RASSF2A + HIST1H4K | 94 | 27 |
| GSTPi + PSA | 83 | 45 |
| quadSVM (all markers, no PSA) | 79 | 55 |

TABLE 14

| Marker Panel | % Sens PCa | % Spec Biopsy (−) |
|---|---|---|
| Quantitative Single Markers: | | |
| RASSF2A | 37 | 82 |
| HIST1H4K | 26 | 79 |
| GSTPi | 17 | 96 |
| TFAP2E | 22 | 84 |
| Qualitative Panels: | | |
| RASSF2A + HIST1H4K | 41 | 79 |
| Quantitative Panels: | | |
| RASSF2A + TF AP2E (TFAP2E used to normalize) | 32 | 85 |
| RASSF2A + TFAP2E + PSA (TFAP2E used to normalize) | 94 | 22 |
| quadSVM (all markers, no PSA) | 39 | 91 |
| quadSVM (all markers + PSA) | 48 | 87 |

What is claimed is:

1. A method for detecting methylation of cytosine bases in at least 16 contiguous nucleic acids of SEQ ID NO: 1 from prostate cell genomic DNA from a subject comprising the steps of:
   a) treating the prostate cell genomic DNA which is derived from a biological sample comprising prostate tumor DNA with bisulfite so that unmethylated cytosine bases are converted to uracil while methylated cytosine bases remain unconverted, wherein the prostate cell genomic DNA comprises a sequence of at least 16 contiguous nucleotides of SEQ ID NO: 1 and the 16 contiguous nucleotides comprise at least one CpG dinucleotide;
   b) detecting unconverted cytosine bases in the at least 16 contiguous nucleic acids of SEQ ID NO: 1 by amplification of the treated DNA and subsequent hybridization or sequencing; and
   c) detecting the presence of at least one unconverted cytosine comprised by a CpG dinucleotide in the at least 16 contiguous nucleic acids of SEQ ID NO: 1, wherein the amplification of the treated DNA comprises at least one primer having a length of at least 9 nucleotides and at least one CpG dinucleotide, wherein the primer hybridizes to a nucleic acid sequence selected from the group consisting of SEQ ID NOs: 5, 6, 13 and 14.

2. The method of claim 1, wherein the biological sample is selected from the group consisting of histological slides, biopsies, paraffin embedded tissue, ejaculate, urine, blood plasma, blood serum and whole blood.

3. The method of claim 1, further comprising the use of a blocker oligonucleotide having a length of at least 9 nucleotides and comprising at least one CpG, CpA or TpG dinucleotide, wherein the blocker hybridizes to a nucleic acid sequence selected from the group consisting of SEQ ID NOs: 5, 6, 13 and 14.

* * * * *

SEQUENCE LISTING

<160> NUMBER OF SEQ ID NOS: 36

<210> SEQ ID NO 1
<211> LENGTH: 1920
<212> TYPE: DNA
<213> ORGANISM: Homo Sapiens

<400> SEQUENCE: 1

```
ccaggctgcc gtagacacag cctttgctct cccgaaaaac acgttctagg cgccgggatt      60
ccagatacct gggaaataga gtgcacgcag ctgttgagag gcctcgcgct tggcttctcc     120
tatcactgag gcgcagaggt gctgtggaca gcccagaccc acacggcgcc cgaggtgaaa     180
cagaaccctc agtctcccta tgaggccact ggcactctcg gctgtcccca gagctctccg     240
acttagagct gaatgcaaag taagcgctcg aaatgcagaa gtagccgggg ccgcccacgg     300
cacctgcctc gctcggggcg agagaagacg ccaggctgag gtcccagcga cctcaggcac     360
cagctccgaa ggagggcggg gagaccgcaa aggggaagtg cccggagggc caacggcccc     420
cgcgcaccct gcgcccctct gaagcgcgcc gcctccccgc gccggggact gggacctgcc     480
tctggggaat ccgcctagaa gacgcgcg gactggggtc gggcactctc cagggctgtc     540
aggccctccc cagccctgca cctgccgcgc cgccccacct cgccaggaag tctcagagac     600
cccggggatg gggtgggagc gccttcccat cgcgggctca aaaagaagga aggacgcccc     660
cagggggtcgt agaaggagga ctagctccaa gccacaactt tcttcggacc caaggcaggc     720
cggctggggc tccgcgccta cacggcccct ggcggggtc cgcgcgcccc gggagccccg     780
cggctcgggg aggaaagagg agacaagaga caggcgagga ttacggggct gacccagccg     840
gggtagggac catcgtggaa aaactttggc gaggtggggg gacgcggaaa gagagcggcc     900
cgcgccctgc accttgcgcc gggcatcccg cgccagtgcc tcgctcccag tgccccgcgc     960
cccgcgcccc gcgccttgcc ttcacccccgg gccagctgca tcgcgcccgc gccgcaggaa    1020
ccgtggagtt ggaaagtggg ggcgccgcgg ctgggggct gcttcagctg cgcctcggcc    1080
agcgatcggc gggccgggct caaatccagc caggctgggc aggcggtggc cgcgcgactg    1140
gggaccgggc gccccgccct cctcgctccc ctcctccttc ctctccctcc ctccagcccc    1200
ttggcctttt tcagcccccta ccggatctgc tcgtccgctg tcctctctt tctctcgctc    1260
ttcatatcac tctccacccc ttcgccttgc cttcgccttt cttcctcccc ttgtctcctg    1320
cccccctcctc ttctccccctc ccctctaggg gcggagcttc tccctccct cccagacaat    1380
gctgtggctg cgtcccctc cccgccagct cgtccaggct cccgccgcca gcgattcttc    1440
cgggctgggg gtggggaggt gggggggag tgcagggttg gggaggatga gctggctccc    1500
ctcacctcct tgctgctgcc ctctccaaga gggatggaga cttggcccaa gctcctcggt    1560
tcacccggag ctgtgacagc cactcccagg gaacagtcac gctgccctac caagcccacc    1620
tccagcggcc tggattcccc aggcagaggt tgtgggattt tgttttttct aacatcccag    1680
cttattccca aagggtttg agccggacag gggctaaaca ggccccttcg acttggcggg    1740
ccggccagac gtgacagcaa tgccaaggag gccaagtttc tttgtccatt tctcacctcc    1800
ccctttttcca tccctggacc tcctggcgcc ccagtacac agaggccctt gagcagcccg    1860
gctgcaggtt ccctatctac tcagagttct ccccctcacg tgcctatccc caaccctgca    1920
```

<210> SEQ ID NO 2
<211> LENGTH: 6096
<212> TYPE: DNA
<213> ORGANISM: Homo Sapiens

<400> SEQUENCE: 2

```
taccagtgta agattcaaaa ttccctttt gcactgcaca gtgagatgcc cagggctcca      60
gctcagtgcc tggacatagc gattcctggg cctgcccgtc gccgcccaa gcgaagctgg     120
```

-continued

```
tgcgccttgg gcggagcaga cagagaccct gggtggcagg ggcttgggaa gacatgggcg      180
gctagggctt tatgcgccct caccgctgcc ctctgctatt tgcaggcaat ggacgagccg      240
ggaatgagcc tcctagacca gtccgtgatc aagaaaggta aggaatggtc tgtcagggca      300
gagcccggcg agatggtgca ggcccttggt gcacagatcc attttcttca ccggccgtgc      360
ctcctgtgtg tcgccaggct gggtgtccac caggcactct tcctggccca gccagatgtt      420
aggcagacgt gcgggcttgg tgagtttgcc cagcaccctg tggcctgggg tgggcctcag      480
cggatcagca ttcactgggc tgcagcactg ggagcctggc ctctcccgc cgaggggag       540
ggcactcttg tggatctgga gttgatttgc agaacgagtt aaaccacttc cctgtttccc      600
taagagatgg gaatggaagt gctgttccca cggagttggg gaaatgattt tcactttaca      660
gtgccttagc atttcggtgc ctggcgggca ctttcttcct cttccttcca ggcagggcct      720
tggaggcctc tgggggaatt ttcttttctgt gggagtctct tgcggcattt agacttaggg     780
gagcttgtgt gtgagtactg tgtgttaggc tgtgtgcacc tgagtcaggg cccacctgct      840
cctgggtgtc tgtgtccatg tgagttcagg gtcctgtgca tgtctgaaat gttcccttca      900
tgggtgtctt agtatttctt ggagtgtgag tgtgtctgtt tctgtgaatg tgtttgtgag      960
gtgtgtctct gtatgttggt gtgcatttct ctgcatttgg gggatgtaca catttctcaa     1020
tatgtacagt atctctgttg tgtcctgcac tttgttcttt ggtatctgag gatttccaag     1080
catgcgcggg ccctctctgt gtatatatag gagtatttat gtgactcctg gcattagtaa     1140
aatccaggga cacgggatcc acctttt ctg gcctgaggac caagtactgg ccatgacagg     1200
ggaaggtgag agacgacaaa aacagagaga cagccagaga ggagcagaga gtcagagggg     1260
cccaggcatt gggtagcagc ctctttacat ttggggcagg tgcccgaaag aattcagagg     1320
tgcacatgag cctgaggtgc cccaggcagg cactgctccc acagggtttg gcttgagttg     1380
tttttcaaac gagtgaattc aagcctgggc tctatttgcc ctccacttgt tctcaggga      1440
ggccaaggtg gaagtggtgg tagcagggct ggggctggac ttccaggagc tggggctgag     1500
ttaccaggag ctgggggttg ggtggatgac ttggagtgtg tagcagggaa gatgaggcaa     1560
cagggcagga agtgggtggg gggaggtgga attgggggctg tgtcctgtgt cgcttggaac    1620
tgggagtgtg ggaaagacac taggaacctg gttgcagcgc agctctgctg gtggggcttg     1680
gttggcttac tgtacagagc ctttcttgac ccctgaagaa agagatccgt ctgcagtggg     1740
caaaagcctg cctggacttc ctggccacca gaaatatgag catggtggtg gtccccagtt     1800
ccctattcat gcttgggctc aagagactgg gagtctaggt tcactgactc cctgagaaag     1860
actaagaccc tgcattttag aaagaggttt ggggatctct gccctgcgca agggtagaag     1920
gatcagctgt tcctctgagc accttaaccc ggaaccccgg tccgaagccg agacaggaga     1980
ctggatgcga ggccctccca gagctggttt ctctcaaaca acttccaaaa ctcctagatc     2040
ctaggggtac gccgaaatcc cccaaagcag tccaaagaac acaacgagag tcctaacatc     2100
ccaggtggcg gcgcgctggc tccctggagc ggggcggac gcggccgcgc ggactcacgt      2160
gcacaaccgc gcgggacggg gccacgcgga ctcacgtgca caaccgcggg accccagcgc     2220
cagcgggacc ccagcgccag cgggacccca gcgccagcgg gaccccagcg ccagcgggac     2280
cccagcgcca gcgggacccc agcgccagcg ggaccccagc gccagcgggt ctgtggccca     2340
gtggagcgag tggagcgctg gcgacctgag cggagactgc gccctggacg ccccagccta     2400
gacgtcaagt tacagcccgc gcagcagcag caaaggggaa ggggcaggag ccgggcacag     2460
ttggatccgg aggtcgtgac ccaggggaaa gcgtgggcgg tcgacccagg gcagctgcgg     2520
```

```
cggcgaggca ggtgggctcc ttgctccctg gagccgcccc tccccacacc tgccctcggc    2580
gcccccagca gttttcacct tggccctccg cggtcactgc gggattcggc gttgccgcca    2640
gcccagtggg gagtgaatta gcgccctcct tcgtcctcgg ccttccgac ggcacgagga     2700
actcctgtcc tgcccacag accttcggcc tccgccgagt gcggtactgg agcctgcccc    2760
gccagggccc tggaatcaga gaaagtcgct ctttggccac ctgaagcgtc ggatccctac    2820
agtgcctccc agcctgggcg ggagcggcgg ctgcgtcgct gaaggttggg gtccttggtg    2880
cgaaagggag gcagctgcag cctcagcccc accccagaag cggccttcgc atcgctgcgg    2940
tgggcgttct cggcttcga cttcgccagc gccgcgggc agaggcacct ggagctcgca      3000
gggcccagac ctgggttgga aaagcttcgc tgactgcagg caagcgtccg ggaggggcgg    3060
ccaggcgaag ccccggcgct ttaccacaca cttccgggtc ccatgccagt tgcatccgcg    3120
gtattgggca ggaaatggca gggctgaggc cgaccctagg agtataaggg agccctccat    3180
ttcctgccca catttgtcac ctccagtttt gcaacctatc ccagacacac agaaagcaag    3240
caggactggt ggggagacgg agcttaacag gaatattttc cagcagtgag cagggctgt     3300
atgggacgcg ggaggagctc agaggaggcg cggagagtgc ccgaggttgg gtgagtgcct    3360
agaggggaga tagttgaacc gggttcaaga ggtgcttagt gggtgtttgt tgaatgaatg    3420
agtgatgggc tttgaagtct gagtgcattg aaagaggggg tgtgtaaaaa gggctccttt    3480
catcacacag gacacagcat atgcaaatcc tctccctgtg gaaaagccag acaggttaaa    3540
aaggttacaa acaaattagc cgggcatggt ggtgcgcgtc tgtagtccca gctactaggg    3600
aggctgagcc aggggaatcg cttgaacccg ggaggcggag attgcagtga gccaagatcg    3660
cgccactgca ctccagcctg gaaacagagc gagactccgt ctcggaaaaa aaaaaaaaa     3720
gttacaaacc gtgtgtgggt ttcaggttat acaatcagag ctggagggga gtggtcaagg    3780
atgagaactg agatggatcc ctcgttccct ctggaggaga gtgggtggtt gcctacttgg    3840
gggtggggaa tccctctcca cgggctcagc tgtccaatct caggggatct ctaggacagg    3900
agctgatgta aacagtcgcc ctattccttg ctgtctttgg ccctggagaa ggaggaggga    3960
gctgggagg gtctccactt cccagacaat ctctaagcag ccaggacatg ggtgagatga    4020
gtgagatact gacttctggg acagaatttg agagggtgcc aaaaaactca gtaatcaaga    4080
taaataggcc gggcgcagtg gctcacgtct gtaatcccag cactttggga ggccggatca    4140
cttgaggtca gagttcgag accagcctgg ccaagatggt gaaacccat ctctactaaa      4200
aatacaaaaa ttagcccagt gtggtggcgc tagcctgtaa tcccagccac tcaggaggct    4260
gaggcaagag aattgcttga cccaggaggc agaggttgca gtgagccgag atcatgccac    4320
tgtactccag cctggacaac agaggagac tatctcaaaa aaaaaaaaa aaaaaaaa       4380
aaaaagagg ccgggcggcg gtggctcaca ccatgtgatc ccagcacttt gggaggccga    4440
ggcgggtgga tcacctgagg tctggagttc gagaccagcc tggccaatat ggtgaaaccc    4500
cgtttctact aaaaatacaa aaattagctg ggtggggtgg caggcacctg taatcccagc    4560
tactccggag gctgaggcag gagaatccct tgaacctgcg gggcggaggt tgcagtgaac    4620
caagatcaca ccattgcact ccagcctgga caacaacagc aaaactctgt ctcaaaaaaa    4680
aaaaaatct tttttttcga gacacagttt tactctctcg cccaggttgg ggtgcagcac    4740
cacgatctca gctcactgca acctctgcct ctcagattct cgtacctcag cctcccaagt    4800
agctgggatt acaggtacct gtcaccacgc ccagctaatt tttgtatttt tagtagggc     4860
```

```
gtggtttcac catgttggcc aggctggtct tgaactcctg acctcaagtg acctgcccgc    4920
ttcagccacc caaagtgctg ggattacagg cgtgagccac cacgcttggc cttttttaaat   4980 gaaaatagtg caaaaatcca cgataaacaa aatatcaaaa atttactgaa cttgcacttc    5040 cacaacccttt tctcacctgc ctcccaggct actctctgcc ccagaaagca acttaaaaaa   5100
tgtgcagatg gagtttggac tttacctgaa aatggtggga gctatggaaa accttggagc    5160
aggggagtga aggatagaaa ttatatgtaa aagaaaccct gggccgggcg cagtggctta    5220
tgcctgtaat cccagcactt tgggaggccg aggcaggtgg attacctgag gtcaggagat    5280
tgagaccagc ctgaccaaca tggtgaaatg tcatctctac taaaaataca aaaaaaatta    5340
gccaggcatg gtggtgcacg cctgtagtcc cagctactcc ggaggctgag acaggaaaat    5400
cgcttgaacc cggaggcgg aggttgcagt gagccaagat tgtgccattg cactccagcc     5460
tgggcaacaa gagcaaaact ccatcttaaa aaaaagaaa gaaagaaacc ctctggcagt    5520
tgatgagaag gaaacttaat cggcaggtcc cagcagggga gatgaggaga ctctagggag    5580
ggcatttgca catgctgtgc cccagtgtgg gccaggagc aggtcactac tcctcccgtc      5640
taccttcctc ttgctccaac cccttcaagc tttggaccag tggtaccta agtgtagtcc      5700 aaggaaccac atgcatcagg accccagggg ggtgcttgtt aaaaatgcaa attttggcca    5760
ggtgcagtgg ctcacacctg taatcccagc actttgggag gccgaggcgg gtggatcacg    5820
aggtcaggag atcgagacca tcctggcaaa cacggtgaaa ccccatctct actaaaaaaa    5880 caaaacaaa ccaaaaaaaa cattagctgg gcgtggtggc gggcgcctgt agtcccagct      5940
actcgggagg ctgaggcagg agaatggcgt gaacccggga ggcggagctt gcagtgagct    6000
gagattgcgc cactgcaccc cagcctgggc gacagagcga gactctgcct caaaaaaaa    6060 aaagcaaatt tcttgggcac cacccccacat tgactg                             6096

<210> SEQ ID NO 3
<211> LENGTH: 2501
<212> TYPE: DNA
<213> ORGANISM: Homo Sapiens

<400> SEQUENCE: 3
tttgcaaatg gagacatctt cattattcct atagtatcat atgttttta agtttgtact       60 cacactttgg gtgataaatg aaggacaaga tccttcccta tccttgtgag gatgactaca     120
gcatgactgg atgggcttgc tatgattttt atctttccct gtgttctcac taccgttttta   180 ttaatctcag ttctttttca cagggtagca cagaatttaa ctagcagaaa gagatccagc    240
catgtagacc agagatttgt ctaagtgacg gcatgtaaga atcaggaagg aaagtttttt    300
gtttaaatac caacaggttc cttccttaaa gcaattatta ttttcaaat ctaacccaca     360 aggtgatagt atccttaaac caattaaatc agaatctcgg gttggataac ctcaaatatg    420
acttattagc acttcccatt aatcactggt ccttcaggcc tttaagtttta cttactagga   480 atctcacttt taataccatc ttatcaactt cagttgtaaa taagaaaca ctcaaaggct     540 gaggaattct cagcggtaaa gctctgccca cgttaagtaa caaaggataa gttagtcttt    600
gttgtgatca ctttgttgta ctgataagct acgtatttct actcaaggat tcaaattctc    660
acctttctca agaattgggc caaaaccgat aaactaaact tatttacggt ccactgatta   720
aaggttgttg cataataagt tcttgctatg ttcagcagtt ggattcacag cgccagaaac    780
ctataactgc ttgactttcc tccccactac actgcgaaaa ttgcccctta aatgtaacta    840
accctaaaac ctcaacagta tcgtggccag gcgtggtggc tcactactgt aataccaaca    900
```

```
ttaggcatag gcgagggggat tgaggccagg atatcgaaac tagcctggga aacacacgga    960
gacccggtct ttggaaaaat aattagcctt gcgtggtggt gggcgcgagg ttccggctaa   1020
tcgggaggct acagtgagcc atgatgacac tgcactacag tctgcgcgac ggcccatgtc   1080
agtaagctct ggagcacctg aaacaagttg tgttgggtat tttatttact ggagagcgat   1140
tagtgactga tgcctactta cagcgactag agacgcatgc tccgatagca gcacaaactc   1200
agcaggcgcg aacaaatggt aaagagaaac tgggcaaaca agcatcacgg ctcctcagct   1260
gagaaagtgg gggccctaaa aagggccttt tgttgataga aagggacgct caaccaccga   1320
aaccgtagag ggtgcggccc tggcgcttga gcgcgtagac cacatccatg gcggtgaccg   1380
tcttgcgctt ggcgtgctct gtataggtca cggcgtcccg gatcacgttc tccaggaaca   1440
ccttcagcac cccgcgagtc tcctcgtaga tgaggccgga gatgcgcttc acgccgccgc   1500
ggcgagcaag gcgccggatg gccggcttgg tgatgccctg gatattgtcg cgcagtactt   1560
tacggtggcg cttagcgccg cctttgccaa gacccttccc gcctttgccg cggccagaca   1620
tgacgagcaa gaggagtctc acccaacgct tgtgaggac tctggcctga ggcagcgcct   1680
ttatacgaca gttggcggac cgaactgaga acctgaaaga agtcggcggg aagtcccgcc   1740
ccggtggggg aggggaaatc taaagggcca aaccgaaata gggggaaaaa aaaagcgagc   1800
ttcttgtttc cgtgttctga attttgtaac gtgcatagta ttttgttacc acgttatgag   1860
gctttaaaaa attgcttttg aacgcagaag atatacatca atactgtggg aaatacaaga   1920
aaggacaaga aattaagaaa ctacaatgtt atcccatcac acaggctagt taatcatgta   1980
ttttgcagag cagttgcaca tattttttcca agaaaatgta tacagtgttg tatatggagt   2040
tttgtaacct ccttatattg attataattt aaccaatttc tattaaagag ataaagtga    2100 tgttttggtg tctatgtttc ttaggaatta tcaatagtta taatcagttc cccagcaatt   2160
ttttaatcgg ctgtatttta aaaataatgt tttccacatt caacataaat gtactttttc   2220
tctatacttg ggaccaatat tgaaatttat gattttatta caccaaaatt taaatttat    2280 tacattaata tttaaaattg tattagaggt ctcatgattt ggtactacgg gtctccgcat   2340
tatttccttt ccaaatttcc taatctgttt caccaaggtt tctggacaac tttagagacc   2400
ttttgtgaag tttgaataaa atctcttcga gattttgata attgcattag ctttaggact   2460
taattggaat agaattaaaa tccttaaaac aagctcttat a                       2501
```

<210> SEQ ID NO 4
<211> LENGTH: 2501
<212> TYPE: DNA
<213> ORGANISM: Homo Sapiens

<400> SEQUENCE: 4

```
ttgttgtaca gaatatttca tcacccaggt attatgccga gtacccaata gttctctttt     60
ctgctcctct ccttcctccc atcctgcacc ctggagtcaa ccacagtgtc tgttgtttcc    120
ttgtttgtgt tataagttct catcatttag ctcccactta caagtgagaa catccagtat    180
ttggatttct gttcctgcat tagttttgcta aggataatag cctctagctc catccatgtt    240
cccacaaaag acatgatcta gttctttta atggctgcat taaatgaagt tttaaagata    300
caacataaac accaacctct tccccaccac aaaaatccct tgctgaattt gattacactt    360
aaattaacga gttttgtttc atgaaagact ccttggacaa acttgacagt tgatggaata    420
ggagaagctg tctgtcatgt ctaaagccaa caagagatca atatctagaa taaatggaga    480
```

| | |
|---|---|
| tctgcaaatc aacagaaagt aggcagcaaa gccaaagaaa atagcctaag gcacagccac | 540 |
| taaaaggaac gtgatcatgt cctttgcagg gacatgggtg gagctggaag ccgttagcct | 600 |
| cagcaaactc acacaggaac agaaaaccag cgagaccgca tggtctcact tataagtggg | 660 |
| agctgaacaa tgagaacaca tggtcacatg gcggcgatca acacacactg gtgcctgttg | 720 |
| agcggggtgc tggggaggga gagtaccagg aagaatagct aagggatact gggcttaata | 780 |
| cctgggtgat gggatgatct gtacagcaaa ccatcatggc gcacacacct atgtaacaaa | 840 |
| cctgcacatc ctctacatgt accccagaac ttcaaataaa agttggacgg ccaggcgtgg | 900 |
| tggctcacgc ctgtaatccc agcactttgg gaagccgagg cgtgcagatc acctaaggtc | 960 |
| aggagttcga gaccagcccg gccaacatgg tgaaacccccg tctctactaa aaatacaaaa | 1020 |
| atcagccaga tgtggcacgc acctataatt ccacctactc gggaggctga agcagaattg | 1080 |
| cttgaacccg agaggcggag gttgcagtga gccgccgaga tcgcgccact gcactccagc | 1140 |
| ctgggccaca gcgtgagact acgtcataaa ataaaataaa ataacacaaa ataaaataaa | 1200 |
| ataaaataaa ataaaataaa ataaaataaa ataaaataaa ataaaaaaat aaaataaaat | 1260 |
| aaaataaaat aaagcaattt cctttcctct aagcggcctc caccccctctc ccctgccctg | 1320 |
| tgaagcgggt gtgcaagctc cgggatcgca gcggtcttag ggaatttccc cccgcgatgt | 1380 |
| cccggcgcgc cagttcgctg cgcacacttc gctgcggtcc tcttcctgct gtctgtttac | 1440 |
| tccctaggcc ccgctgggga cctgggaaag agggaaaggc ttccccggcc agctgcgcgg | 1500 |
| cgactccggg gactccaggg cgcccctctg cggccgacgc ccggggtgca gcggccgccg | 1560 |
| gggctggggc cggcgggagt ccgcgggacc ctccagaaga gcggccggcg ccgtgactca | 1620 |
| gcactggggc ggagcggggc gggaccaccc ttataaggct cggaggccgc gaggccttcg | 1680 |
| ctggagtttc gccgccgcag tcttcgccac cagtgagtac gcgcggcccg cgtcccccggg | 1740 |
| gatgggggctc agagctccca gcatggggcc aacccgcagc atcaggcccg ggctcccggc | 1800 |
| agggctcctc gcccacctcg agacccggga cggggggccta ggggacccag gacgtccccca | 1860 |
| gtgccgttag cggctttcag ggggcccgga gcgcctcggg gagggatggg accccggggg | 1920 |
| cggggagggg gggcagactg cgctcaccgc gccttggcat cctcccccgg gctccagcaa | 1980 |
| acttttcttt gttcgctgca gtgccgccct acaccgtggt ctatttccca gttcgaggta | 2040 |
| ggagcatgtg tctggcaggg aagggaggca ggggctgggg ctgcagccca cagcccctcg | 2100 |
| cccacccgga gagatccgaa ccccccttatc cctccgtcgt gtggcttttta ccccgggcct | 2160 |
| ccttcctgtt ccccgcctct cccgccatgc ctgctcccg cccagtgtt gtgtgaaatc | 2220 |
| ttcggaggaa cctgtttccc tgttccctcc ctgcactcct gaccccctccc cgggttgctg | 2280 |
| cgaggcggag tcgccccggt ccccacatct cgtacttctc cctccccgca ggccgctgcg | 2340 |
| cggccctgcg catgctgctg gcagatcagg gccagagctg gaaggaggag gtggtgaccg | 2400 |
| tggagacgtg gcaggagggc tcactcaaag cctcctgcgt aagtgaccat gcccgggcaa | 2460 |
| ggggagggggg tgctgggcct tagggggctg tgactaggat c | 2501 |

<210> SEQ ID NO 5
<211> LENGTH: 1920
<212> TYPE: DNA
<213> ORGANISM: Artificial Sequence
<220> FEATURE:
<223> OTHER INFORMATION: chemically treated genomic DNA (Homo sapiens)

<400> SEQUENCE: 5

| | |
|---|---|
| ttaggttgtc gtagatatag ttttttgtttt ttcgaaaaat acgttttagg cgtcgggatt | 60 |

```
ttagatattt gggaaataga gtgtacgtag ttgttgagag gtttcgcgtt tggttttttt      120
tattattgag gcgtagaggt gttgtggata gtttagattt atacggcgtt cgaggtgaaa      180 tagaatttt agtttttta tgaggttatt ggtattttcg gttgttttta gagttttcg        240 atttagagtt gaatgtaaag taagcgttcg aaatgtagaa gtagtcgggg tcgtttacgg      300
tatttgtttc gttcggggcg agagaagacg ttaggttgag gttttagcga ttttaggtat     360
tagtttcgaa ggagggcggg gagatcgtaa agggggaagtg ttcggagggt taacggtttt    420
cgcgtatttt gcgttttttt gaagcgcgtc gttttttcgc gtcgggatt gggatttgtt      480 tttggggaat tcgtttagaa gacggcggcg gattgggtc gggtatttt tagggttgtt       540 aggtttttt tagtttgta tttgtcgcgt cgttttattt cgttaggaag tttagagat        600 ttcggggatg gggtgggagc gttttttat cgcgggttta aaagaagga aggacgtttt       660 taggggtcgt agaaggagga ttagttttaa gttataattt ttttcggatt taaggtaggt     720
cggttggggt ttcgcgttta tacggttttt ggcgggggtt cgcgcgtttc gggagttcg      780 cggttcgggg aggaaagagg agataagaga taggcgagga ttacgggtt gatttagtcg      840 gggtagggat tatcgtggaa aaattttggc gaggtgggg gacgcggaaa gagagcggtt      900
cgcgttttgt atttgcgtc gggtatttcg cgttagtgtt tcgttttag tgtttcgcgt       960 ttcgcgtttc gcgttttgtt ttatttcgg gttagttgta tcgcgttcgc gtcgtaggaa      1020
tcgtggagtt ggaaagtggg ggcgtcgcgg ttgggggtt gttttagttg cgtttcggtt     1080
agcgatcggc gggtcgggtt taaatttagt taggttgggt aggcggtggt cgcgcgattg     1140 gggatcggc gttcgtttt tttcgttttt ttttttttt ttttttttt ttttagtttt        1200 ttggttttt ttagttttta tcggatttgt tcgttcgttg tttttttt ttttcgttt         1260 tttatattat ttttattttt ttcgttttgt tttcgtttt tttttttt ttgttttttg        1320 ttttttttt ttttttttt tttttaggg gcggagtttt ttttttttt tttagataat         1380 gttgtggttg cgttttttt ttcgttagtt cgttaggtt ttcgtcgtta gcgatttttt       1440
cgggttgggg gtggggaggt ggggggggag tgtaggggtg gggaggatga gttggttttt    1500 tttattttt tgttgttgtt tttttaaga gggatggaga tttggtttaa gttttcggt        1560 ttattcggag ttgtgatagt tattttagg gaatagttac gttgttttat taagtttatt     1620
tttagcggtt tggattttt aggtagaggt tgtgggattt tgtttttt aatatttag         1680 tttattttta aagggttg agtcggatag gggttaaata ggtttttcg atttggcggg       1740 tcggttagac gtgatagtaa tgttaaggag gttaagtttt tttgtttatt ttttatttt     1800 ttttttta tttttggatt ttttggcgtt tttagtatat agaggttttt gagtagttcg       1860
gttgtaggtt ttttatttat ttagagtttt ttttttacg tgtttatttt taattttgta     1920
```

<210> SEQ ID NO 6
<211> LENGTH: 1920
<212> TYPE: DNA
<213> ORGANISM: Artificial Sequence
<220> FEATURE:
<223> OTHER INFORMATION: chemically treated genomic DNA (Homo sapiens)

<400> SEQUENCE: 6

```
tgtagggttg gggataggta cgtgagggggg agaattttga gtagatagg aatttgtagt     60 cgggttgttt aagggtttt gtgtattggg ggcgttagga ggtttaggga tggaaaaggg     120
ggaggtgaga aatggataaa gaaatttggt ttttttggta ttgttgttac gtttggtcgg    180
```

-continued

```
ttcgttaagt cgaaggggtt tgtttagttt ttgttcggtt taaatttttt tgggaataag      240
ttgggatgtt agaaaaaata aaattttata attttgttt ggggaattta ggtcgttgga      300
ggtgggtttg gtagggtagc gtgattgttt tttgggagtg gttgttatag tttcgggtga     360
atcgaggagt ttgggttaag ttttattttt ttttggagag ggtagtagta aggaggtgag    420
gggagttagt ttattttttt taattttgta ttttttttt attttttat ttttagttcg      480 gaagaatcgt tggcggcggg agtttggacg agttggcggg gaaggggacg tagttatagt    540
attgtttggg agggagggga gaagtttcgt ttttagaggg gaggggagaa gaggagggg     600 taggagataa ggggaggaag aaaggcgaag gtaaggcgaa ggggtggaga gtgatatgaa   660
gagcgagaga aaagagagga tagcggacga gtagattcgg taggggttga aaaaggttaa   720
ggggttggag ggagggagag gaaggaggag gggagcgagg agggcggggc gttcggtttt   780
tagtcgcgcg gttatcgttt gtttagtttg gttggatttg agttcggttc gtcgatcgtt   840
ggtcgaggcg tagttgaagt agtttttag tcgcggcgtt tttattttt aattttacgg    900 tttttgcggc gcgggcgcga tgtagttggt tcggggtgaa ggtaaggcgc ggggcgcggg   960
gcgcggggta ttgggagcga ggtattggcg cgggatgttc ggcgtaaggt gtagggcgcg  1020
ggtcgttttt ttttcgcgtt tttttatttc gttaaagtttt tttacgatg gttttttattt  1080 cggttgggtt agtttcgtaa ttttcgtttg tttttgttt ttttttttt tttcgagtcg    1140 cggggttttc ggggcgcgcg gattttcgtt agggtcgtg taggcgcgga gttttagtcg    1200
gtttgttttg ggttcgaaga aagttgtggt ttggagttag tttttttttt acgattttg    1260 ggggcgtttt ttttttttt tgagttcgcg atgggaaggc gttttatttt tatttcgggg  1320 gttttgaga ttttttggcg aggtggggcg gcgcggtagg tgtagggttg gggagggttt    1380
gatagttttg gagagtgttc gatttagttt cgtcgtcgtt ttttaggcgg atttttaga    1440 ggtaggtttt agttttcggc gcggggaggc ggcgcgtttt agagggcgt agggtgcgcg    1500 ggggtcgttg gttttcggg tatttttttt ttgcggtttt ttcgtttttt ttcggagttg    1560
gtgtttgagg tcgttgggat tttagtttgg cgtttttttt cgtttcgagc gaggtaggtg  1620
tcgtgggcgg tttcggttat ttttgtattt cgagcgttta ttttgtattt agttttaagt  1680
cggagagttt tggggatagt cgagagtgtt agtggttta tagggagatt gagggttttg    1740
ttttatttcg ggcgtcgtgt gggttttggg tgtttatagt attttttgcgt tttagtgata  1800 ggagaagtta agcgcgaggt tttttaatag ttgcgtgtat tttattttt aggtatttgg    1860 aatttcggcg tttagaacgt gttttcggg agagtaaagg ttgtgtttac ggtagtttgg   1920
```

<210> SEQ ID NO 7
<211> LENGTH: 6096
<212> TYPE: DNA
<213> ORGANISM: Artificial Sequence
<220> FEATURE:
<223> OTHER INFORMATION: chemically treated genomic DNA (Homo sapiens)

<400> SEQUENCE: 7

```
tattagtgta agatttaaaa tttttttttt gtattgtata gtgagatgtt tagggtttta       60
gtttagtgtt tggatatagc gattttggg tttgttcgtc gtcgttttaa gcgaagttgg      120
tgcgttttgg gcggagtaga tagagatttt gggtggtagg ggtttgggaa gatatgggcg    180
gttagggttt tatgcgtttt tatcgttgtt ttttgttatt tgtaggtaat ggacgagtcg    240
ggaatgagtt tttagatta gttcgtgatt aagaaaggta aggaatggtt tgttagggta    300
gagttcggcg agatggtgta ggttttggt gtatagattt atttttttta tcggtcgtgt    360
```

```
tttttgtgtg tcgttaggtt gggtgtttat taggtatttt ttttggttta gttagatgtt      420
aggtagacgt gcgggtttgg tgagtttgtt tagtattttg tggtttgggg tgggttttag      480
cggattagta tttattgggt tgtagtattg ggagtttggt ttttttttcgt cgaggggggag    540 ggtatttttg tggatttgga gttgattgt agaacgagtt aaattatttt tttgttttt       600 taagagatgg gaatggaagt gttgttttta cggagttggg gaaatgattt ttattttata     660 gtgtttagt atttcggtgt ttggcgggta tttttttttt tttttttta ggtagggttt       720 tggaggtttt tggggggaatt ttttttttgt gggagttttt tgcggtattt agatttaggg    780
gagtttgtgt gtgagtattg tgtgttaggt tgtgtgtatt tgagttaggg tttatttgtt     840
tttgggtgtt tgtgtttatg tgagtttagg gttttgtgta tgtttgaaat gtttttttta     900
tgggtgtttt agtattttt ggagtgtgag tgtgtttgtt tttgtgaatg tgtttgtgag      960
gtgtgttttt gtatgttggt gtgtattttt ttgtatttgg gggatgtata tatttttaa     1020 tatgtatagt attttgttg tgttttgtat tttgttttt ggtatttgag gatttttaag      1080
tatgcgcggg ttttttttgt gtatatatag gagtatttat gtgattttg gtattagtaa     1140 aatttaggga tacgggattt attttttttg gtttgaggat taagtattgg ttatgatagg    1200
ggaaggtgag agacgataaa aatagagaga tagttagaga ggagtagaga gttagagggg    1260
tttaggtatt gggtagtagt ttttttatat ttggggtagg tgttcgaaag aatttagagg    1320
tgtatatgag tttgaggtgt tttaggtagg tattgttttt atagggtttg gtttgagttg    1380 tttttaaac gagtgaattt aagtttgggt tttatttgtt ttttattgt ttttagggga     1440 ggttaaggtg gaagtggtgg tagtagggtt ggggttggat ttttaggagt tggggttgag    1500
ttattaggag ttggggggttg ggtggatgat tggagtgtg tagtagggaa gatgaggtaa    1560
tagggtagga agtgggtggg gggaggtgga attggggttg tgttttgtgt cgtttggaat    1620
tgggagtgtg ggaaagatat taggaatttg gttgtagcgt agttttgttg gtggggtttg    1680
gttggtttat tgtatagagt tttttttgat ttttgaagaa agagattcgt ttgtagtggg    1740
taaaagtttg tttggatttt ttggttatta gaaatatgag tatggtggtg gtttttagtt   1800
ttttatttat gtttgggttt aagagattgg gagtttaggt ttattgattt tttgagaaag    1860
attaagattt tgtattttag aaagaggttt ggggattttt gttttgcgta agggtagaag    1920
gattagttgt ttttttgagt attttaattc ggaatttcgg ttcgaagtcg agataggaga    1980
ttggatgcga ggttttttta gagttggttt tttttaaata atttttaaaa ttttttagatt  2040 ttaggggtac gtcgaaattt tttaaagtag tttaaagaat ataacgagag ttttaatatt    2100
ttaggtggcg gcgcgttggt tttttggagc ggggcgggac gcggtcgcgc ggatttacgt    2160
gtataatcgc gcgggacggg gttacgcgga tttacgtgta taatcgcggg attttagcgt    2220
tagcgggatt ttagcgttag cgggatttta gcgttagcgg gattttagcg ttagcgggat    2280
tttagcgtta gcgggatttt agcgttagcg ggatttagc gttagcgggt ttgtggttta     2340
gtggagcgag tggagcgttg gcgatttgag cggagattgc gttttggacg ttttagttta    2400
gacgttaagt tatagttcgc gtagtagtag taaaggggaa ggggtaggag tcgggtatag    2460
ttggattcga aggtcgtgat ttaggggaaa gcgtgggcgg tcgatttagg gtagttgcgg    2520
cggcgaggta ggtgggtttt tgttttttg gagtcgtttt ttttatatt tgttttcggc      2580 gttttttagta gttttatttt tggttttttcg cggttattgc gggattcggc gttgtcgtta  2640
gtttagtggg gagtgaatta gcgtttttttt tcgttttcgg tttttttcgac ggtacgagga  2700
```

```
atttttgttt tgttttatag attttcggtt ttcgtcgagt gcggtattgg agtttgtttc    2760
gttagggtta tggaattaga gaaagtcgtt ttttggttat ttgaagcgtc ggattttat     2820
agtgttttt  agtttgggcg ggagcggcgg ttgcgtcgtt gaaggttggg gttttggtg     2880
cgaaagggag gtagttgtag ttttagtttt attttagaag cggttttcgt atcgttgcgg    2940
tgggcgtttt cgggtttcga tttcgttagc gtcgcggggt agaggtattt ggagttcgta    3000
gggtttagat ttgggttgga aaagtttcgt tgattgtagg taagcgttcg ggaggggcgg    3060
ttaggcgaag tttcggcgtt ttattatata ttttcgggtt ttatgttagt tgtattcgcg    3120
gtattgggta ggaaatggta gggttgaggt cgatttttagg agtataaggg agtttttat    3180
tttttgttta tatttgttat ttttagtttt gtaatttatt ttagatatat agaaagtaag    3240
taggattggt ggggagacgg agtttaatag gaatatttt  tagtagtgag taggggttgt    3300
atgggacgcg ggaggagttt agaggaggcg cggagagtgt tcgaggttgg gtgagtgttt    3360
agaggggaga tagttgaatc gggtttaaga ggtgttagt  gggtgttgt  tgaatgaatg    3420
agtgatgggt tttgaagttt gagtgtattg aaagaggggg tgtgtaaaaa gggttttttt    3480
tattatatag gatatagtat atgtaaattt ttttttgtg  gaaaagttag ataggttaaa    3540
aaggttataa ataaattagt cgggtatggt ggtgcgcgtt tgtagtttta gttattaggg    3600
aggttgagtt aggggaatcg tttgaattcg ggaggcggag attgtagtga gttaagatcg    3660
cgttattgta ttttagtttg gaaatagagc gagatttcgt ttcggaaaaa aaaaaaaaa    3720
gttataaatc gtgtgtgggt tttaggttat ataattagag ttggagggga gtggttaagg    3780
atgagaattg agatggattt ttcgtttttt ttggaggaga gtgggtggtt gtttatttgg    3840
gggtggggaa ttttttta cgggtttagt tgtttaattt tagggggattt ttaggatagg    3900
agttgatgta aatagtcgtt ttatttttg  ttgttttgg ttttggagaa ggaggaggga    3960
gttggggagg gtttttattt tttagataat tttaagtag  ttaggatatg ggtgagatga    4020
gtgagatatt gattttggg  atagaatttg agagggtgtg aaaaaattta gtaattaaga    4080
taaataggtc gggcgtagtg gtttacgttt gtaattttag tattttggga ggtcggatta    4140
tttgaggtta agagttcgag attagtttgg ttaagatggt gaaattttat ttttattaaa    4200
aatataaaaa ttagtttagt gtggtggcgt tagtttgtaa ttttagttat ttaggaggtt    4260
gaggtaagag aattgtttga tttaggaggt agaggttgta gtgagtcgag attatgttat    4320
tgtattttag tttggataat agagggagat tattttaaaa aaaaaaaaaa aaaaaaaaa    4380
aaaaaagagg tcggcggcg  gtggtttata ttatgtgatt ttagtatttt gggaggtcga    4440
ggcgggtgga ttatttgagg tttggagttc gagattagtt tggttaatat ggtgaaattt    4500
cgtttttatt aaaatataaa aaattagttg ggtggggtgg taggtatttg taattttagt    4560
tatttcggag gttgaggtag gagaattttt tgaatttgcg gggcggaggt tgtagtgaat    4620
taagattata ttattgtatt ttagtttgga taataatagt aaaatttgt  tttaaaaaaa    4680
aaaaaatt   ttttttcga gatatagttt tattttttcg tttaggttgg ggtgtagtat    4740
tacgatttta gttattgta  attttgtt   tttagatttt cgtattttag ttttttaagt    4800
agttgggatt ataggtattt gttattacgt ttagttaatt tttgtatttt tagtaggggc    4860
gtggttttat tatgttggtt aggttggttt tgaattttg  attttaagtg atttgttcgt    4920
tttagttatt taaagtgttg ggattatagg cgtgagttat tacgtttggt ttttttaaat    4980
gaaaatagtg taaaaattta cgataaataa aatattaaaa atttattgaa tttgtatttt    5040
tataattttt ttttatttgt tttttaggtt atttttgtt  ttagaaagta atttaaaaaa    5100
```

```
tgtgtagatg gagtttggat tttatttgaa aatggtggga gttatggaaa attttggagt    5160
aggggagtga aggatagaaa ttatatgtaa aagaaatttt gggtcgggcg tagtggttta    5220
tgtttgtaat tttagtattt tgggaggtcg aggtaggtgg attatttgag gttaggagat    5280
tgagattagt ttgattaata tggtgaaatg ttatttttat taaaaatata aaaaaaatta    5340
gttaggtatg gtggtgtacg tttgtagttt tagttatttc ggaggttgag ataggaaaat    5400
cgtttgaatt cggaggcgg  aggttgtagt gagttaagat tgtgttattg tattttagtt    5460
tgggtaataa gagtaaaatt ttattttaaa aaaaagaaa  gaaagaaatt ttttggtagt    5520
tgatgagaag gaaatttaat cggtaggttt tagtagggga gatgaggaga ttttagggag    5580
ggtatttgta tatgttgtgt tttagtgtgg gttagggagt aggttattat ttttttcgtt    5640
tatttttttt ttgtttaat  tttttaagt  tttggattag tggtatttta agtgtagttt    5700
aaggaattat atgtattagg attttaggg  ggtgtttgtt aaaaatgtaa attttggtta    5760
ggtgtagtgg tttatatttg taattttagt attttgggag gtcgaggcgg gtggattacg    5820
aggttaggag atcgagatta ttttggtaaa tacggtgaaa ttttattttt attaaaaaaa    5880
taaaaataaa ttaaaaaaaa tattagttgg gcgtggtggc gggcgtttgt agttttagtt    5940
attcgggagg ttgaggtagg agaatggcgt gaattcggga ggcggagttt gtagtgagtt    6000
gagattgcgt tattgtattt tagttttggc gatagagcga gattttgttt taaaaaaaaa    6060
aaagtaaatt ttttgggtat tattttatat tgattg                             6096

<210> SEQ ID NO 8
<211> LENGTH: 6096
<212> TYPE: DNA
<213> ORGANISM: Artificial Sequence
<220> FEATURE:
<223> OTHER INFORMATION: chemically treated genomic DNA (Homo sapiens)

<400> SEQUENCE: 8
tagttaatgt ggggtggtgt ttaagaaatt tgttttttttt ttttgaggt  agagtttcgt      60 tttgtcgttt aggttggggt gtagtggcgt aattttagtt tattgtaagt ttcgtttttc     120
gggtttacgt tatttttttg ttttagtttt tcgagtagtg gggattatag gcgttcgtta     180
ttacgtttag ttaatgtttt ttttggtttg ttttgtttt  tttagtagag atggggtttt     240
atcgtgtttg ttaggatggt ttcgatttttt tgatttcgtg atttattcgt ttcggttttt     300
taaagtgttg ggattatagg tgtgagttat tgtatttggt taaaatttgt attttttaata    360 agtattttttt gggggttttg atgtatgtgg tttttttggat tatatttagg gtattattgg    420
tttaaagttt gaaggggttg gagtaagagg aaggtagacg ggaggagtag tgatttgttt     480
tttggtttat attggggtat agtatgtgta aatgtttttt ttagagtttt tttatttttt    540
ttgttgggat ttgtcgatta agttttttt  ttattaattg ttagagggtt tttttttttt    600
ttttttttta agatggagtt ttgttttttgt tgttttaggtt ggagtgtaat ggtataattt     660
tggtttattg taattttcgt ttttcgggtt taagcgattt ttttgtttta gttttcggag    720
tagttgggat tataggcgtg tattattatg tttggttaat ttttttttgta ttttttagtag    780 agatgatatt ttattatgtt ggttaggttg gttttaatt  tttgatttta ggtaatttat     840
ttgtttcggt ttttttaaagt gttgggatta taggtataag ttattgcgtt cggtttaggg    900 tttttttttat atataatttt tattttttat ttttttgttt taaggttttt tatagttttt     960 attatttttta ggtaaagttt aaatttttatt tgtatatttt ttaagttgtt ttttgggta   1020
```

```
gagagtagtt tgggaggtag gtgagaaagg gttgtggaag tgtaagttta gtaaatttttt    1080
gatattttgt ttatcgtgga tttttgtatt attttttattt aaaaaggtta agcgtggtgg    1140
tttacgtttg taattttagt attttgggtg gttgaagcgg gtaggttatt tgaggttagg    1200
agtttaagat tagtttggtt aatatggtga aattacgttt ttattaaaaa tataaaaatt    1260
agttgggcgt ggtgataggt atttgtaatt ttagttattt gggaggttga ggtacgagaa    1320
tttgagaggt agaggttgta gtgagttgag atcgtggtgt tgtattttaa tttgggcgag    1380
agagtaaaat tgtgtttcga aaaaaaagat tttttttttt tttgagatag agttttgttg    1440
ttgttgttta ggttggagtg taatggtgtg attttggttt attgtaattt tcgtttcgta    1500
ggtttaaggg atttttttgt tttagttttc ggagtagttg ggattatagg tgtttgttat    1560
tttatttagt taattttgt attttagta gaaacgggt tttattatat tggttaggtt    1620
ggtttcgaat tttagatttt aggtgattta ttcgtttcgg ttttttaaag tgttgggatt    1680
atatggtgtg agttatcgtc gttcggtttt tttttttttt tttttttttt tttttttttt    1740
gagatagttt ttttttgttg tttaggttgg agtatagtgg tatgatttcg gtttattgta    1800
attttttgttt tttgggttaa gtaattttt tgttttagtt ttttgagtgg ttgggattat    1860
aggttagcgt tattatattg ggttaatttt tgtattttta gtagagatgg ggttttatta    1920
ttttggttag gttggtttcg aattttttgat tttaagtgat tcggtttttt aaagtgttgg    1980
gattatagac gtgagttatt gcgttcggtt tatttatttt gattattgag tttttggta    2040
ttttttaaa ttttgttta gaagttagta tttttatt tttatttatg ttttggttgt    2100
ttagagattg tttgggaagt ggagattttt tttagttttt tttttttttt ttagggttaa    2160
agatagtaag gaatagggcg attgtttata ttagtttttg ttttagagat ttttttgagat    2220
tggatagttg agttcgtgga gagggatttt ttatttttaa gtaggtaatt atttattttt    2280
ttttagaggg aacgagggat ttattttagt tttttttt gattattttt tttagttttt    2340
gattgtataa tttgaaattt atatacggtt tgtaatttt tttttttttt ttcgagacgg    2400
agtttcgttt tgtttttagg ttggagtgta gtggcgcgat tttggttat tgtaattttc    2460
gtttttcggg tttaagcgat ttttttggtt tagtttttt agtagttggg attatagacg    2520
cgtattatta tgttcggtta atttgtttgt aatttttta atttgtttgg ttttttata    2580
gggagaggat ttgtatatgt tgtgttttgt gtgatgaaag gagtttttt tatatatttt    2640
tttttttaat gtatttagat tttaaagttt attatttatt tatttaataa atatttatta    2700
agtattttt gaattcggtt taattatttt tttttaggt atttattaa tttcgggtat    2760
ttttcgcgtt tttttgagt tttttcgcg tttatatag tttttgttta ttgttggaaa    2820
atattttttgt taagttcgt tttttatta gttttgtttg ttttttgtgt gtttgggata    2880
ggttgtaaaa ttggaggtga taaatgtggg taggaaatgg agggttttt tatattttta    2940
gggtcggttt tagttttgtt atttttttgtt taatatcgcg gatgtaattg gtatgggatt    3000
cggaagtgtg tggtaaagcg tcggggtttc gtttggtcgt tttttcgga cgttgttttg    3060
tagttagcga agttttttta atttaggttt gggttttgcg agtttaggt gttttgttt    3120
cgcggcgttg gcgaagtcga agttcgagaa cgtttatcgt agcgatgcga aggtcgtttt    3180
tggggtgggg ttgaggttgt agttgttttt ttttcgtatt aaggatttta attttagcg    3240
acgtagtcgt cgttttcgtt taggttggga ggtattgtag ggattcgacg ttttaggtgg    3300
ttaaagagcg atttttttg atttaggggt tttgcggggg taggttttag tatcgtattc    3360
ggcggaggtc gaaggtttgt ggggtaggat aggagttttt cgtgtcgtcg gaagggtcga    3420
```

-continued

```
ggacgaagga gggcgttaat ttatttttta ttgggttggc ggtaacgtcg aatttcgtag    3480
tgatcgcgga gggttaaggt gaaaattgtt ggggggcgtcg agggtaggtg tggggagggg    3540
cggttttagg gagtaaggag tttatttgtt tcgtcgtcgt agttgttttg ggtcgatcgt    3600
ttacgttttt ttttgggtta cgattttcgg atttaattgt gttcggtttt tgtttttttt    3660
tttttgttgt tgttgcgcgg gttgtaattt gacgtttagg ttggggcgtt tagggcgtag    3720
ttttcgttta ggtcgttagc gttttattcg ttttattggg ttatagattc gttggcgttg    3780
gggtttcgtt ggcgttgggg tttcgttggc gttgggtttt cgttggcgtt ggggtttcgt    3840
tggcgttggg gtttcgttgg cgttgggggtt tcgttggcgt tggggtttcg cggttgtgta    3900
cgtgagttcg cgtggtttcg tttcgcgcgg ttgtgtacgt gagttcgcgc ggtcgcgttt    3960
cgtttcgttt tagggagtta gcgcgtcgtt atttgggatg ttaggatttt cgttgtgttt    4020
tttggattgt tttgggggat tcggcgtat ttttaggatt taggagtttt ggaagttgtt     4080
tgagagaaat tagttttggg agggtttcgt atttagttttt ttgtttcggt ttcggatcgg    4140
ggtttcgggt taaggtgttt agaggaatag ttgattttt tatttttgcg tagggtagag     4200
atttttaaat tttttttaa aatgtagggt tttagttttt tttagggagt tagtgaattt     4260
agattttag tttttttgagt ttaagtatga atagggaatt ggggattatt attatgttta    4320
tattttggt ggttaggaag tttaggtagg ttttgttta ttgtagacgg attttttttt     4380
ttaggggta agaaaggttt tgtatagtaa gttaattaag ttttattagt agagttgcgt    4440
tgtaattagg ttttagtgt tttttttata tttttagttt taagcgatat aggatatagt     4500
tttaatttta tttttttta tttattttt gttttgttgt tttatttttt ttgttatata     4560
ttttaagtta tttattaat ttttagtttt tggtaattta gttttagttt ttggaagttt     4620
agttttagtt ttgttattat tattttatt ttggttttttt ttgagaataa gtggagggta    4680
aatagagttt aggtttgaat ttattcgttt gaaaaataat ttaagttaaa ttttgtggga    4740
gtagtgtttg tttggggtat tttaggttta tgtgtatttt tgaatttttt cgggtatttg    4800
ttttaaatgt aaagaggttg ttatttaatg tttgggtttt tttgattttt tgttttttt    4860
tggttgtttt tttgttttg tcgttttta tttttttttg ttatggttag tatttggttt     4920
ttaggttaga aaaggtggat ttcgtgtttt tggattttat taatgttagg agttatataa    4980
atattttat atatatatag agagggttcg cgtatgtttg gaaattttta gatattaaag    5040
aataaagtgt aggatataat agagatattg tatatattga gaaatgtgta tattttttaa    5100
atgtagagaa atgtatatta atatatagag atatattta taaatatatt tatagaaata    5160
gatatattta tattttaaga aatattaaga tatttatgaa gggaatattt tagatatgta    5220
taggattttg aatttatatg gatatagata tttaggagta ggtgggtttt gatttaggtg    5280
tatatagttt aatatatagt atttatatat aagttttttt aagtttaaat gtcgtaagag    5340
attttttatag aaagaaaatt tttttagagg ttttttaaggt tttgtttgga aggaagagga    5400
agaaagtgtt cgttaggtat cgaaatgtta aggtattgta aagtgaaaat tattttttta    5460
atttcgtggg aatagtattt ttatttttat tttttaggga aatagggaag tggtttaatt    5520
cgttttgtaa attaatttta gatttataag agtgttttttt ttttcggcgg ggagaggtta    5580
ggttttttagt gttgtagttt agtgaatgtt gattcgttga ggtttatttt aggttatagg    5640
gtgttgggta aatttattaa gttcgtacgt ttgtttaata tttggtgggg ttaggaagag    5700
tgtttggtgg atatttagtt tggcgatata taggaggtac ggtcggtgaa gaaaatggat    5760
```

-continued

| | |
|---|---|
| ttgtgtatta agggtttgta ttatttcgtc gggttttgtt ttgatagatt attttttatt | 5820 |
| tttttttgatt acggattggt ttaggaggtt tattttcggt tcgtttattg tttgtaaata | 5880 |
| gtagagggta gcggtgaggg cgtataaagt tttagtcgtt tatgttttt taagttttg | 5940 |
| ttatttaggg ttttgtttg tttcgtttaa ggcgtattag tttcgtttgg ggcggcgacg | 6000 |
| ggtaggttta ggaatcgtta tgtttaggta ttgagttgga gttttgggta ttttattgtg | 6060 |
| tagtgtaaaa agggaatttt gaattttata ttggta | 6096 |

<210> SEQ ID NO 9
<211> LENGTH: 2501
<212> TYPE: DNA
<213> ORGANISM: Artificial Sequence
<220> FEATURE:
<223> OTHER INFORMATION: chemically treated genomic DNA (Homo sapiens)

<400> SEQUENCE: 9

| | |
|---|---|
| tttgtaaatg gagatatttt tattatttt atagtattat atgttttaa agtttgtatt | 60 |
| tatattttgg gtgataaatg aaggataaga ttttttttta tttttgtgag gatgattata | 120 |
| gtatgattgg atgggtttgt tatgattttt attttttttt gtgtttttat tatcgttta | 180 |
| ttaattttag ttttttttta tagggtagta tagaatttaa ttagtagaaa gagatttagt | 240 |
| tatgtagatt agagatttgt ttaagtgacg gtatgtaaga attaggaagg aaagttttt | 300 |
| gtttaaatat taataggttt ttttttttaaa gtaattatta tttttttaaat ttaatttata | 360 |
| aggtgatagt attttttaaat taattaaatt agaatttcgg gttggataat tttaaatatg | 420 |
| atttattagt atttttttatt aattattggt tttttaggtt tttaagttta tttattagga | 480 |
| atttttatttt taatattatt ttattaattt tagttgtaaa taagagaata tttaaaggtt | 540 |
| gaggaatttt tagcggtaaa gttttgttta cgttaagtaa taaaggataa gttagttttt | 600 |
| gttgtgatta ttttgttgta ttgataagtt acgtattttt atttaaggat ttaaattttt | 660 |
| attttttta agaattgggt taaaatcgat aaattaaatt tatttacggt ttattgatta | 720 |
| aaggttgttg tataataagt ttttgttatg tttagtagtt ggatttatag cgttagaaat | 780 |
| ttataattgt ttgattttt tttttattat attgcgaaaa ttgtttttta aatgtaatta | 840 |
| attttaaaat tttaatagta tcgtggttag gcgtggtggt ttattattgt aatattaata | 900 |
| ttaggtatag gcgaggggat tgaggttagg atatcgaaat tagtttggga aatatacgga | 960 |
| gattcggttt ttggaaaaat aattagtttt gcgtggtggt gggcgcgagg tttcggttaa | 1020 |
| tcgggaggtt atagtgagtt atgatgatat tgtattatag tttgcgcgac ggtttatgtt | 1080 |
| agtaagtttt ggagtatttg aaataagttg tgttgggtat tttattttatt ggagagcgat | 1140 |
| tagtgattga tgtttatta tagcgattag agacgtatgt ttcgatagta gtataaattt | 1200 |
| agtaggcgcg aataaatggt aaagagaaat tgggtaaata agtattacgg ttttttagtt | 1260 |
| gagaaagtgg gggttttaaa aagggttttt tgttgataga aagggacgtt taattatcga | 1320 |
| aatcgtagag ggtgcggttt tggcgtttga gcgcgtagat tatatttatg gcggtgatcg | 1380 |
| ttttgcgttt ggcgtgtttt gtataggtta cggcgtttcg gattacgttt tttaggaata | 1440 |
| tttttagtat ttcgcgagtt ttttcgtaga tgaggtcgga gatgcgtttt acgtcgtcgc | 1500 |
| ggcgagtaag gcgtcggatg gtcggtttgg tgatgttttg gatattgtcg cgtagtatt | 1560 |
| tacggtggcg tttagcgtcg ttttttgttaa gatttttttc gttttttgtcg cggttagata | 1620 |
| tgacgagtaa gaggagtttt atttaacgtt ttgtgaggat tttggtttga ggtagcgttt | 1680 |
| ttatacgata gttggcggat cgaattgaga atttgaaaga agtcggcggg aagtttcgtt | 1740 |

-continued

```
tcggtggggg aggggaaatt taaagggtta aatcgaaata gggggaaaaa aaaagcgagt    1800 ttttgtttt cgtgttttga attttgtaac gtgtatagta ttttgttatt acgttatgag     1860
gttttaaaaa attgttttg aacgtagaag atatatatta atattgtggg aaatataaga     1920
aaggataaga aattaagaaa ttataatgtt atttattat ataggttagt taattatgta     1980
ttttgtagag tagttgtata tattttttta agaaaatgta tatagtgttg tatatggagt    2040
tttgtaattt ttttatattg attataattt aattaatttt tattaaagag ataaaagtga    2100
tgttttggtg tttatgtttt ttaggaatta ttaatagtta taattagttt tttagtaatt    2160
ttttaatcgg ttgtattta aaaataatgt tttttatatt taatataaat gtatttttt     2220 tttatatttg ggattaatat tgaaatttat gattttatta tattaaaatt taaattttat    2280
tatattaata tttaaaattg tattagaggt tttatgattt ggtattacgg ttttcgtat    2340 tattttttt ttaaattttt taatttgttt tattaaggtt tttggataat tttagagatt    2400
ttttgtgaag tttgaataaa attttttcga gattttgata attgtattag ttttaggatt    2460
taattggaat agaattaaaa ttttaaaat aagttttat a                          2501
```

<210> SEQ ID NO 10
<211> LENGTH: 2501
<212> TYPE: DNA
<213> ORGANISM: Artificial Sequence
<220> FEATURE:
<223> OTHER INFORMATION: chemically treated genomic DNA (Homo sapiens)

<400> SEQUENCE: 10

```
tataagagtt tgttttaagg attttaattt tattttaatt aagttttaaa gttaatgtaa     60
ttattaaaat ttcgaagaga ttttattaa attttataaa aggttttaa agttgtttag      120 aaattttggt gaaatagatt aggaaatttg gaaggaaat aatgcggaga ttcgtagtat     180
taaattatga gattttaat ataatttaa atattaatgt aataaaattt aaattttggt     240
gtaataaaat tataaatttt aatattggtt ttaagtatag agaaaaagta tatttatgtt    300
gaatgtggaa aatattattt ttaaaatata gtcgattaaa aaattgttgg ggaattgatt    360
ataattattg ataattttta agaaatatag atattaaaat attattttta ttttttaat    420 agaaattggt taaattataa ttaatataag gaggttataa aattttatat ataatattgt    480
atatattttt ttggaaaaat atgtgtaatt gttttgtaaa atatatgatt aattagtttg    540
tgtgatggga taatattgta gttttttaat tttttgttt tttttgtatt tttatagta     600 ttgatgtata tttttttgcgt ttaaaagtaa ttttttaaag ttttataacg tggtaataaa    660
atattatgta cgttataaaa tttagaatac ggaaataaga agttcgtttt ttttttttt     720 ttatttcggt ttggttttt agatttttt tttttatcg gggcgggatt tttcgtcgat     780 ttttttagg ttttagttc ggttcgttaa ttgtcgtata aaggcgttgt tttaggttag     840 agttttata aagcgttggg tgagatttt tttgttcgtt atgtttggtc gcggtaaagg     900
cgggaagggt tttggtaaag gcggcgttaa gcgttatcgt aaagtattgc gcgataatat    960
ttagggtatt attaagtcgg ttattcggcg ttttgttcgt cgcggcggcg tgaagcgtat   1020
tttcggtttt atttacgagg agattcgcgg ggtgttgaag gtgttttttgg agaacgtgat   1080 tcgggacgtc gtgatttata tagagtacgt taagcgtaag acggttatcg ttatggatgt    1140
ggtttacgcg tttaagcgtt agggtcgtat ttttacggt ttcggtggtt gagcgttttt   1200
ttttattaat aaaaggtttt ttttaggggtt ttatttttt tagttgagga gtcgtgatgt   1260
```

```
ttgtttgttt agttttttttt tattatttgt tcgcgtttgt tgagtttgtg ttgttatcgg      1320
agtatgcgtt tttagtcgtt gtaagtaggt attagttatt aatcgttttt tagtaaataa      1380
aatatttaat ataatttgtt ttaggtgttt tagagtttat tgatatgggt cgtcgcgtag      1440
attgtagtgt agtgttatta tggtttattg tagtttttcg attagtcgga atttcgcgtt      1500
tattattacg taaggttaat tattttttta aagatcgggt tttcgtgtgt ttttaggtt       1560 agtttcgata ttttggtttt aatttttcg tttatgttta atgttggtat tatagtagtg       1620
agttattacg tttggttacg atattgttga ggttttaggg ttagttatat ttaaggggta      1680 atttcgtag tgtagtgggg aggaaagtta agtagttata ggttttggc gttgtgaatt        1740 taattgttga atatagtaag aatttattat gtaataattt ttaattagtg gatcgtaaat      1800
aagtttagtt tatcggtttt ggtttaattt ttgagaaagg tgagaatttg aattttttgag     1860 tagaaatacg tagtttatta gtataataaa gtgattataa taaagattaa tttatttttt     1920
gttatttaac gtgggtagag ttttatcgtt gagaatttt tagttttttga gtgtttttttt    1980 atttataatt gaagttgata agatggtatt aaaagtgaga ttttagtaa gtaaatttaa      2040 aggtttgaag gattagtgat taatgggaag tgttaataag ttatatttga ggttatttaa     2100
ttcgagattt tgatttaatt ggtttaagga tattattatt ttgtgggtta gatttgaaaa     2160
ataataattg ttttaaggaa ggaatttgtt ggtatttaaa taaaaatttt ttttttttga     2220
tttttatatg tcgttattta gataaatttt tggtttatat ggttggattt tttttgtta     2280 gttaaatttt gtgttatttt gtgaaaaaga attgagatta ataaacggt agtgagaata     2340 tagggaaaga taaaaattat agtaagttta tttagttatg ttgtagttat ttttataagg    2400
atagggaagg attttgtttt ttatttatta tttaaagtgt gagtataaat tttaaaaata    2460
tatgatatta taggaataat gaagatgttt ttatttgtaa a                        2501

<210> SEQ ID NO 11
<211> LENGTH: 2501
<212> TYPE: DNA
<213> ORGANISM: Artificial Sequence
<220> FEATURE:
<223> OTHER INFORMATION: chemically treated genomic DNA (Homo sapiens)

<400> SEQUENCE: 11
ttgttgtata gaatatttta ttatttaggt attatgtcga gtatttaata gttttttttt       60
ttgttttttt tttttttttt attttgtatt ttggagttaa ttatagtgtt tgttgttttt      120
ttgtttgtgt tataagtttt tattatttag ttttttattta aagtgagaa tatttagtat      180 ttggattttt gttttttgtat tagtttgtta aggataatag ttttttagttt tatttatgtt    240 tttataaaag atatgattta gttttttttta atggttgtat taaatgaagt tttaaagata    300
taatataaat attaattttt ttttttattat aaaaattttt tgttgaatttt gattatattt    360 aaattaacga gttttgtttt atgaaagatt ttttggataa atttgatagt tgatggaata     420
ggagaagttg tttgttatgt ttaaagttaa taagagatta atatttagaa taaatggaga    480
tttgtaaatt aatagaaagt aggtagtaaa gttaagaaaa atagtttaag gtatagttat     540
taaaaggaac gtgattatgt tttttgtagg gatatgggtg gagttggaag tcgttagttt     600
tagtaaattt ataggaat agaaaattag cgagatcgta tggttttatt tataagtggg      660
agttgaataa tgagaatata tggttatatg gcggcgatta atatatattg gtgtttgttg     720
agcggggtgt tggggaggga gagtattagg aagaatagtt aagggatatt gggtttaata     780
tttgggtgat gggatgattt gtatagtaaa ttattatggc gtatatattt atgtaataaa     840
```

```
tttgtatatt ttttatatgt attttagaat tttaaataaa agttggacgg ttaggcgtgg      900
tggtttacgt ttgtaattt agtattttgg gaagtcgagg cgtgtagatt atttaaggtt      960
aggagttcga gattagttcg gttaatatgg tgaaatttcg ttttattaa aaatataaaa     1020 attagttaga tgtggtacgt atttataatt ttatttattc ggaggttga agtagaattg     1080 tttgaattcg agaggcggag gttgtagtga gtcgtcgaga tcgcgttatt gtattttagt   1140
ttgggttata gcgtgagatt acgttataaa ataaaataaa ataatataaa ataaaataaa   1200
ataaaataaa ataaaataaa ataaaataaa ataaaataaa ataaaaaaat aaaataaaat   1260
aaaataaaat aaagtaattt tttttttttt aagcggtttt tattttttt ttttgttttg   1320 tgaagcgggt gtgtaagttt cgggatcgta gcggttttag ggaattttt ttcgcgatgt   1380 ttcggcgcgt tagttcgttg cgtatatttc gttgcggttt tttttttgtt gtttgtttat   1440 ttttttaggtt tcgttgggga tttgggaaag aggggaaggt tttttcggtt agttgcgcgg   1500
cgatttcggg gatttaggg cgttttttg cggtcgacgt tcggggtgta gcggtcgtcg     1560
ggtttggggt cggcgggagt tcgcgggatt ttttagaaga gcggtcggcg tcgtgattta   1620
gtattggggc ggagcgggc gggattattt ttataaggtt cggaggtcgc gaggttttcg   1680 ttggagttc gtcgtcgtag ttttcgttat tagtgagtac gcgcggttcg cgttttcggg    1740 gatgggttt agagttttta gtatgggtt aattcgtagt attaggttcg ggttttcggt    1800 agggttttc gtttatttcg agattcggga cggggtttta ggggatttag gacgttttta    1860
gtgtcgttag cggttttag ggggttcgga gcgtttcggg gagggatggg atttcggggg    1920
cggggagggg gggtagattg cgtttatcgc gttttggtat ttttttttcgg ttttagtaa   1980 attttttttt gttcgttgta gtgtcgttt atatcgtggt ttatttttta gttcgaggta   2040
ggagtatgtg tttggtaggg aagggaggta ggggttgggg ttgtagtta tagttttcg    2100 tttattcgga gagattcgaa ttttttattt ttttcgtcgt gtggttttta tttcgggttt   2160
tttttttgtt tttcgttttt ttcgttatgt ttgttttcg ttttagtgtt gtgtgaaatt    2220
ttcggaggaa tttgttttt tgtttttttt ttgtattttt gatttttt cgggttgttg    2280 cgaggcggag tcggttcggt ttttatattt cgtattttt tttttcgta ggtcgttgcg   2340 cggttttgcg tatgttgttg gtagattagg gttagagttg aaggaggag gtggtgatcg    2400 tggagacgtg gtaggagggt ttatttaaag tttttgcgt aagtgattat gttcgggtaa   2460 ggggagggg tgttgggttt taggggttg tgattaggat t                       2501
```

<210> SEQ ID NO 12
<211> LENGTH: 2501
<212> TYPE: DNA
<213> ORGANISM: Artificial Sequence
<220> FEATURE:
<223> OTHER INFORMATION: chemically treated genomic DNA (Homo sapiens)

<400> SEQUENCE: 12

```
gatttagtt atagttttt aaggtttagt attttttttt tttgttcggg tatggttatt        60
tacgtaggag ttttgagtg agtttttttg ttacgttttt acggttatta ttttttttt       120 ttagttttgg ttttgatttg ttagtagtat gcgtagggtc gcgtagcggt ttgcggggag    180
ggagaagtac gagatgtggg gatcgggtcg atttcgtttc gtagtaattc ggggaggggt    240
taggagtgta gggagggaat aggaaatag gtttttcga agatttata taatattggg      300 gcggggagta ggtatggcgg gagaggcggg gaataggaag gaggttcggg gtaaaagtta   360
```

```
tacgacggag ggataagggg gttcggattt tttcgggtgg gcgagggggtt gtgggttgta    420
gttttagttt ttgttttttt tttttgttag atatatgttt ttatttcgaa ttgggaaata    480
gattacggtg tagggcggta ttgtagcgaa taaagaaaag tttgttggag ttcgggggag    540
gatgttaagg cgcggtgagc gtagtttgtt ttttttttc gttttcgggg ttttattttt    600
tttcgaggcg tttcgggttt tttgaaagtc gttaacggta ttggggacgt tttgggtttt    660
ttaggttttc gtttcgggtt tcgaggtggg cgaggagttt tgtcgggagt tcgggtttga    720
tgttgcgggt tggttttatg ttgggagttt tgagtttat tttcggggac gcgggtcgcg    780
cgtatttatt ggtggcgaag attgcggcgg cgaaatttta gcgaaggttt cgcggttttc    840
gagttttata agggtggttt cgtttcgttt cgttttagtg ttgagttacg gcgtcggtcg    900
tttttttgga ggggtttcgcg gattttcgtc ggttttagtt tcggcggtcg ttgtatttcg    960
ggcgtcggtc gtagaggggc gttttggagt tttcggagtc gtcgcgtagt tggtcgggga   1020
agttttttt tttttttag gttttagcg gggtttaggg agtaaataga tagtaggaag    1080
aggatcgtag cgaagtgtgc gtagcgaatt ggcgcgtcgg gatatcgcgg ggggaaattt   1140
tttaagatcg ttgcgatttc ggagtttgta tattcgtttt ataggtagg ggagaggggt   1200
ggaggtcgtt tagaggaaag gaaattgttt tatttatt tattttattt tattttttta   1260
ttttattta ttttattta ttttattta ttttattta ttttattta ttttgtgtta   1320
ttttattta ttttatgacg tagttttacg ttgtggttta ggttggagtg tagtggcgcg   1380
atttcggcgg tttattgtaa ttttcgtttt tcgggtttaa gtaattttgt tttagttttt   1440
cgagtaggtg gaattatagg tgcgtgttat atttggttga ttttgtatt tttagtagag   1500
acggggtttt attatgttgg tcgggttggt ttcgaattt tgatttagg tgatttgtac   1560
gtttcggttt tttaaagtgt tgggattata ggcgtgagtt attacgtttg gtcgtttaat   1620
ttttatttga agttttgggg tatatgtaga ggatgtgtag gtttgttata taggtgtgtg   1680
cgttatgatg gttgttgtta tagattatt tattattag gtattaagtt tagtattttt   1740
tagttatttt ttttggtatt tttttttttt agtatttcgt ttaataggta ttagtgtgtg   1800
ttgatcgtcg ttatgtgatt atgtgttttt attgtttagt ttttatttat aagtgagatt   1860
atgcggtttc gttggttttt tgttttttgtg tgagtttgtt gaggttaacg gttttagtt   1920
ttatttatgt ttttgtaaag gatatgatta cgtttttttt agtggttgtg ttttaggtta   1980
tttttttttgg ttttgttgtt tattttttgt tgatttgtag attttttattt attttagata   2040
ttgatttttt gttggttttta gatatgatag atagtttttt ttattttatt aattgttaag   2100
tttgtttaag gagttttta tgaaataaaa ttcgttaatt taagtgtaat taaatttagt   2160
aagggatttt tgtggtgggg aagaggttgg tgtttatgtt gtattttaa aattttattt   2220
aatgtagtta ttaaaaagaa ttagattatg ttttttgtgg gaatatggat ggagttagag   2280
gttattattt ttagtaaatt aatgtaggaa tagaaattta aatattggat gttttattt    2340
gtaagtggga gttaaatgat gagaatttat aatataaata aggaaataat agatattgtg   2400
gttgattta gggtgtagga tgggaggaag gagaggagta gaaaagagaa ttattgggta   2460
ttcggtataa tatttgggtg atgaaatatt ttgtataata a                       2501
```

<210> SEQ ID NO 13
<211> LENGTH: 1920
<212> TYPE: DNA
<213> ORGANISM: Artificial Sequence
<220> FEATURE:
<223> OTHER INFORMATION: chemically treated genomic DNA (Homo sapiens)

<400> SEQUENCE: 13

```
ttaggttgtt gtagatatag tttttgtttt tttgaaaaat atgttttagg tgttgggatt      60
ttagatattt gggaaataga gtgtatgtag ttgttgagag gttttgtgtt tggttttttt     120
tattattgag gtgtagaggt gttgtggata gtttagattt atatggtgtt tgaggtgaaa     180
tagaatttt  agtttttta  tgaggttatt ggtatttttg gttgttttta gagttttttg     240
atttagagtt gaatgtaaag taagtgtttg aaatgtagaa gtagttgggg ttgtttatgg     300
tatttgtttt gtttggggtg agagaagatg ttaggttgag gttttagtga ttttaggtat     360
tagttttgaa ggagggtggg gagattgtaa aggggaagtg tttggagggt taatggtttt     420
tgtgtatttt gtgtttttt  gaagtgtgtt gttttttgt  gttggggatt gggatttgtt     480
tttggggaat tgtttagaa  gatggtggtg gattgggggt gggtattttt tagggttgtt     540
aggtttttt  tagttttgta tttgttgtgt tgttttattt tgttaggaag ttttagagat     600
tttgggatg  gggtgggagt gttttttat  tgtgggttta aaaagaagga aggatgtttt     660
tagggttgt  agaaggagga ttagttttaa gttataattt ttttggatt  taaggtaggt     720
tggttggggt tttgtgttta tatggttttt ggtggggggt tgtgtgtttt gggagttttg     780
tggtttgggg aggaaagagg agataagaga taggtgagga ttatggggtt gatttagttg     840
gggtagggat tattgtggaa aaattttggt gaggtggggg gatgtggaaa gagagtggtt     900
tgtgttttgt attttgtgtt gggtatttg  tgttagtgtt ttgttttag gtttgtgt      960
tttgtgtttt gtgttttgtt tttatttgg  gttagttgta ttgtgtttgt gttgtaggaa    1020
ttgtggagtt ggaaagtggg ggtgttgtgg ttgggggggt gttttagttg tgttttggtt    1080
agtgattggt gggttgggtt taaatttagt taggttgggt aggtggtggt tgtgtgattg    1140
gggattgggt gttttgtttt ttttgttttt tttttttttt tttttttttt tttagtttt     1200
ttggttttt  ttagttttta ttggattgt  tgtttgttg  tttttttttt tttttgttt     1260
tttatattat ttttattt   tttgttttgt ttttgtttt  tttttttttt ttgttttttg    1320
tttttttttt tttttttttt tttttaggg  gtggagtttt tttttttttt tttagataat    1380
gttgtggttg tgttttttt  tttgttagtt tgtttaggtt tttgttgtta gtgattttt     1440
tgggttgggg gtggggaggt ggggggggag tgtaggggttg gggaggatga gttggttttt    1500
tttatttttt tgttgttgtt tttttaaga  gggatggaga tttggtttaa gttttttggt    1560
ttatttggag ttgtgatagt tatttttagg gaatagttat gttgtttat  taagtttatt    1620
tttagtggtt tggattttt  aggtagaggt tgtgggattt tgttttttt  aatatttag     1680
tttatttta  aaagggtttg agttggatag gggttaaata ggttttttg  atttggtggg    1740
ttggttagat gtgatagtaa tgttaaggag gttaagtttt tttgtttatt ttttatttt     1800
ttttttttta ttttggatt  ttttggtgtt tttagtatat agaggttttt gagtagtttg    1860
gttgtaggtt ttttatttat ttagagtttt tttttttatg tgtttatttt taattttgta    1920
```

<210> SEQ ID NO 14
<211> LENGTH: 1920
<212> TYPE: DNA
<213> ORGANISM: Artificial Sequence
<220> FEATURE:
<223> OTHER INFORMATION: chemically treated genomic DNA (Homo sapiens)

<400> SEQUENCE: 14

```
tgtagggttg gggataggta tgtgaggggg agaatttga  gtagataggg aatttgtagt      60
```

```
tgggttgttt aagggttttt gtgtattggg ggtgttagga ggtttaggga tggaaaaggg      120
ggaggtgaga aatggataaa gaaatttggt ttttttggta ttgttgttat gtttggttgg      180
tttgttaagt tgaaggggtt tgtttagttt ttgtttggtt taaatttttt tgggaataag      240
ttgggatgtt agaaaaaata aaattttata attttttgttt ggggaattta ggttgttgga      300
ggtgggtttg tagggtagt gtgattgttt tttgggagtg gttgttatag ttttgggtga       360
attgaggagt ttgggttaag ttttttatttt ttttggagag ggtagtagta aggaggtgag     420
gggagttagt ttattttttt taattttgta ttttttttttt attttttat ttttagtttg      480 gaagaattgt tggtggtggg agtttggatg agttggtggg gaaggggatg tagttatagt     540
attgtttggg agggagggga gaagtttgt tttagagggg gaggggagaa gaggaggggg       600
taggagataa ggggaggaag aaaggtgaag gtaaggtgaa ggggtggaga gtgatatgaa      660
gagtgagaga aagagagga tagtggatga gtagatttgg taggggttga aaaaggttaa       720
ggggttggag ggagggagag gaaggaggag gggagtgagg agggtggggt gtttggtttt      780
tagttgtgtg gttattgttt gtttagtttg gttggatttg agtttggttt gttgattgtt     840
ggttgaggtg tagttgaagt agttttttag ttgtggtgtt tttatttttt aattttatgg     900 ttttttgtggt gtgggtgtga tgtagttggt ttggggtgaa ggtaaggtgt ggggtgtggg    960 gtgtgggta ttgggagtga ggtattggtg tgggatgttt ggtgtaaggt gtagggtgtg     1020
ggttgttttt tttttgtgtt tttttatttt gttaaagttt ttttatgatg gttttattt     1080 tggttgggtt agttttgtaa ttttttgtttg ttttttgttt tttttttttt ttttgagttg    1140
tggggttttt ggggtgtgtg gatttttgtt aggggttgtg taggtgtgga gtttttagttg   1200 gtttgttttg ggtttgaaga aagttgtggt ttggagttag tttttttttt atgatttttg    1260
ggggtgtttt ttttttttt tgagtttgtg atgggaaggt gtttttattt tatttttggg     1320
gtttttgaga ttttttggtg aggtggggtg gtgtggtagg tgtagggttg gggagggttt    1380
gatagttttg gagagtgttt gatttagttt tgttgttgtt tttttaggtgg attttttaga   1440 ggtaggtttt agttttggt gtggggaggt ggtgtgtttt agaggggtgt agggtgtgtg     1500
ggggttgttg gtttttgggg tatttttttt ttgtggtttt tttgtttttt tttggagttg    1560
gtgtttgagg ttgttgggat tttagtttgg tgtttttttt tgttttgagt gaggtaggtg    1620
ttgtgggtgg ttttggttat ttttgtattt tgagtgttta ttttgtattt agttttaagt    1680
tggagagttt tggggatagt tgagagtgtt agtggtttta tagggagatt gagggttttg   1740 ttttatttg ggtgttgtgt gggtttgggt tgtttatagt atttttgtgt tttagtgata    1800
ggagaagtta agtgtgaggt ttttaatag ttgtgtgtat tttatttttt aggtatttgg    1860
aattttggtg tttagaatgt gttttttggg agagtaaagg ttgtgtttat ggtagtttgg    1920
```

```
<210> SEQ ID NO 15
<211> LENGTH: 6096
<212> TYPE: DNA
<213> ORGANISM: Artificial Sequence
<220> FEATURE:
<223> OTHER INFORMATION: chemically treated genomic DNA (Homo sapiens)

<400> SEQUENCE: 15
```

```
tattagtgta agatttaaaa ttttttttt gtattgtata gtgagatgtt tagggtttta       60
gtttagtgtt tggatatagt gattttrtggg tttgtttgtt ttgtttttaa gtgaagttgg    120
tgtgttttgg gtggagtaga tagagatttt gggtggtagg ggtttgggaa gatatgggtg     180
gttagggttt tatgtgtttt tattgttgtt ttttgttatt tgtaggtaat ggatgagttg     240
```

```
ggaatgagtt ttttagatta gtttgtgatt aagaaaggta aggaatggtt tgttagggta    300
gagtttggtg agatggtgta ggttttlggt gtatagattt attttttta ttggttgtgt    360 tttttgtgtg ttgttaggtt gggtgtttat taggtatttt ttttggttta gttagatgtt   420
aggtagatgt gtgggtttgg tgagtttgtt tagtattttg tggtttgggg tgggttttag   480
tggattagta tttattgggt tgtagtattg ggagtttggt ttttttttgt tgaggggag    540 ggtattttg tggatttgga gttgatttgt agaatgagtt aaattatttt tttgttttt    600 taagagatgg gaatggaagt gttgtttta tggagttggg gaaatgattt ttattttata    660
gtgttttagt attttggtgt ttggtgggta tttttttttt ttttttttta ggtagggttt   720
tggaggtttt tgggggaatt ttttttttgt gggagttttt tgtggtattt agatttaggg   780
gagtttgtgt gtgagtattg tgtgttaggt tgtgtgtatt tgagttaggg tttatttgtt   840
tttgggtgtt tgtgtttatg tgagtttagg gttttgtgta tgtttgaaat gtttttttta   900
tgggtgtttt agtattttt ggagtgtgag tgtgtttgtt tttgtgaatg tgtttgtgag   960
gtgtgttttt gtatgttggt gtgtattttt ttgtatttgg gggatgtata tattttttaa  1020
tatgtatagt attttgttg tgttttgtat tttgttttt ggtatttgag gattttttaag  1080 tatgtgtggg ttttttttgt gtatatatag gagtatttat gtgattttg gtattagtaa  1140 aatttaggga tatgggattt attttttttg gtttgaggat taagtattgg ttatgatagg  1200
ggaaggtgag agatgataaa aatagagaga tagttagaga ggagtagaga gttagagggg  1260
tttaggtatt gggtagtagt ttttttatat ttggggtagg tgtttgaaag aatttagagg  1320
tgtatatgag tttgaggtgt tttaggtagg tattgttttt atagggtttg gtttgagttg  1380
ttttttaaat gagtgaattt aagtttgggt tttatttgtt ttttatttgt ttttagggga  1440
ggttaaggtg gaagtggtgg tagtagggtt ggggttggat tttaggagt tggggttgag   1500 ttattaggag ttgggggttg ggtggatgat ttggagtgtg tagtagggaa gatgaggtaa  1560
tagggtagga agtgggtggg gggaggtgga attggggttg tgttttgtgt tgtttggaat  1620
tgggagtgtg ggaaagatat taggaatttg gttgtagtgt agttttgttg gtggggtttg  1680
gttggtttat tgtatagagt tttttttgat ttttgaagaa agagatttgt ttgtagtggg  1740
taaaagtttg tttggatttt ttggttatta gaaatatgag tatggtggtg gttttagtt   1800 ttttatttat gtttgggttt aagagattgg gagtttaggt ttattgattt tttgagaaag  1860
attaagattt tgtattttag aaagaggttt ggggattttt gttttgtgta agggtagaag  1920
gattagttgt tttttgagt atttaatt ggaattttgg tttgaagttg agataggaga   1980
ttggatgtga ggtttttta gagttggttt ttttaaata attttaaaa tttagatt     2040 ttaggggtat gttgaaattt tttaaagtag tttaaagaat ataatgagag ttttaatatt  2100
ttaggtggtg gtgtgttggt tttttggagt ggggtgggat gtggttgtgt ggatttatgt  2160
gtataattgt gtgggatggg gttatgtgga tttatgtgta taattgtggg atttagtgt   2220 tagtgggatt ttagtgttag tgggatttta gtgttagtgg gattttagtg ttagtgggat  2280
tttagtgtta gtgggatttt agtgttagtg ggattttagt gttagtgggt tgtggttta   2340 gtggagtgag tggagtgttg gtgatttgag tggagattgt gttttggatg ttttagttta  2400
gatgttaagt tatagtttgt gtagtagtag taaaggggaa ggggtaggag ttgggtatag  2460
ttggatttgg aggttgtgat ttaggggaaa gtgtgggtgg ttgatttagg gtagttgtgg  2520
tggtgaggta ggtgggtttt ttgttttttg gagttgtttt tttttatatt tgtttttggt  2580
```

-continued

```
gtttttagta gttttttattt tggtttttttg tggttattgt gggatttggt gttgttgtta    2640
gtttagtggg gagtgaatta gtgttttttt ttgtttttgg ttttttttgat ggtatgagga     2700
atttttgttt tgttttatag atttttggtt tttgttgagt gtggtattgg agtttgtttt     2760
gttagggttt tggaattaga gaaagttgtt ttttggttat ttgaagtgtt ggattttttat    2820
agtgttttttt agtttgggtg ggagtggtgg ttgtgttgtt gaaggttggg gttttttggtg   2880
tgaaagggag gtagtgtag ttttagtttt attttagaag tggttttttgt attgttgtgg    2940
tgggtgttttt tgggttttga ttttgttagt gttgtggggt agaggtattt ggagtttgta    3000
gggtttagat ttgggttgga aaagttttgt tgattgtagg taagtgtttg ggaggggtgg    3060
ttaggtgaag ttttggtgtt ttattatata tttttgggtt ttatgttagt tgtatttgtg    3120
gtattgggta ggaaatggta gggttgaggt tgattttagg agtataaggg agttttttat    3180
tttttgttta tatttgttat ttttagtttt gtaatttatt ttagatatat agaaagtaag    3240
taggattggt ggggagatgg agtttaatag gaatatttttt tagtagtgag taggggttgt   3300
atgggatgtg ggaggagttt agaggaggtg tggagagtgt ttgaggttgg gtgagtgttt    3360
agagggggaga tagttgaatt gggtttaaga ggtgtttagt gggtgtttgt tgaatgaatg   3420
agtgatgggg ttttgaagttt gagtgtattg aaagaggggg tgtgtaaaaa gggttttttt   3480
tattatatag gatatagtat atgtaaattt ttttttttgtg gaaaagttag ataggttaaa   3540
aaggttataa ataaattagt tgggtatggt ggtgtgtgtt tgtagtttta gttattaggg   3600
aggttgagtt aggggaattg tttgaatttg ggaggtggag attgtagtga gttaagattg    3660
tgttattgta tttttagtttg gaaatagagt gagattttgt tttggaaaaa aaaaaaaaaa    3720
gttataaatt gtgtgtgggt tttaggttat ataattagag ttggagggga gtggttaagg    3780
atgagaattg agatggattt tttgtttttt ttggaggaga gtggtggtt gtttatttgg    3840
gggtggggaa tttttttttta tgggtttagt tgtttaattt taggggatttt ttaggatagg   3900
agttgatgta aatagttgtt ttattttttg ttgtttttgg ttttggagaa ggaggaggga   3960
gttggggagg gttttttattt tttagataat ttttaagtag ttaggatatg ggtgagatga   4020
gtgagatatt gattttgtggg atagaatttg agagggtgtt aaaaaattta gtaattaaga   4080
taaataggtt gggtgtagtg gtttatgttt gtaattttag tattttggga ggttggatta    4140
tttgaggtta agagttttgag attagttgg ttaagatggt gaaatttttat ttttattaaa   4200
aatataaaaa ttagtttagt gtggtggtgt tagtttgtaa ttttagttat ttaggaggtt    4260
gaggtaagag aattgtttga tttaggaggt agaggttgta gtgagttgag attatgttat    4320
tgtattttag tttggataat agagggagat tattttaaaa aaaaaaaaaa aaaaaaaaaa    4380
aaaaaagagg ttgggtggtg gtggtttata ttatgtgatt ttagtatttt gggaggttga    4440
ggtgggtgga ttatttgagg tttggagttt gagattagtt tggttaatat ggtgaaattt    4500
tgttttttat aaaatataaa aaattagttg ggtggggtgg taggtatttg taattttagt    4560
tattttggag gttgaggtag gagaattttt tgaatttgtg gggtggaggt tgtagtgaat    4620
taagattata ttattgtatt ttagtttgga taataatagt aaaatttttgt tttaaaaaaa   4680
aaaaaaattt ttttttttga gatatagttt tattttttttg tttaggttgg ggtgtagtat    4740
tatgatttta gttattgta atttttgttt tttagatttt tgtattttag tttttttaagt    4800
agttgggatt ataggtattt gttattatgt ttagttaatt tttgtattttt tagtaggggt   4860
gtggttttat tatgttggtt aggttgggttt tgaattttttg attttaagtg atttgttttgt  4920
tttagttatt taaagtgttg ggattatagg tgtgagttat tatgtttggt ttttttaaat    4980
```

```
gaaaatagtg taaaaattta tgataaataa aatattaaaa atttattgaa tttgtatttt    5040 tataatttt  ttttatttgt  tttttaggtt attttttgtt ttagaaagta atttaaaaaa    5100
tgtgtagatg gagtttggat tttatttgaa aatggtggga gttatggaaa attttggagt    5160
aggggagtga aggatagaaa ttatatgtaa aagaaatttt gggttgggtg tagtggttta    5220
tgtttgtaat tttagtattt tgggaggttg aggtaggtgg attatttgag gttaggagat    5280
tgagattagt ttgattaata tggtgaaatg ttattttat taaaaatata aaaaaaatta    5340
gttaggtatg gtggtgtatg tttgtagttt tagttatttt ggaggttgag ataggaaaat    5400
tgtttgaatt tgggaggtgg aggttgtagt gagttaagat tgtgttattg tattttagtt    5460
tgggtaataa gagtaaaatt ttattttaaa aaaaagaaa gaaagaaatt ttttggtagt     5520
tgatgagaag gaaatttaat tggtaggttt tagtagggga gatgaggaga ttttagggag    5580
ggtatttgta tatgttgtgt tttagtgtgg gttagggagt aggttattat ttttttttgtt   5640 tatttttttt ttgtttaat tttttaagt tttggattag tggtatttta agtgtagttt      5700
aaggaattat atgtattagg attttaggg ggtgtttgtt aaaaatgtaa attttggtta     5760
ggtgtagtgg tttatatttg taatttagt attttgggag gttgaggtgg gtggattatg     5820
aggttaggag attgagatta ttttggtaaa tatggtgaaa ttttattttt attaaaaaaa    5880
taaaaataaa ttaaaaaaaa tattagttgg gtgtggtgg gggtgtttgt agttttagtt     5940
atttgggagg ttgaggtagg agaatggtgt gaatttggga ggtggagttt gtagtgagtt    6000
gagattgtgt tattgtattt tagttggggt gatagagtga gattttgttt taaaaaaaaa    6060
aaagtaaatt ttttggggtat tattttatat tgattg                             6096

<210> SEQ ID NO 16
<211> LENGTH: 6096
<212> TYPE: DNA
<213> ORGANISM: Artificial Sequence
<220> FEATURE:
<223> OTHER INFORMATION: chemically treated genomic DNA (Homo sapiens)

<400> SEQUENCE: 16
tagttaatgt ggggtggtgt ttaagaaatt tgttttttt tttttgaggt agagttttgt        60
tttgttgttt aggttggggt gtagtggtgt aatttagtt tattgtaagt tttgtttttt       120
gggtttatgt tattttttg ttttagtttt ttgagtagtt gggattatag gtgtttgtta       180
ttatgtttag ttaatgtttt ttttggtttg ttttttgtttt tttagtagag atggggtttt     240
attgtgtttt ttaggatggt tttgattttt tgattttgtg atttatttgt tttggttttt     300
taaagtgttg ggattatagg tgtgagttat tgtatttggt taaaatttgt atttttaata    360
agtatttttt gggggttttg atgtatgtgg ttttttggat tatatttagg gtattattgg    420
tttaaagttt gaagggggttg gagtaagagg aaggtagatg ggaggagtag tgatttgttt    480 tttggttat attgggggtat agtatgtgta aatgtttttt ttagagtttt tttattttt      540 ttgttgggat ttgttgatta agttttttt ttattaattg ttagagggtt tttttttttt       600 tttttttta agatggagtt ttgttttttgt tgtttaggtt ggagtgtaat ggtataattt     660
tggtttattg taattttgtgt ttttttgggtt taagtgattt ttttgtttta gttttttggag   720 tagttgggat tataggtgtg tattattatg tttggttaat ttttttgta ttttagtag      780 agatgatatt ttattatgtt ggttaggttg gtttaatttt tttgatttta ggtaatttat     840
ttgttttggt ttttaaagt gttgggatta taggtataag ttattgtgtt tggtttaggg       900
```

```
tttttttttat ataaattttt tatttttat ttttttgttt taaggtttttt tatagtttt      960
attattttta ggtaaagttt aaattttatt tgtatatttt ttaagttgtt ttttgggta      1020
gagagtagtt tgggaggtag gtgagaaagg gttgtggaag tgtaagttta gtaaattttt     1080
gatattttgt ttattgtgga tttttgtatt atttttattt aaaaaggtta agtgtggtgg     1140
tttatgtttg taattttagt attttgggtg gttgaagtgg gtaggttatt tgaggttagg     1200
agtttaagat tagtttggtt aatatggtga aattatgttt ttattaaaaa tataaaaatt     1260
agttgggtgt ggtgataggt atttgtaatt ttagttattt gggaggttga ggtatgagaa     1320
tttgagaggt agaggttgta gtgagttgag attgtggtgt tgtattttaa tttgggtgag     1380
agagtaaaat tgtgttttga aaaaaagat ttttttttt tttgagatag agttttgttg      1440
ttgttgttta ggttggagtg taatggtgtg attttggttt attgtaattt ttgttttgta    1500
ggtttaaggg atttttttgt tttagttttt ggagtagttg ggattatagg tgtttgttat    1560
tttatttagt taattttgt atttttagta gaaatggggt tttattatat tggttaggtt    1620
ggttttgaat tttagatttt aggtgattta tttgttttgg ttttttaaag tgttgggatt   1680
atatggtgtg agttattgtt gtttggtttt ttttttttt tttttttttt tttttttttt   1740
gagatagttt ttttttgttg tttaggttgg agtatagtgg tatgattttg gtttattgta   1800
attttgtttt tttgggttaa gtaattttttt tgttttagtt ttttgagtgg ttgggattat   1860
aggttagtgt tattatattg ggttaattttt tgtattttta gtagagatgg ggttttatta   1920
ttttggttag gttggttttg aattttttgat tttaagtgat tggttttttt aaagtgttgg    1980
gattatagat gtgagttatt gtgtttggtt tatttatttt gattattgag ttttttggta    2040
tttttttaaa ttttgtttta gaagttagta ttttatttat tttatttatg ttttggttgt    2100
ttagagattg tttgggaagt ggagattttt tttagttttt ttttttttt ttagggttaa    2160
agatagtaag gaatagggtg attgtttata ttagttttg ttttagagat ttttgagat    2220
tggatagttg agtttgtgga gagggatttt ttattttta gtaggtaatt atttattttt    2280
ttttagaggg aatgagggat ttattttagt ttttattttt gattattttt tttagtttt    2340
gattgtataa tttgaaattt atatgggtt tgtaatttt tttttttttt tttgagatgg     2400
agttttgttt tgttttagg ttggagtgta gtggtgtgat tttggtttat tgtaattttt    2460
gttttttggg tttaagtgat tttttggtt tagtttttt agtagttggg attatagatg    2520
tgtattatta tgtttggtta atttgttgt aattttttta atttgtttgg tttttttata    2580
gggagaggat ttgtatatgt tgtgttttgt gtgatgaaag gagttttttt tatatatttt   2640
ttttttaat gtatttagat tttaaagttt attatttatt tatttaataa atatttatta    2700
agtattttt gaatttggtt taattatttt tttttaggt atttatttaa ttttgggtat     2760
tttttgtgtt tttttgagt tttttttgtg tttatatag ttttgtttta ttgttggaaa    2820
atattttgt taagttttgt tttttatta gtttgtttg tttttgtgt gtttgggata       2880
ggttgtaaaa ttgaggtga taaatgtggg taggaaatgg agggttttt tatattttta    2940
gggttggttt tagttttgtt attttttgtt taatattgtg gatgtaattg gtatgggatt    3000
tggaagtgtg tggtaaagtg ttggggtttt gtttggttgt ttttttgga tgtttgtttg    3060
tagttagtga agttttttta atttaggttt gggttttgtg agttttaggt gtttttgttt    3120
tgtggtgttg gtgaagttga agtttgagaa tgtttattgt agtgatgtga aggttgtttt    3180
tggggtgggg ttgaggttgt agttgttttt ttttgtatt aaggatttta atttttagtg    3240
atgtagttgt tgttttttgt taggttggga ggtattgtag ggatttgatg ttttaggtgg   3300
```

```
ttaaagagtg attttttttg attttagggt tttggtgggg taggttttag tattgtattt    3360
ggtggaggtt gaaggtttgt ggggtaggat aggagttttt tgtgttgttg gaagggttga    3420
ggatgaagga gggtgttaat ttattttta ttgggttggt ggtaatgttg aattttgtag     3480
tgattgtgga gggttaaggt gaaaattgtt ggggtgttg agggtaggtg tggggagggg     3540
tggttttagg gagtaaggag tttatttgtt ttgttgttgt agttgttttg ggttgattgt    3600
ttatgttttt ttttgggtta tgattttggg atttaattgt gtttggtttt tgttttttt    3660
tttttgttgt tgttgtgtgg gttgtaattt gatgtttagg ttggggtgtt tagggtgtag    3720
tttttgttta ggttgttagt gttttatttg ttttattggg ttatagatttt gttggtgttg   3780
gggttttgtt ggtgttgggg ttttgttggt gttggggttt tgttggtgtt ggggttttgt    3840
tggtgttggg gttttgttgg tgttggggtt tgttggtgt tggggttttg tggttgtgta     3900
tgtgagtttg tgtggttttg ttttgtgtgg ttgtgtatgt gagtttgtgt ggttgtgttt    3960
tgttttgttt tagggagtta gtgtgttgtt atttgggatg ttaggatttt tgttgtgttt    4020
tttggattgt tttggggggat tttggtgtat ttttaggatt taggagtttt ggaagttgtt   4080
tgagagaaat tagttttggg agggttttgt atttagtttt ttgttttggt tttggattgg    4140
ggttttgggt taaggtgttt agaggaatag ttgattttt tatttttgtg tagggtagag     4200
attttttaaat ttttttttaa aatgtagggt tttagttttt ttagggagt tagtgaattt    4260
agattttag ttttttgagt ttaagtatga atagggaatt ggggattatt attatgttta    4320
tatttttggt ggttaggaag tttaggtagg ttttttgttta ttgtagatgg attttttttt   4380
ttaggggtta agaaaggttt tgtatagtaa gttaattaag tttttattagt agagttgtgt   4440
tgtaattagg ttttttagtgt tttttttata tttttagttt taagtgatat aggatatagt   4500
tttaatttta ttttttttta tttatttttt gttttgttgt tttatttttt ttgttatata    4560
ttttaagtta tttatttaat ttttagtttt tggtaattta gttttagttt ttggaagttt    4620
agttttagtt ttgttattat tatttttatt ttggtttttt ttgagaataa gtggagggta    4680
aatagagttt aggttttgaat ttatttgttt gaaaaataat ttaagttaaa ttttgtggga   4740
gtagtgtttg tttggggtat tttaggttta tgtgtatttt tgaattttt tgggtatttg     4800
ttttaaatgt aaagaggttg ttatttaatg tttgggtttt tttgatttt tgtttttttt     4860
tggttgtttt tttgttttg ttgttttta ttttttttg ttatggttag tatttggttt       4920
ttaggttaga aaaggtggat tttgtgtttt tggattttat taatgttagg agttatataa    4980
atattttat atatatatag agagggtttg tgtatgtttg gaaattttta gatattaaag     5040
aataaagtgt aggatataat agagatattg tatatattga gaaatgtgta tatttttaa     5100
atgtagagaa atgtatatta atatatagag atatatttta taaatatatt tatagaaata    5160
gatatattta tattttaaga aatattaaga tatttatgaa gggaatattt tagatatgta    5220
taggattttg aatttatatg gatatagata tttaggagta ggtgggtttt gatttaggtg    5280
tatatagttt aatatatagt atttatatat aagtttttt aagtttaaat gttgtaagag     5340
atttttatag aaagaaaatt ttttttagagg tttttaaggt tttgtttgga aggaagagga   5400
agaaagtgtt tgttaggtat tgaaatgtta aggtattgta aagtgaaaat tattttttta    5460
attttgtggg aatagtattt ttatttttat tttttaggga aataggaag tggtttaatt     5520
tgttttgtaa attaattta gatttataag agtgtttttt ttttggtgg ggagaggtta     5580
ggttttagt gttgtagttt agtgaatgtt gatttgttga ggtttatttt aggttatagg     5640
```

```
gtgttgggta aatttattaa gtttgtatgt ttgtttaata tttggttggg ttaggaagag      5700
tgtttggtgg atatttagtt tggtgatata taggaggtat ggttggtgaa gaaaatggat      5760
ttgtgtatta agggtttgta ttattttgtt gggttttgtt ttgatagatt attttttatt      5820
ttttttgatt atggattggt ttaggaggtt tattttggt ttgtttattg tttgtaaata       5880
gtagagggta gtggtgaggg tgtataaagt tttagttgtt tatgttttttt taagttttttg   5940 ttatttaggg ttttttgtttg ttttgtttaa ggtgtattag ttttgtttgg ggtggtgatg    6000
ggtaggttta ggaattgtta tgtttaggta ttgagttgga gttttgggta ttttattgtg     6060
tagtgtaaaa agggaatttt gaattttata ttggta                               6096
```

<210> SEQ ID NO 17
<211> LENGTH: 2501
<212> TYPE: DNA
<213> ORGANISM: Artificial Sequence
<220> FEATURE:
<223> OTHER INFORMATION: chemically treated genomic DNA (Homo sapiens)

<400> SEQUENCE: 17

```
tttgtaaatg gagatatttt tattattttt atagtattat atgtttttaa agtttgtatt       60
tatattttgg gtgataaatg aaggataaga ttttttttta tttttgtgag gatgattata      120
gtatgattgg atgggtttgt tatgattttt atttttttt gtgttttttat tattgtttta     180 ttaattttag ttttttttta tagggtagta tagaatttaa ttagtagaaa gagatttagt     240
tatgtagatt agagatttgt ttaagtgatg gtatgtaaga attaggaagg aaagttttttt    300 gtttaaatat taataggttt tttttttaaa gtaattatta ttttttaaat ttaatttata    360
aggtgatagt attttttaaat taattaaatt agaattttgg gttggataat tttaaatatg   420
atttattagt atttttttatt aattattggt tttttaggtt tttaagttta ttttattagga   480 atttttatttt taatattatt ttattaattt tagttgtaaa taagagaata tttaaaggtt   540
gaggaatttt tagtggtaaa gttttgttta tgttaagtaa taaaggataa gttagttttt    600
gttgtgatta ttttgttgta ttgataagtt atgtattttt atttaaggat ttaaattttt   660 attttttta agaattgggt taaaattgat aaattaaatt tatttatggt ttattgatta    720
aaggttgttg tataataagt ttttgttatg tttagtagtt ggatttatag tgttagaaat   780
ttataattgt ttgattttttt ttttattat attgtgaaaa ttgttttta aatgtaatta     840 attttaaaat tttaatagta ttgtggttag gtgtggtggt ttattattgt aatattaata   900
ttaggtatag gtgagggggat tgaggttagg atattgaaat tagtttggga aatatatgga   960 gattggttttt ttggaaaaaat aattagtttt gtgtggtggt gggtgtgagg ttttggttaa  1020
ttgggaggtt atagtgagtt atgatgatat tgtattatag tttgtgtgat ggtttatgtt   1080
agtaagtttt ggagtatttg aaataagttg tgttgggtat tttatttatt ggagagtgat   1140
tagtgattga tgtttatttta tagtgattag agatgtatgt tttgatagta gtataaattt   1200
agtaggtgtg aataaatggt aaagagaaat tgggtaaata agtattatgg ttttttagtt   1260
gagaaagtgg gggttttaaa aagggttttt tgttgataga aagggatgtt taattattga   1320
aattgtagag ggtgtggttt tggtgtttga gtgtgtagat tatatttatg gtggtgattg   1380
ttttgtgttt ggtgtgtttt gtataggtta tggtgttttg gattatgttt tttaggaata   1440 ttttttagtat tttgtgagtt tttttgtaga tgaggttgga gatgtgtttt atgttgttgt   1500
ggtgagtaag gtgttggatg gttggtttgg tgatgttttg gatattgttg tgtagtattt   1560
tatggtggtg tttagtgttg ttttttgttaa gattttttttt gttttttgttg tggttagata  1620
```

```
tgatgagtaa gaggagtttt atttaatgtt ttgtgaggat tttggtttga ggtagtgttt      1680
ttatatgata gttggtggat tgaattgaga atttgaaaga agttggtggg aagttttgtt      1740
ttggtggggg aggggaaatt taaagggtta aattgaaata ggggaaaaa aaaagtgagt       1800 ttttttgtttt tgtgttttga attttgtaat gtgtatagta ttttgttatt atgttatgag    1860
gttttaaaaa attgttttg aatgtagaag atatatatta atattgtggg aaatataaga      1920
aaggataaga aattaagaaa ttataatgtt attttattat ataggttagt taattatgta     1980
ttttgtagag tagttgtata tattttttta agaaaatgta tatagtgttg tatatggagt     2040
tttgtaattt tttatattg attataattt aattaatttt tattaaagag ataaaagtga      2100
tgttttggtg tttatgtttt ttaggaatta ttaatagtta taattagttt tttagtaatt     2160
ttttaattgg ttgtatttta aaaataatgt ttttatatt taatataaat gtattttttt      2220
tttatatttg ggattaatat tgaaatttat gatttatta tattaaaatt taaattttat      2280
tatattaata tttaaaattg tattagaggt tttatgattt ggtattatgg ttttttgtat     2340 tattttttt ttaaattttt taatttgttt tattaaggtt tttggataat tttagagatt      2400
ttttgtgaag tttgaataaa atttttttga gattttgata attgtattag ttttaggatt     2460
taattggaat agaattaaaa tttttaaaat aagttttat a                         2501

<210> SEQ ID NO 18
<211> LENGTH: 2501
<212> TYPE: DNA
<213> ORGANISM: Artificial Sequence
<220> FEATURE:
<223> OTHER INFORMATION: chemically treated genomic DNA (Homo sapiens)

<400> SEQUENCE: 18
tataagagtt tgttttaagg attttaattt tattttaatt aagttttaaa gttaatgtaa      60
ttattaaaat tttgaagaga ttttatttaa attttataaa aggttttaa agttgtttag     120 aaattttggt gaaatagatt aggaaatttg gaaaggaaat aatgtggaga tttgtagtat     180
taaattatga gattttaat ataatttaa atattaatgt aataaaattt aaattttggt      240
gtaataaaat tataaatttt aatattggtt ttaagtatag agaaaaagta tatttatgtt     300
gaatgtggaa aatattattt ttaaaatata gttgattaaa aaattgttgg ggaattgatt     360
ataattattg ataattttta agaaatatag atattaaaat attattttta tttttttaat    420
agaaattggt taaattataa ttaatataag gaggttataa aattttatat ataatattgt    480
atatattttt ttggaaaaat atgtgtaatt gttttgtaaa atatatgatt aattagtttg    540
tgtgatggga taatattgta gttttttaat tttttgtttt tttttgtatt tttttatagta   600 ttgatgtata ttttttgtgt ttaaaagtaa ttttttaaag tttataatg tggtaataaa    660 atattatgta tgttataaaa tttagaatat ggaaataaga agtttgtttt tttttttttt    720
ttattttggt ttggttttt agattttttt ttttttattg gggtgggatt ttttgttgat     780 ttttttagg ttttagttt ggtttgttaa ttgttgtata aaggtgttgt tttaggttag      840 agttttttata aagtgttggg tgagattttt tttgtttgtt atgtttggtt gtggtaaagg   900
tgggaagggt tttggtaaag gtggtgttaa gtgttattga aaagtattgt gtgataatat    960
ttagggtatt attaagttgg ttatttggtg ttttgtttgt tgtggtggtg tgaagtgtat   1020
ttttggtttt atttatgagg agatttgtgg ggtgttgaag gtgttttttgg agaatgtgat  1080 ttgggatgtt gtgatttata tagagtatgt taagtgtaag atggttattg ttatggatgt  1140
```

```
ggtttatgtg tttaagtgtt agggttgtat ttttatggt tttggtggtt gagtgttttt    1200
ttttattaat aaaaggtttt ttttagggtt tttattttt tagttgagga gttgtgatgt    1260
ttgtttgttt agtttttttt tattatttgt ttgtgtttgt tgagtttgtg ttgttattgg    1320
agtatgtgtt tttagttgtt gtaagtaggt attagttatt aattgttttt tagtaaataa    1380
aatatttaat ataatttgtt ttaggtgttt tagagtttat tgatatgggt tgttgtgtag    1440
attgtagtgt agtgttatta tggtttattg tagttttttg attagttgga attttgtgtt    1500
tattattatg taaggttaat tatttttta aagattgggt ttttgtgtgt tttttaggtt    1560
agttttgata ttttggtttt aattttttg tttatgttta atgttggtat tatagtagtg    1620
agttattatg tttggttatg atattgttga ggttttaggg ttagttatat ttaagggta    1680 attttgtag tgtagtgggg aggaaagtta agtagttata ggttttggt gttgtgaatt    1740 taattgttga atatagtaag aatttattat gtaataattt ttaattagtg gattgtaaat    1800
aagtttagtt tattggtttt ggtttaattt ttgagaaagg tgagaatttg aattttgag    1860 tagaaatatg tagtttatta gtataataaa gtgattataa taaagattaa tttattttt    1920 gttatttaat gtgggtagag tttattgtt gagaattttt tagttttga gtgttttttt    1980 atttataatt gaagttgata agatggtatt aaaagtgaga ttttagtaa gtaaatttaa    2040 aggtttgaag gattagtgat taatgggaag tgttaataag ttatatttga ggttatttaa    2100
tttgagattt tgatttaatt ggtttaagga tattattatt ttgtgggtta gatttgaaaa    2160
ataataattg ttttaaggaa ggaatttgtt ggtatttaaa taaaaatttt tttttttga    2220 tttttatatg ttgttattta gataaatttt tggtttatat ggttggattt ttttttgtta    2280
gttaaatttt gtgttatttt gtgaaaaaga attgagatta ataaaatggt agtgagaata    2340
tagggaaaga taaaaattat agtaagttta tttagttatg ttgtagttat ttttataagg    2400 ataggaagg attttgtttt ttattttatta tttaaagtgt gagtataaat tttaaaaata    2460
tatgatatta taggaataat gaagatgttt ttatttgtaa a                        2501
```

<210> SEQ ID NO 19
<211> LENGTH: 2501
<212> TYPE: DNA
<213> ORGANISM: Artificial Sequence
<220> FEATURE:
<223> OTHER INFORMATION: chemically treated genomic DNA (Homo sapiens)

<400> SEQUENCE: 19

```
ttgttgtata gaatatttta ttatttaggt attatgttga gtatttaata gttttttttt     60
ttgttttttt tttttttttt attttgtatt ttggagttaa ttatagtgtt tgttgttttt    120
ttgtttgtgt tataagtttt tattatttag tttttattta taagtgagaa tatttagtat    180 ttggatttt gttttgtat tagtttgtta aggataatag ttttagtttt tatttatgtt    240
tttataaaag atatgattta gttttttta atggttgtat taaatgaagt tttaaagata    300
taatataaat attaattttt ttttattat aaaaatttt tgttgaattt gattatattt    360
aaattaatga gttttgtttt atgaaagatt ttttggataa atttgatagt tgatggaata    420
ggagaagttg tttgttatgt ttaaagttaa taagagatta atatttagaa taaatggaga    480
tttgtaaatt aatagaaagt aggtagtaaa gttaaagaaa atagtttaag gtatagttat    540
taaaaggaat gtgattatgt ttttgtagg gatatgggtg gagttggaag ttgttagttt    600
tagtaaattt atataggaat agaaaattag tgagattgta tggttttatt tataagtggg    660
agttgaataa tgagaatata tggttatatg gtggtgatta atatatattg gtgtttgttg    720
```

```
agtggggtgt tggggaggga gagtattagg aagaatagtt aagggatatt gggtttaata      780
tttgggtgat gggatgattt gtatagtaaa ttattatggt gtatatattt atgtaataaa      840
tttgtatatt ttttatatgt attttagaat tttaaataaa agttggatgg ttaggtgtgg      900
tggtttatgt ttgtaattt agtattttgg gaagttgagg tgtgtagatt atttaaggtt      960
aggagtttga gattagtttg gttaatatgg tgaaattttg ttttattaa aaatataaaa     1020 attagttaga tgtggtatgt atttataatt ttatttattt gggaggttga agtagaattg     1080
tttgaatttg agaggtggag gttgtagtga gttgttgaga ttgtgttatt gtattttagt     1140
ttgggttata gtgtgagatt atgttataaa ataaataaa ataatataaa ataaaataaa     1200
ataaaataaa ataaaataaa ataaaataaa ataaaataaa ataaaaaaat aaaataaaat     1260
aaaataaaat aaagtaattt tttttttttt aagtggtttt tatttttttt ttttgttttg     1320
tgaagtgggt gtgtaagttt tgggattgta gtggttttag ggaattttt tttgtgatgt     1380 tttggtgtgt tagtttgttg tgtatatttt ggtgtggttt ttttttttgtt gtttgtttat     1440 tttttaggtt ttgttgggga tttgggaaag agggaaaggt tttttttggtt agttgtgtgg     1500 tgattttggg gattttaggg tgttttttg tggttgatgt ttggggtgta gtggttgttg     1560
gggttggggt tggtgggagt ttgtgggatt ttttagaaga gtggttggtg ttgtgattta     1620 gtattgggt ggagtggggt gggattattt ttataaggtt tggaggttgt gaggttttg     1680 ttggagtttt gttgttgtag ttttttgttat tagtgagtat gtgtggtttg tgtttttggg     1740
gatggggttt agagttttta gtatgggtt aatttgtagt attaggtttg ggtttttggt     1800 agggttttttt gtttatttg agatttggga tgggggttta ggggatttag gatgttttta     1860
gtgttgttag tggttttttag ggggtttgga gtgtttgggg gagggatggg attttggggg     1920
tggggagggg gggtagattg tgtttattgt gttttggtat tttttttggg gttttagtaa     1980
attttttttt gtttgttgta gtgttgtttt atattgtggt ttattttta gtttgaggta     2040 ggagtatgtg tttggtaggg aagggaggta ggggttgggg ttgtagttta tagttttttg     2100
tttatttgga gagatttgaa ttttttatt ttttgttgt gtggttttta ttttgggttt     2160 ttttttttgtt ttttgtttt tttgtatgt ttgttttttg tttagtgtt gtgtgaaatt     2220 tttggaggaa tttgtttttt tgttttttt ttgtattttt gatttttttt tgggttgttg     2280
tgaggtggag ttggtttggt ttttatattt tgtattttt tttttttgta ggttgttgtg     2340
tggttttgtg tatgttgttg gtagattagg gttagagttg gaaggaggag gtggtgattg     2400
tggagatgtg gtaggagggt ttatttaaag ttttttgtgt aagtgattat gtttgggtaa     2460
ggggaggggg tgttgggttt taggggttg tgattaggat t                          2501

<210> SEQ ID NO 20
<211> LENGTH: 2501
<212> TYPE: DNA
<213> ORGANISM: Artificial Sequence
<220> FEATURE:
<223> OTHER INFORMATION: chemically treated genomic DNA (Homo sapiens)

<400> SEQUENCE: 20
gattttagtt atagtttttt aaggtttagt atttttttt tttgtttggg tatggttatt      60
tatgtaggag gttttgagtg agtttttttg ttatgttttt atggttatta tttttttttt     120
ttagttttgg ttttgatttg ttagtagtat gtgtagggt gtgtagtggt ttgtggggag     180
ggagaagtat gagatgtggg gattgggttg attttgttt gtagtaattt ggggaggggt     240
```

-continued

```
taggagtgta gggagggaat agggaaatag gttttttttga agattttata taatattggg    300
gtggggagta ggtatggtgg gagaggtggg gaataggaag gaggtttggg gtaaaagtta    360
tatgatggag ggataagggg gtttggattt ttttgggtgg gtgaggggtt gtgggttgta    420
gttttagttt ttgttttttt ttttttgttag atatatgttt ttattttgaa ttgggaaata    480
gattatggtg tagggtggta ttgtagtgaa taaagaaaag tttgttggag tttggggggag   540
gatgttaagg tgtggtgagt gtagtttgtt tttttttttt gtttttgggg ttttattttt    600
ttttgaggtg ttttgggttt tttgaaagtt gttaatggta ttggggatgt tttgggtttt    660
ttaggttttt gttttgggtt ttgaggtggg tgaggagttt tgttgggagt ttgggtttga    720
tgttgtgggt tggttttatg ttgggagttt tgagtttttat ttttgggggat gtgggttgtg   780
tgtatttatt ggtggtgaag attgggtggg tgaaatttta gtgaaggttt tgtggttttt    840
gagttttata agggtggttt tgttttgttt tgttttagtg ttgagttatg gtgttggttg    900
ttttttttgga gggttttgtg gattttttgtt ggttttagtt ttggtggttg ttgtattttg   960
ggtgttggtt gtagagggt gttttggagt ttttggagtt gttgtgtagt tggttgggga    1020
agtttttttt ttttttttag gttttttagtg gggtttaggg agtaaataga tagtaggaag   1080
aggattgtag tgaagtgtgt gtagtgaatt ggtgtgttgg gatattgtgg ggggaaattt    1140
tttaagattg ttgtgatttt ggagtttgta tatttgttttt ataggtgtagg ggagaggggt   1200
ggaggttgtt tagaggaaag gaaattgttt tattttattt tatttttattt tattttttta   1260
ttttattta ttttattttta ttttattttta ttttattttta ttttattttta ttttgtgtta   1320
ttttattttta ttttatgatg tagtttttatg ttgtggttta ggttggagtg tagtggtgtg   1380
attttggtgg tttattgtaa ttttttgtttt ttgggtttaa gtaattttgt tttagttttt    1440
tgagtaggtg gaattatagg tgtgtgttat atttggttga ttttttgtatt tttagtagag   1500
atgggttttt attatgttgg ttgggttggt tttgaattttt tgatttttagg tgatttgtat   1560
gttttggttt tttaaagtgt tgggattata ggtgtgagtt attatgtttg gttgtttaat    1620
ttttatttga agttttgggg tatatgtaga ggatgtgtag gttttgttata taggtgtgtg   1680
tgttatgatg gtttgttgta tagattattt tattatttag gtattaagtt tagtattttt    1740
tagttattttt ttttggtatt tttttttttt agtattttgt ttaataggta ttagtgtgtg   1800
ttgattgttg ttatgtgatt atgtgttttt attgtttagt ttttatttat aagtgagatt    1860
atgtggttttt gttggttttt tgtttttgtg tgagtttgtt gaggttaatg gttttttagtt   1920
ttatttatgt ttttgtaaag gatatgatta tgtttttttt agtggttgtg ttttaggtta    1980
ttttttttgg ttttgttgtt tattttttgt tgatttgtag atttttattt attttagata    2040
ttgattttttt gttggtttta gatatgatag atagttttttt ttattttatt aattgttaag   2100
tttgtttaag gagttttttta tgaaataaaa tttgttaatt taagtgtaat taaatttagt    2160
aagggatttt tgtggtgggg aagaggttgg tgtttatgtt gtattttttaa aattttattt    2220
aatgtagtta ttaaaaagaa ttagattatg ttttttgtgg gaatatggat ggagttagag    2280
gttattattt ttagtaaatt aatgtaggaa tagaaattta aatattggat gtttttattt    2340
gtaagtggga gttaaatgat gagaatttat aatataaata aggaaataat agatattgtg    2400
gttgattta gggtgtagga tgggaggaag gagaggagta gaaaagagaa ttattgggta    2460
tttggtataa tatttgggtg atgaaatatt ttgtataata a                        2501
```

<210> SEQ ID NO 21
<211> LENGTH: 20

```
<212> TYPE: DNA
<213> ORGANISM: Artificial Sequence
<220> FEATURE:
<223> OTHER INFORMATION: chemically treated genomic DNA (Homo sapiens)

<400> SEQUENCE: 21
gggattattt ttataaggtt                                              20

<210> SEQ ID NO 22
<211> LENGTH: 21
<212> TYPE: DNA
<213> ORGANISM: Artificial Sequence
<220> FEATURE:
<223> OTHER INFORMATION: chemically treated genomic DNA (Homo sapiens)

<400> SEQUENCE: 22
cccatactaa aaactctaaa c                                            21

<210> SEQ ID NO 23
<211> LENGTH: 33
<212> TYPE: DNA
<213> ORGANISM: Artificial Sequence
<220> FEATURE:
<223> OTHER INFORMATION: chemically treated genomic DNA (Homo sapiens)

<400> SEQUENCE: 23
ctaaacccca tccccaaaaa cacaaaccac aca                               33

<210> SEQ ID NO 24
<211> LENGTH: 24
<212> TYPE: DNA
<213> ORGANISM: Artificial Sequence
<220> FEATURE:
<223> OTHER INFORMATION: chemically treated genomic DNA (Homo sapiens)

<400> SEQUENCE: 24
agtttcgtcg tcgtagtttt cgtt                                         24

<210> SEQ ID NO 25
<211> LENGTH: 25
<212> TYPE: DNA
<213> ORGANISM: Artificial Sequence
<220> FEATURE:
<223> OTHER INFORMATION: chemically treated genomic DNA (Homo sapiens)

<400> SEQUENCE: 25 tttttagga atatttttag tattt                                         25

<210> SEQ ID NO 26
<211> LENGTH: 17
<212> TYPE: DNA
<213> ORGANISM: Artificial Sequence
<220> FEATURE:
<223> OTHER INFORMATION: chemically treated genomic DNA (Homo sapiens)

<400> SEQUENCE: 26
ccaaaacatc accaaac                                                 17

<210> SEQ ID NO 27
<211> LENGTH: 33
<212> TYPE: DNA
<213> ORGANISM: Artificial Sequence
<220> FEATURE:
<223> OTHER INFORMATION: chemically treated genomic DNA (Homo sapiens)

<400> SEQUENCE: 27
```
caaaccaacc atccaacacc ttactcacca caa					33

<210> SEQ ID NO 28
<211> LENGTH: 23
<212> TYPE: DNA
<213> ORGANISM: Artificial Sequence
<220> FEATURE:
<223> OTHER INFORMATION: chemically treated genomic DNA (Homo sapiens)

<400> SEQUENCE: 28
cgtagatgag gtcggagatg cgt					23

<210> SEQ ID NO 29
<211> LENGTH: 18
<212> TYPE: DNA
<213> ORGANISM: Artificial Sequence
<220> FEATURE:
<223> OTHER INFORMATION: chemically treated genomic DNA (Homo sapiens)

<400> SEQUENCE: 29
ctaaaacctc aacctaac					18

<210> SEQ ID NO 30
<211> LENGTH: 24
<212> TYPE: DNA
<213> ORGANISM: Artificial Sequence
<220> FEATURE:
<223> OTHER INFORMATION: chemically treated genomic DNA (Homo sapiens)

<400> SEQUENCE: 30
gatttagagt tgaatgtaaa gtaa					24

<210> SEQ ID NO 31
<211> LENGTH: 31
<212> TYPE: DNA
<213> ORGANISM: Artificial Sequence
<220> FEATURE:
<223> OTHER INFORMATION: chemically treated genomic DNA (Homo sapiens)

<400> SEQUENCE: 31
cctaacatct tctctcaccc caaacaaaac a					31

<210> SEQ ID NO 32
<211> LENGTH: 23
<212> TYPE: DNA
<213> ORGANISM: Artificial Sequence
<220> FEATURE:
<223> OTHER INFORMATION: chemically treated genomic DNA (Homo sapiens)

<400> SEQUENCE: 32
aacgaaacaa ataccgtaaa cga					23

<210> SEQ ID NO 33
<211> LENGTH: 20
<212> TYPE: DNA
<213> ORGANISM: Artificial Sequence
<220> FEATURE:
<223> OTHER INFORMATION: chemically treated genomic DNA (Homo sapiens)

<400> SEQUENCE: 33
aaacccaaac ctaaattaaa					20

<210> SEQ ID NO 34
<211> LENGTH: 17
<212> TYPE: DNA
<213> ORGANISM: Artificial Sequence

```
<220> FEATURE:
<223> OTHER INFORMATION: chemically treated genomic DNA (Homo sapiens)

<400> SEQUENCE: 34
ggaagtgtgt ggtaaag                                                17

<210> SEQ ID NO 35
<211> LENGTH: 28
<212> TYPE: DNA
<213> ORGANISM: Artificial Sequence
<220> FEATURE:
<223> OTHER INFORMATION: chemically treated genomic DNA (Homo sapiens)

<400> SEQUENCE: 35
taaagtgttg gggttttgtt tggttgtt                                    28

<210> SEQ ID NO 36
<211> LENGTH: 23
<212> TYPE: DNA
<213> ORGANISM: Artificial Sequence
<220> FEATURE:
<223> OTHER INFORMATION: chemically treated genomic DNA (Homo sapiens)

<400> SEQUENCE: 36
aaacaaacgt ccgaaaaaaa cga                                         23
```